('12') United States Patent
Strobl et al.

(10) Patent No.: US 12,324,876 B2
(45) Date of Patent: Jun. 10, 2025

(54) FLUID REACTORS

(71) Applicant: CVD Equipment Corporation, Central Islip, NY (US)

(72) Inventors: Karlheinz Strobl, Mt. Sinai, NY (US); James Acquaviva, East Northport, NY (US); Leonard A. Rosenbaum, Islip, NY (US); Sandra Gainey, Greenville, SC (US); Ajay Kumar, Bayport, NY (US)

(73) Assignee: CVD Equipment Corporation, Central Islip, NY (US)

( * ) Notice: Subject to any disclaimer, the term of this patent is extended or adjusted under 35 U.S.C. 154(b) by 1079 days.

(21) Appl. No.: 17/289,403

(22) PCT Filed: Oct. 31, 2019

(86) PCT No.: PCT/US2019/059228
§ 371 (c)(1),
(2) Date: Apr. 28, 2021

(87) PCT Pub. No.: WO2020/092816
PCT Pub. Date: May 7, 2020

(65) Prior Publication Data
US 2021/0393864 A1    Dec. 23, 2021

Related U.S. Application Data

(60) Provisional application No. 62/754,375, filed on Nov. 1, 2018.

(51) Int. Cl.
*A61M 1/16*    (2006.01)
*A61M 1/36*    (2006.01)
(Continued)

(52) U.S. Cl.
CPC ........ *A61M 1/1698* (2013.01); *A61M 1/3623* (2022.05); *B01D 19/0031* (2013.01);
(Continued)

(58) Field of Classification Search
CPC .............. A61M 1/1698; A61M 1/3623; A61M 2205/0244; A61M 2207/00;
(Continued)

(56) References Cited

U.S. PATENT DOCUMENTS 4,657,743 A    4/1987  Kanno
4,769,146 A    9/1988  Schmidt
(Continued)

FOREIGN PATENT DOCUMENTS

EP    0599714 A1    6/1994
EP    2758093 A1    7/2014

OTHER PUBLICATIONS

Sojoudi, et al., Stable Wettability Control of Nanoporous Microstructures by iCVD Coating of Carbon Nanotubes, ACS Appl. Mater. Interfaces 2017; 9: 43287-43299, with Supporting Information (Year: 2017).*
(Continued)

*Primary Examiner* — Daniel C. McCracken
(74) *Attorney, Agent, or Firm* — Carter, DeLuca & Farrell LLP; Amber Roibu; Peter DeLuca

(57) ABSTRACT

Fluid reactors include a sealed housing enclosing a reactor core that includes at least one substrate-free multichannel reactor core element. Each reactor core element is made from a non-substrate mounted, open pore cellular network material having an asymmetric, tortuous, bi-continuous two-phase material structure and contains multiple perforating fluid channels. Multiple reactor core elements can be serially and/or parallelly piped in a sealed manner to form a reactor core for a fluid reactor with a higher production capacity.

14 Claims, 16 Drawing Sheets

(51) Int. Cl.
  *B01D 19/00*    (2006.01)
  *B01D 67/00*    (2006.01)
  *B01D 69/02*    (2006.01)
  *B01D 71/02*    (2006.01)
  *B01J 19/00*    (2006.01)
  *C23C 16/01*    (2006.01)
  *C23C 16/04*    (2006.01)
  *C23C 16/26*    (2006.01)

(52) U.S. Cl.
  CPC ..... *B01D 67/0072* (2013.01); *B01D 67/0088* (2013.01); *B01D 69/02* (2013.01); *B01D 71/0211* (2022.08); *B01D 71/0212* (2022.08); *B01J 19/0093* (2013.01); *C23C 16/01* (2013.01); *C23C 16/04* (2013.01); *C23C 16/26* (2013.01); *A61M 2205/0244* (2013.01); *A61M 2207/00* (2013.01); *B01D 2325/022* (2013.01); *B01D 2325/026* (2013.01); *B01D 2325/38* (2013.01); *B01J 2219/00846* (2013.01); *B01J 2219/00867* (2013.01); *B01J 2219/00869* (2013.01); *B01J 2219/00907* (2013.01); *B01J 2219/00952* (2013.01)

(58) Field of Classification Search
  CPC ............ B01D 19/0031; B01D 67/0072; B01D 67/0088; B01D 69/02; B01D 71/0211; B01D 71/0212; B01D 2325/022; B01D 2325/026; B01D 2325/38; B01D 69/1411; B01D 69/14111; B01D 2256/12; B01D 2257/504; B01D 2323/58; B01D 2323/64; B01D 53/228; B01D 71/021; B01J 19/0093; B01J 2219/00846; B01J 2219/00867; B01J 2219/00869; B01J 2219/00907; B01J 2219/00952; B01J 2219/00864; C23C 16/01; C23C 16/04; C23C 16/26; Y02C 20/40
  See application file for complete search history.

(56) References Cited

U.S. PATENT DOCUMENTS

| | | | |
|---|---|---|---|
| 4,882,223 A | 11/1989 | Aptel et al. | |
| 4,906,581 A | 3/1990 | Baker et al. | |
| 4,997,564 A | 3/1991 | Herczeg | |
| 5,037,383 A | 8/1991 | Vaslef et al. | |
| 5,192,320 A | 3/1993 | Anazawa et al. | |
| 5,192,499 A | 3/1993 | Sakai et al. | |
| 5,531,848 A | 7/1996 | Brinda et al. | |
| 6,350,411 B1 | 2/2002 | Cho et al. | |
| 6,495,101 B1 | 12/2002 | Yokoyama et al. | |
| 6,667,099 B1 | 12/2003 | Greiner et al. | |
| 7,641,863 B2 | 1/2010 | Doktycz et al. | |
| 8,377,748 B2 | 2/2013 | Lee et al. | |
| 8,425,838 B2 | 4/2013 | Mizoguchi et al. | |
| 8,574,340 B2 | 11/2013 | Bakker et al. | |
| 8,685,319 B2 | 4/2014 | Olson et al. | |
| 9,138,522 B2 | 9/2015 | Palti | |
| 9,199,023 B2 | 12/2015 | Takeuchi | |
| 9,233,366 B2 | 1/2016 | Bakker et al. | |
| 9,663,368 B2 | 5/2017 | Guzman de Villoria et al. | |
| 9,670,060 B2 | 6/2017 | Dhinojwala et al. | |
| 9,771,264 B2 | 9/2017 | Garcia et al. | |
| 9,827,534 B2 | 11/2017 | Palti | |
| 2004/0173506 A1* | 9/2004 | Doktycz ............. B01D 71/021 | 210/85 |
| 2005/0181195 A1 | 8/2005 | Dubrow | |
| 2010/0285271 A1 | 11/2010 | Davis et al. | |
| 2011/0220574 A1 | 9/2011 | Bakajin et al. | |
| 2013/0112610 A1 | 5/2013 | Davis et al. | |
| 2013/0244008 A1 | 9/2013 | Wardle et al. | |
| 2014/0088725 A1 | 3/2014 | Palti | |
| 2015/0024374 A1 | 1/2015 | Palti | |
| 2015/0360182 A1* | 12/2015 | Palti ...................... B01D 63/06 | 95/45 |
| 2018/0036459 A1 | 2/2018 | Anzai et al. | |
| 2018/0036468 A1 | 2/2018 | Anzai et al. | |
| 2018/0079642 A1* | 3/2018 | Davis ................. B81C 1/00619 | |

OTHER PUBLICATIONS

Li, et al., Highly-Ordered Carbon Nanotube Arrays for Electronics Applications, Appl. Phys. Lett. 1999; 75(3): 367-369 (Year: 1999).*
Feng et al.: "Super-Hydrophobic Surfaces: From Natural to Artificial", Advanced Materials, VCH Publishers, vol. 14, No. 24, Dec. 17, 2002, pp. 1857-1860, 4 pages.
Lathuiliere et al, "Encapsulated Cellular Implants for Recombinant Protein Delivery and Therapeutic Modulation of the Immune System", International Journal of Molecular Sciences, vol. 16, No. 12, May 8, 2015, pp. 10578-10600, 23 pages.
International Search Report and Written Opinion issued in International Application No. PCT/US2020/049466 mailed Nov. 30, 2020, 19 pages.
Li et al., "Densified aligned carbon nanotube films via vapor phase infiltration of carbon", Carbon vol. 45, No. 4, Jan. 30, 2001, pp. 847-851, 5 pages.
Poelma et al., "Tailoring the Mechanical Properties of High-Aspect Ratio Carbon Nanotube Arrays Using Amorphous Silicon Carbide Coatings", Advanced Functional Materials, vol. 24, No. 36, Sep. 24, 2014, pp. 5737-5744, 8 pages.
International Search Report and Written Opinion issued in International Application No. PCT/US2019/059228 mailed Jan. 24, 2020, 25 pages.
International Preliminary Report on Patenability and Written Opinion issued in corresponding International Application No. PCT/US2019/059228 dated May 14, 2021, 15 pages.
Hanna et al., "Mechanical Property Measurement of Carbon Infiltrated Carbon Nanotube Structures for Compliant Micromechanisms", Journal of Microelectromechanical Systems, vol. 23, No. 6, Dec. 2014, pp. 1330-1339.
Ph.D. Thesis by Lawrence Barrett, "High-Aspect-Ratio Metal Microfabrication by Nickel Electroplating of Patterned Carbon Nanotube Forests", Brigham Young University, Aug. 2014, 28 pages.
ISO 7199, Cardiovascular implants and artificial organs—Blood-gas exchangers (oxygenators), Third Edition, Nov. 15, 2016, 20 pages.
FDA Standard, "Guidance for Cardiopulmonary Bypass Oxygenators 510(k) Submissions; Final Guidance for Industry and FDA Staff", Nov. 13, 2000, 23 pages.
Strobl et al., TechConnect 2019 poster titled "c-VACNT™ enabled Fluid Reactor Innovations: a NanotoMacro™ transformation": DOI: 10.13140/RG.2.2.30775.06567.

* cited by examiner

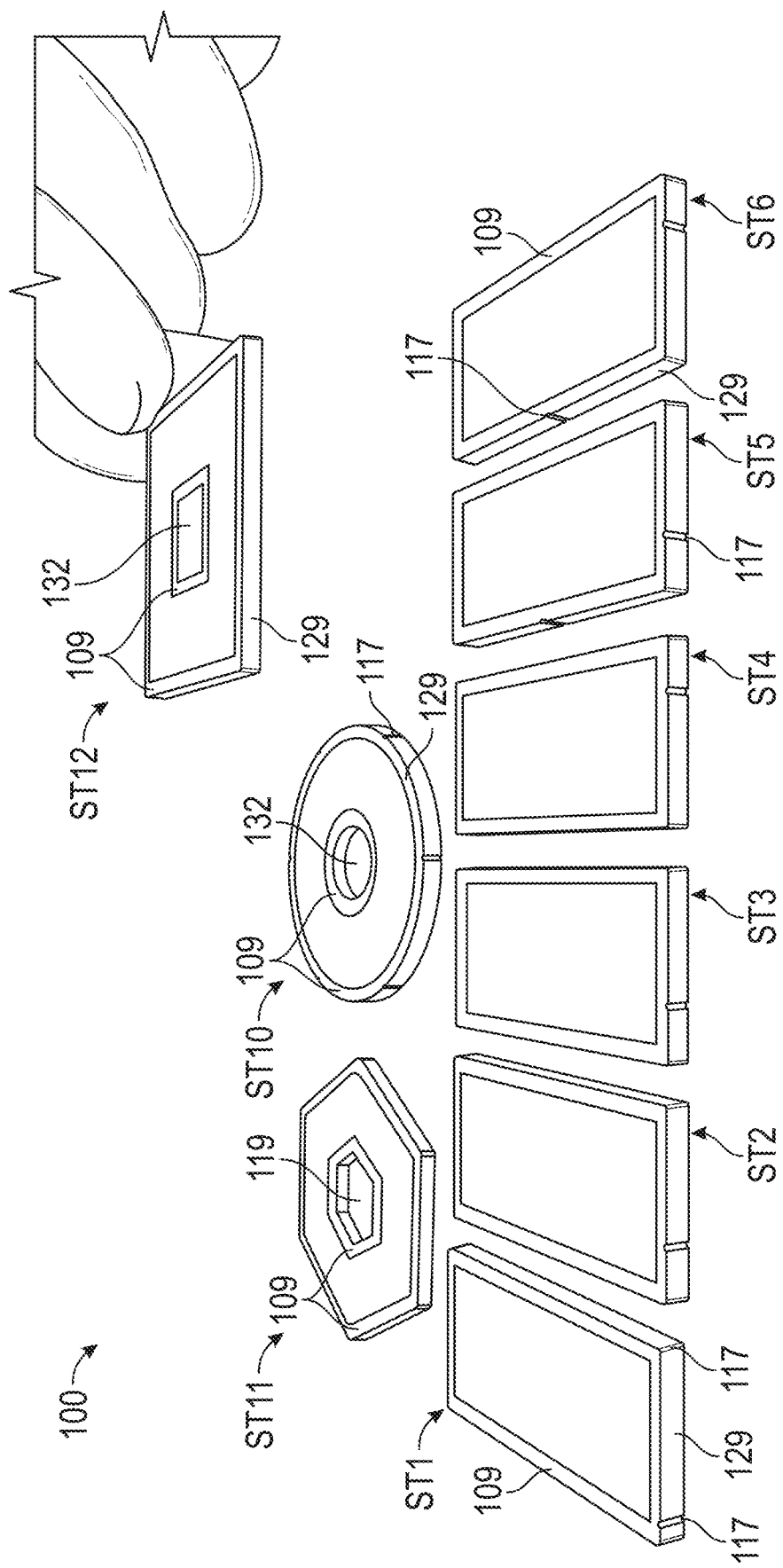

FLUID REACTORS

CROSS REFERENCE TO RELATED APPLICATIONS

This application is a National Stage of, and claims priority to and the benefit of, International Patent Application No. PCT/US2019/059228 filed Oct. 31, 2019, which, in turn, claims priority to and the benefit of U.S. Provisional Application Ser. No. 62/754,375 filed on Nov. 1, 2018, the entire contents of which are incorporated herein by reference.

TECHNICAL FIELD

This disclosure is directed to fluid reactors that incorporate at least one substrate-free, multichannel reactor core element which (i) includes an open-pore cellular network material having a bi-continuous tortuous phase structure and (ii) where at least one primary fluid is compositionally changed inside the multichannels.

BACKGROUND

Fluid reactor units typically include a sealed fluid reactor unit housing that encloses a reactor core that includes at least one reactor core element. The fluid reactor units have, at a minimum, a primary fluid input port and a primary fluid output port. In addition, they often have at least one or two secondary fluid ports, with the secondary ports being either an input or output port. Many fluid reactor units additionally have auxiliary ports for various purposes, including: venting; defoaming; removing bubbles; sampling blood; inserting saline, hepafrin, a drug, or other materials; sensing temperature, flow rate, and/or pressure; sensing levels of oxygenation, $CO_2$, pH, salinity, etc. The fluid reactor units may also include auxiliary filters (particle filters, particle agglomeration filters, arterial filters, etc.) positioned in-line with the entrance and/or exit ports and/or built into the reactor core. The reactor cores contained in these fluid reactor units are most commonly designed as either a filter module, a spiral wound module, or a hollow fiber module.

Fluid reactor units incorporating a reactor core in the form of a filter module are typically two port devices with at least one component of the primary input fluid getting preferentially trapped inside the reactor core, i.e. inside the filter module. Therefore, fluid reactor units with these filter module reactor cores have a continuously decaying flow performance behavior as the filter media gets loaded up with an accompanying increasing pressure drop behavior.

Fluid reactor units that house reactor cores including spiral wound modules or hollow fiber modules are cross-flow devices where a primary input fluid flows primarily parallel to an active membrane surface. These fluid reactor units are, at a minimum, three-port devices with the third port being a secondary fluid output or input port which allows continuous removal or addition of a secondary fluid. For example, where a fluid reactor unit operates as a filter, a primary input fluid enters the device and is separated into a concentrate, which exits the device as the primary output fluid and a permeate, which is continuously removed from the device as the secondary fluid. The additional continuous removal operation of the primary output fluid enables a much more steady and continuous filtering operation as compared to the operation of fluid reactor units having dual port filter module type reactor cores, since the buildup on the active membrane surfaces is stabilized (after an initial seasoning period) by the cross-flow fluid operation mode.

Fluid reactor units incorporating a reactor core in the form of a hollow fiber module, i.e. a bundle of many hollow fibers having a porous sidewall, are typically three or four port devices. A secondary fluid port provides a secondary input or output fluid to the reactor core and specifically to each reactor core element making up the reactor core. Such four port fluid reactor units may be used, for example, for blood oxygenation where the fluid reactor unit is used as an extracorporeal artificial lung during a cardiopulmonary bypass surgery, often also called an extra corporeal membrane oxygenator (ECMO) device.

A fluid reactor may incorporate a fluid reactor unit fluid flow controller with a sensor and a control box that receives a demand signal. When the control box controls the fluid reactor unit fluid flow controller to minimize the difference between the present value and a set value of the sensor, the fluid reactors may be referred to as a dynamically adjusting fluid reactors.

Fluid reactors with spiral wound and hollow fiber separators may also be used for reverse osmosis water desalination and many other separator applications including liquid degassing, liquid gasification, and dialysis.

There remains room for improvement in the design, manufacture, functionality, and performance of fluid reactors in general, and in particular of materials useful to build reactor core elements incorporated into fluid reactors. For example, it would be advantageous to provide higher efficiency fluid reactors, i.e. more efficient than is possible with existing hollow fiber membrane technology alone. In addition, it would be advantageous to provide fluid reactors having a higher volume efficiency, i.e. more surface area and/or processing power per reactor volume, or causing less fluid component degradation (for example, hemolysis) when used for extended times. Furthermore, it would be advantageous to provide fluid reactors that can be customized for a wide range of applications.

SUMMARY

The present disclosure is directed to novel fluid reactor designs incorporating a reactor core including at least one reactor core element that has a superior active area to volume ratio, an increased processing capacity for a given flow rate, a reduced primary fluid volume for a given processing capacity, and/or a more efficient active "membrane-like" area over which at least one secondary fluid interacts with a primary input fluid. Reactor cores in accordance with this disclosure may include parallel and/or serially connected reactor core subcomponents that each contain at least one reactor core element.

In one aspect, this disclosure is directed to open-pore cellular network materials derived from a micro- to nano-size ligament preform starting material that is subsequently interlinked and densified with a coating that mechanically bonds the ligament preforms together such that a material with a bi-continuous tortuous phase structure is formed. Such an open-pore cellular network material is suitable for manufacturing reactor core elements.

In another aspect, this disclosure is directed to performance enhancements of fluid reactor units through at least one, optionally depth-localized, application-dependent surface or near-surface coating that is applied to selected primary fluids contact areas of reactor core elements incorporated in fluid reactor units, thereby creating a skin-like region as a primary fluid contact zone that has performance enhancing, asymmetric permeable, depth localized material properties.

In another aspect, this disclosure is directed to high efficiency, continuously operating fluid reactors which include at least one fluid reactor unit, including the special cases of dynamically self-adjusting fluid reactors, and their incorporation into systems.

In another aspect, this disclosure is directed to fluid reactor units incorporating a reactor core which includes at least one substrate-free multichannel reactor core element that compositionally changes at least one primary input fluid into at least one primary output fluid inside the multichannels of the reactor core element while at least one secondary fluid enters or exits the multichannels through asymmetric permeable sidewalls of the reactor core element. The fluid reactors are designed and built to be useful for applications including, but not limited to, ultra- or micro-filtration, liquid degasification, pervaporation, liquid gasification, gas exchange, liquid/solid-gas reactions, chemical extraction, chemical or size separation, chemical processing, nano- and/or micro-material manufacturing and/or modification, biological material alteration, blood oxygenation, artificial lungs, respiratory assist device, reverse osmosis, dialysis, artificial kidneys, and/or catalyst assisted reactions.

Reactor core elements in accordance with aspects of the present disclosure include at least one reaction channel with a permeable sidewall. These permeable sidewalls may be covered with either a thin membrane film, or have a membrane-like skin function without having an actual physical membrane film that allows a higher transmission of a secondary fluid than of a component of the primary input fluid. Such a porous sidewall structure is formed from loosely arrange ligament preforms in the form of nanotubes, nanowires, nanopillars, or other micro- or nano-1D, 2D, or 3D materials that are locally spot welded by a substantially conformal thin coating. When such ligaments are given a hydrophobic coating, the porous micron- to nanostructure of the sidewalls further creates super hydrophobic properties that enhances the containment of liquids such as water-containing liquids, for example blood, inside the multichannel sidewalls.

Optionally such permeable sidewalls can also contain (for example, at least as an inside spatially localized surface coating), spatially separated catalyst particles, for example catalyst nanoparticles, to increase the reaction rate of a primary input fluid and secondary fluid near the sidewalls, thereby increasing the chemical compositional change rate, i.e. production rate, of the primary output fluid.

BRIEF DESCRIPTION OF THE DRAWINGS

The above and other aspects, features, and advantages of the present fluid reactors and the present methods of making them, as well as various subcomponents of them, will become more apparent in light of the following detailed description when taken in conjunction with the accompanying drawings in which:

FIG. 5 shows reactor core element samples of types ST1-ST6 and ST10-ST12, as listed in TABLE 1, with a hand mechanically manipulating ST12;

FIG. 10A shows a cross-sectional side view of a 4-port fluid reactor unit and FIG. 10B shows a cross-sectional top view of a 4-port fluid reactor unit; FIG. 10C shows a cross-sectional side view of a 3-port fluid reactor unit and FIG. 10D shows a cross-sectional top view of a 3-port fluid reactor unit;

DETAILED DESCRIPTION

Particular embodiments of the present fluid reactors are described hereinbelow with reference to the accompanying drawings; however, it is to be understood that the disclosed embodiments are merely exemplary of the disclosure and the present fluid reactors may be embodied in various forms.

One skilled in the art will readily recognize from the following discussion that alternative embodiments of the structures and methods illustrated herein may be employed without departing from the principles of the present disclosure described herein. Therefore, specific structural and functional details disclosed herein are not to be interpreted as limiting, but merely as a basis for the claims and as a representative basis for teaching one skilled in the art to variously employ the concepts of the present disclosure in virtually any appropriately detailed structure. Any patents, published patent applications, and non-patent publications mentioned herein are incorporated by reference herein in their entireties.

The term "fluid reactor" (sometimes also called a fluid or chemical processor, a filtration device, a membrane separator, or a chemical reactor) as used herein may be any system that changes the chemical composition of at least one flowing primary input fluid inside a reactor core element into at least one exiting primary output fluid through the continuous delivery and/or extraction of at least one secondary fluid to and/or from the reactor core element.

The chemical composition changes of a primary input fluid inside the at least one reactor core element may include, without intending to be limiting, size-limited fluid filtrations separating liquids and/or gases from solids, semi-solids, semi-liquids, emulsified liquids, molecules, DNA, polymers, nanoparticles, micron particles, etc. above a given size and/or length, particle agglomerations and/or selected biological materials. The chemical composition changes may also include concentration changes of the chemical composition of a multi-component primary input fluid. The chemical composition changes may further include concentration changes of selective gaseous and/or liquid components of a primary input fluid or chemical modifications (surface, bulk and/or localized selective reactions) of gaseous, liquid, solid, semi-solid, semi-liquid, soft, hard, simple or complex objects or particles dissolved, suspended, or transported inside a fluid. Degasification and/or gasification of a liquid, as well as any chemical modifications of selected components of the liquid are also included in the chemical composition changes, as well as insertion/removal of selected ionic components of a primary input fluid. For example, oxygenation of hemoglobin proteins and/or $CO_2$, NO released from them, selective ionic salt removal, and/or humidification changes from biological liquids are also intended to be included in the chemical composition changes.

Reactor Core Elements (RCEs)

Figure 1A:
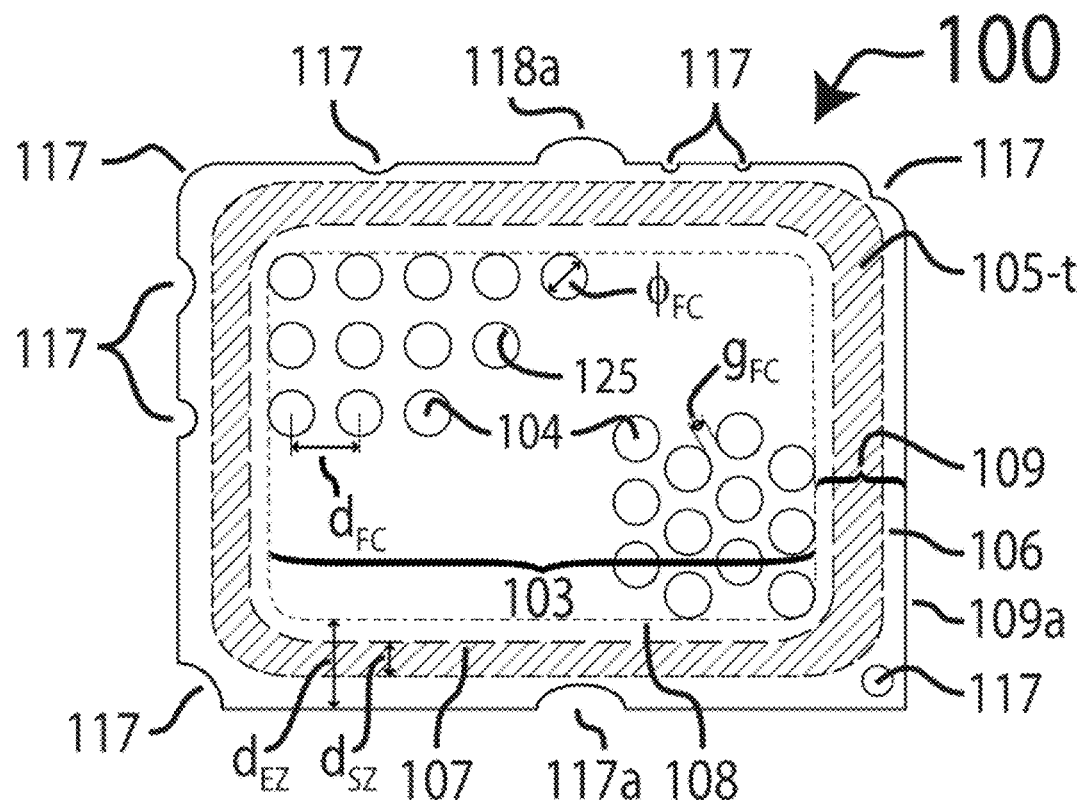
FIG. 1A schematically shows a top view of an illustrative embodiment of a simple substrate-free reactor core element.
Figure 1B:
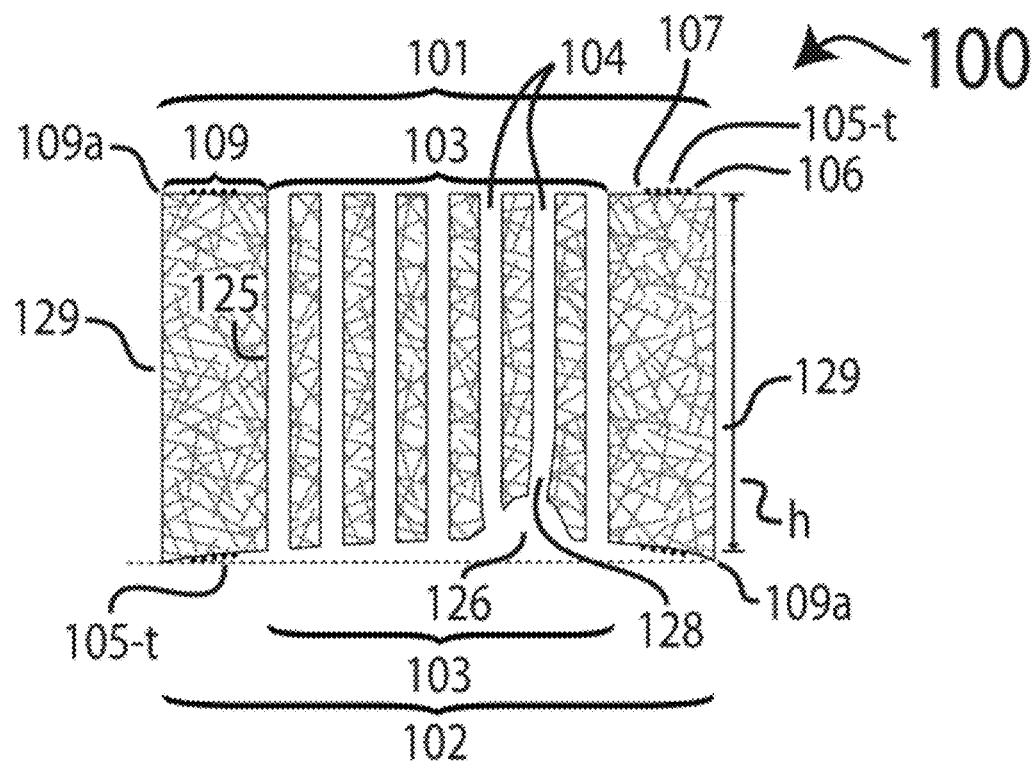
FIG. 1B schematically shows a side, cross-sectional view of a reactor core element embodiment functionally similar to the substrate-free reactor core element of FIG. 1A.
Figure 1C:
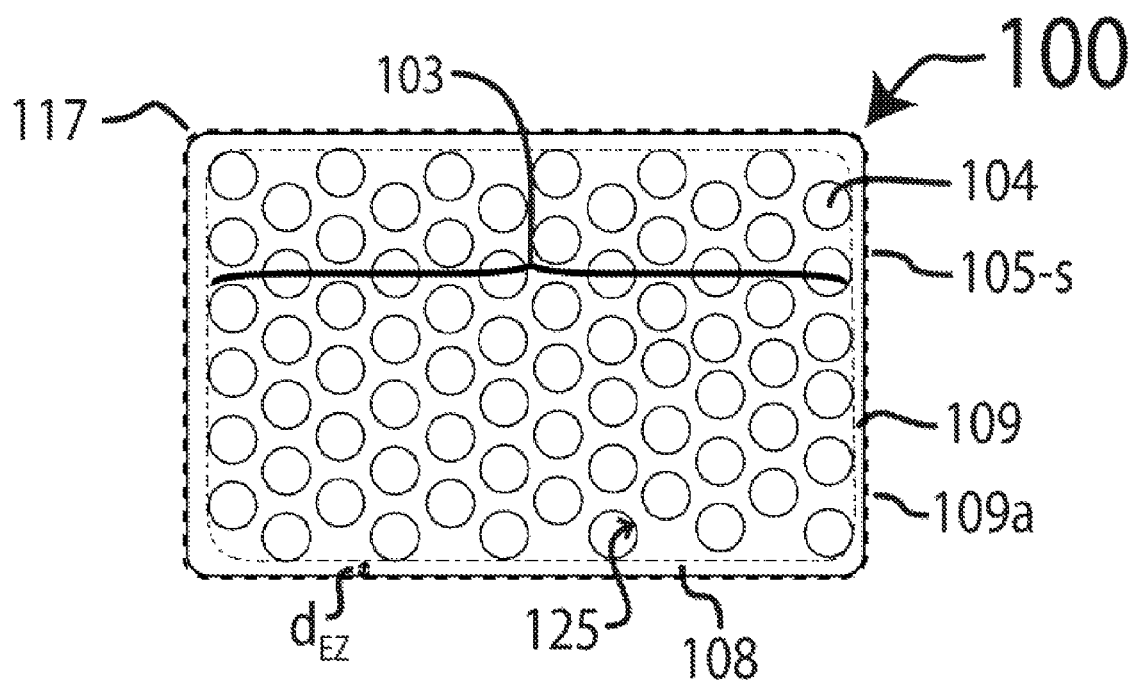
FIG. 1C schematically shows a top view of an alternative embodiment of a reactor core element having at least one sealing zone at its sidewall.
Figure 1D:
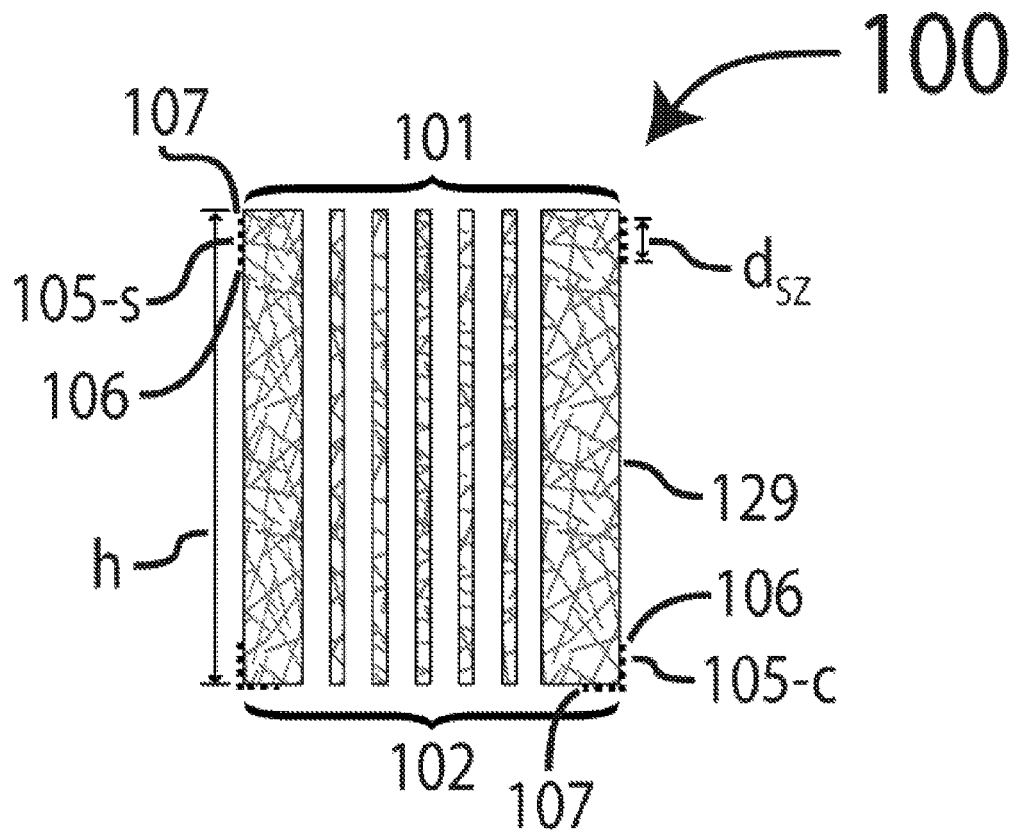
FIG. 1D schematically shows a side, cross-sectional view of a reactor core element embodiment functionally similar to the substrate-free reactor core element of FIG. 1C.

FIG. 1A and FIG. 1C show schematically a top view of non-limiting, illustrative embodiments in accordance with this disclosure of single reactor core elements 100 having a generally cuboid shape. The bottom views are generally substantially similar to the top views of these embodiments and thus have not been shown separately. FIG. 1B schematically shows a cross-sectional side view of a reactor core element 100 that is functionally similar to the reactor core shown in FIG. 1A. FIG. 1D schematically shows a cross-sectional side view of a reactor core element 100 that is functionally similar to the reactor core shown in FIG. 1C. FIGS. 1A and 1B depict reactor core elements for incorporation in a four-port fluid reactor while FIGS. 1C and 1D depict the equivalent for a three-port fluid reactor; however, it should be recognized that the features depicted in these figures may be used with either a three-port or a four-port device.

An input surface 101 with a total cross-sectional area of $CA_{RCEIS}$ is located on the front and input side of each reactor core element, and an output surface 102 with a cross-sectional area of $CA_{RCEOS}$ is located on the back and output side of each reactor core element. The average distance between input surface 101 and output surface 102 is h, which is also called the height of reactor core element. In embodiments of this disclosure, $CA_{RCEIS} \cong CA_{RCEOS}$. In other embodiments, $CA_{RCEIS} > CA_{RCEOS}$ or $CA_{RCEIS} < CA_{RCEOS}$.

Each input surface 101 and output surface 102 contains at least one fluid channel zone 103 with a cross-sectional area $CA_{FCZ}$ which contains an array of spatially isolated, active fluid channels 104 that perforate reactor core element from its input surface 101 to its output surface 102 and are surrounded (enclosed) by an edge 108. In embodiments, all fluid channel zones 103 on input surface 101 are substantially similar to all fluid channel zones 103 on output surface 102. In embodiments, fluid channels 104 are substantially parallel to each other. In embodiments, such fluid channels 104 are substantially perpendicular to input surface 101 and/or output surface 102. In embodiments, the $CA_{FCZ} < CA_{RCEIS}$ and the $CA_{FCZ} < CA_{RCEOS}$. In other embodiments, $CA_{FCZ} \cong CA_{RCEIS} \cong CA_{RCEOS}$. The length $L_{FC}$ of a fluid channel 104 is typically very close to the height h of the reactor core element, i.e. $L_{FC} \cong h$.

Figure 2A:
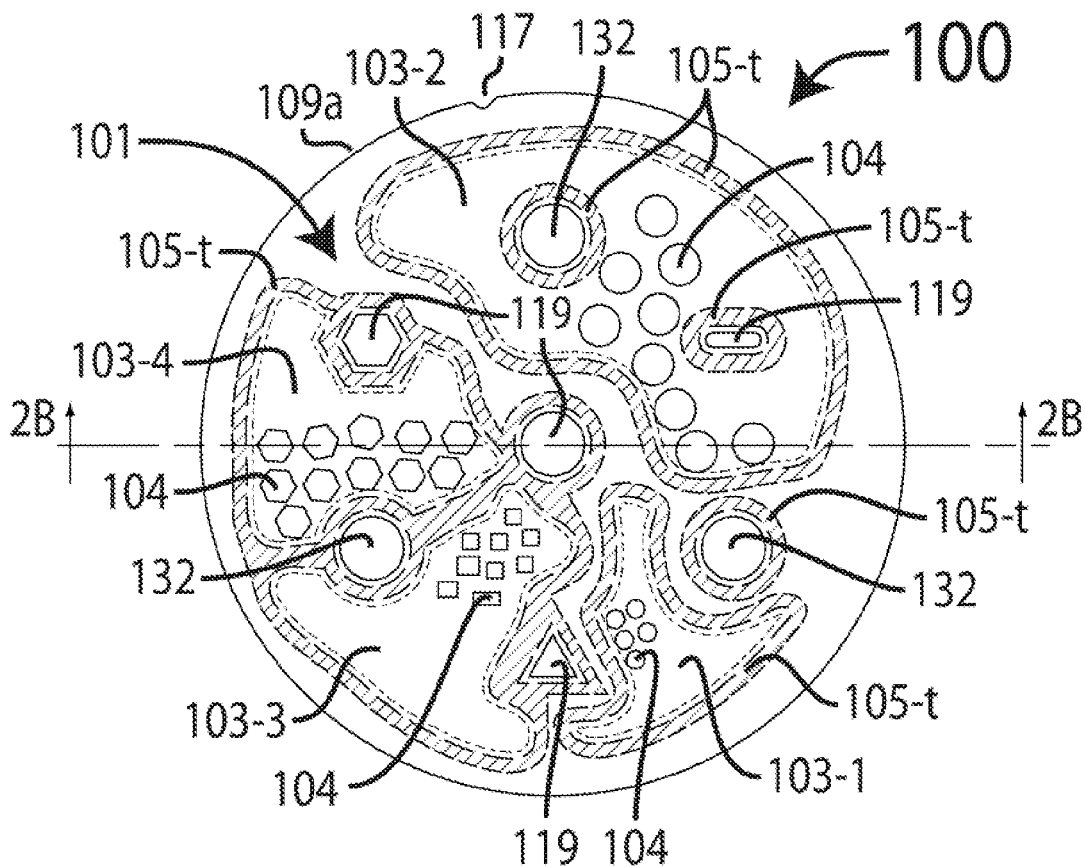
FIG. 2A shows a schematic top view and 2B shows a side, cross-sectional view of a complex substrate-free reactor core element.
Figure 2B:
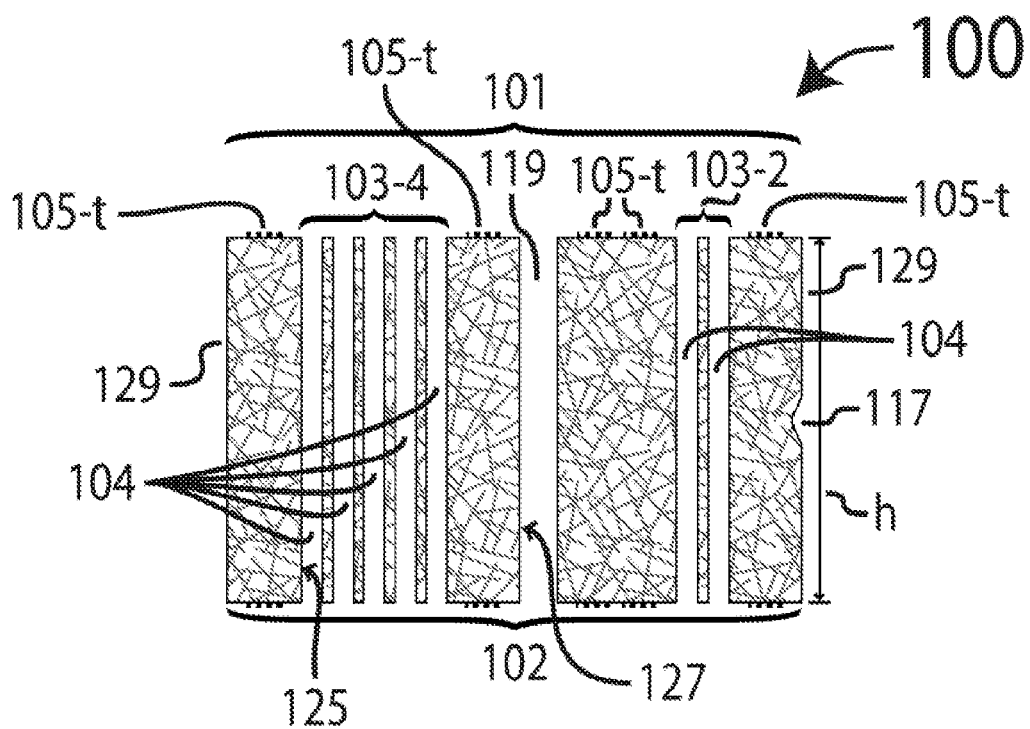

Each reactor core element has at least one sealing zone with an outer edge 106 and an inner edge 107 separated by a width $d_{SZ}$. In embodiments, $d_{SZ} \geq 5$ μm; in other embodiments, $dSZ \geq 10$ or $\geq 50$ μm. In embodiments, 5,000 μm $\geq d_{SZ} \geq 10$ μm or 1,000 μm $\geq d_{SZ} \geq 10$ μm. In yet other embodiments, 1,000 μm $\geq d_{SZ} \geq 50$ μm or 600 μm $\geq d_{SZ} \geq 400$ μm. Inner edge 107 of sealing zone is closest to fluid channels 104 or secondary fluid channel 132 or channel extrusions 119 that it encloses (secondary fluid channel 132 and channel extrusions 119 are depicted in FIGS. 2A and 2B). Only channels 104 that are fully inside the inner edge 107 have full access to a primary fluid. Any fluid channels 104 that are located fully underneath a sealing zone or outside its outer edge 106 are closed off from primary fluid contact and are therefore non-active. Any channels 104 that are partially located underneath a sealing zone may be partially active if they cross the inside edge 107. In embodiments, at least two sealing zones are present for each reactor core element, one on input surface 101 and one on output surface 102. In other embodiments, at least part of a sealing zone is on the sidewall 129.

As used herein, a sealing zone is an area of a reactor core element that is sealed by local application of a sealing material to the reactor core element in a fluid tight manner after manufacturing of the reactor core element is completed, before or during its incorporation into a reactor core subcomponent or fluid reactor unit housing 304 (as further discussed below).

Sealing zones may be (i) a sealing zone 105-t (where "t" stands for top) located fully on a portion of the input and/or output surface 101 and/or 102, as shown in FIGS. 1A and 1B for example, (ii) a sealing zone 105-s (where "s" stands for sidewall) which is located fully on a portion of the external sidewall 129 of the reactor core element 100, as shown in the top portion of FIG. 1D for example, or (iii) a sealing zone 105-c (where "c" stands for corner) which is located at least partially on a portion of the sidewall 129 and on a portion of the input or output surface 101 or 102, as shown in the bottom portion of FIG. 1D for example.

FIGS. 1A and 1B show embodiments where a single sealing zone 105-t (shown with hashed lines and/or dashed lines) encloses fluid channels 104 on the input surface 101 of the reactor core element 100. In these embodiments, the bottom surface is substantially equivalent to the top surface, though in other embodiments, the top and bottom surfaces could be different. Sidewalls 129 connect input surface 101 and output surface 102. Sidewalls 129 provide a possible entrance or exit surface for a secondary fluid. In embodiments, sealing zones 105-$t$ on an input and output surface 101 and 102 are substantially similar.

FIGS. 1C and 1D show an alternative embodiment where at least one sealing zone 105-$s$ is located on sidewall 129 of the reactor core element outside the input surface 101 and one sealing zone 105-$c$ is located around the corner of the reactor core element and, thus, is located both on output surface 102 and on sidewall 129. As those skilled in the art reading this disclosure will appreciate, sealing zone 105-$c$ runs around the whole edge of the reactor core element. It should be understood that in embodiments one sealing zone 105-$t$ may be located on input surface 101 and another sealing zone 105-$s$ may be located on sidewall 129 near the output surface 102. Alternatively, in other embodiments, sealing zone 105-$t$ may be on output surface 102 and sealing zone 105-$s$ may be on sidewall 129 near the input surface 101. In other embodiments, one sealing zone 105-$c$ may be located around the top corner of the reactor core element 100 and, thus, located both on input surface 101 and on sidewall 129. In embodiments, two separate sealing zones of 105-$s$, 105-$c$, or mixed type may overlap at least locally into a single sealing zone.

In embodiments, in particular when multiple sealing zones are provided on input surface 101 (as discussed below in relation to FIGS. 2A and 2B), the number of sealing zones on output surface 102 can be fewer and/or have different shapes and/or sizes and/or at least one may be a different type of sealing zone (e.g., 105-$s$ or 105-$c$ sealing zone type rather than a 105-$t$ type sealing zone). For example, two sealing zones with at least one 105-$t$ type, each enclosing a fluid channel zone 103 on input surface 101 of the reactor core element, can be combined into one single sealing zone which encompasses both fluid channel zones 103 (now forming just a single fluid channel zone 103) on output surface 102 of the reactor core element. Combinations of the above sealing zone embodiments and obvious variations of sealing zone locations and full or partial overlaps of multiple sealing zones are also considered.

Optionally, an exclusion zone 109 having an average width $d_{EZ}$ is located between outer edge 109$a$ of input surface 101 and output surface 102 and outer edge 108 of input or output fluid channel zone 103. In embodiments, no exclusion zone 109 is present, i.e. $d_{EZ} \approx 0$ μm, and fluid channels are located right up to sidewalls 129. Sealing zones can then optionally fully or partially block as least some fluid channels 104 and therefore make them non-active.

FIGS. 1A, 1B, 1C, and 1D depict embodiments in the form of a simple reactor core element 100 with a single sealing zone enclosing a single fluid channel zone 103. Sidewalls 129 may have notches 117 and/or protrusions 118 that can act as ID markers and/or alignment features. Such notches 117 and protrusions 118 may optionally be extrusions. In embodiments, notch 117 may be a channel. Notches 117 and protrusions 118 can come in a variety of shapes and sizes. FIG. 1A depicts various sized v- or u-shaped notches 117 along outer edge 109$a$, as well as cylindrical, double curved, concave, and rounded corner notches 117 on the four corners of reactor core element 100. Other notch 117 and protrusion 118 shapes, whether or not extruded, are considered as well for this disclosure including, but not limited to, bullnose-like corners, tongue and groove like features (see FIG. 2B), jigsaw puzzle like features, steps, slopes, and other interlocking and non-interlocking features that may be suitable for a chosen alignment task. When used as alignment features, notches 117$a$ may optionally be paired with a matching protrusion 118$a$, as depicted in FIG. 1A. Such matching alignment features 117$a$ and 118$a$ can be used to lock two reactor core elements 100 precisely to each other, like in an assembled jigsaw puzzle, and/or to help create a controlled gap between neighboring sides of adjacent reactor core elements 100. One or more notches 117 or protrusions 118 can be used, for example, for mechanically locating a reactor core element 100 to a predetermined spatial position, such as in relation to a mounting location and/or locating pin and/or a sealing gasket with alignment features (e.g. holes or molded protrusions).

Two types of approximately uniformly spaced fluid channel 104 layout arrangement embodiments are shown in FIG. 1A: a rectangular spatial layout in the upper left-hand corner of FIG. 1A, and hexagonal spatial layout lower right-hand corner of FIG. 1A, with each fluid channel 104 having an average substantially round cross-sectional area $CA_{FC}$, a fluid channel diameter value $\phi_{FC}$, a channel to channel spacing distance $d_{FC}$, and a minimum channel gap distance $g_{FC}$. Each extruded fluid channel 104 has a sidewall 125 with a surface area $SA_{FC}$ which, in the two embodiments of this disclosure shown in FIG. 1A, may have the shape of a substantially constant diameter cylindrically wall.

Alternative spatial layout arrangements for fluid channels 104 are considered, including layouts with non-constant values for $g_{FC}$, $\phi_{FC}$, and/or $CA_{FC}$ and fluid channels 104 with different cross-sectional shapes (hexagonal, square, rectangular, triangular, trapezoidal, elliptical, oval, tear dropped, other polygon shapes, other closed shapes with stepwise straight and/or curved sections, etc.).

In other embodiments, the cross-sectional shape, area, and/or length of at least some of the available fluid channels 104 is allowed not to be constant. For example, the cross-section of sidewall 125 can transition from a circle to an oval or tear drop shaped curve for at least one of the available fluid channels 104 for at least some distance along the fluid channel 104 length direction of a given reactor core element 100. FIG. 1B shows an embodiment where input surface 101 is flat and where output surface 102 is slightly curved with a distortion zone 126. Near distortion zone 126, the fluid channel 104 direction and spacing to its nearest neighbor can be distorted when transitioning from input surface 101 to output surface 102. In such distortion zones 126 changes in the cross-sectional shape and/or length ($L_{FC}$) of the fluid channels 104 can arise, for example, from manufacturing process limitations of a chosen manufacturing process used to manufacture such reactor core elements 100 (see discussions related to FIG. 7). In addition, due to local manufacturing defects, a given fluid channel 104 can be partially or fully clogged (for example, mechanically blocked with foreign matter) along at least a portion of its length. Manufacturing defects can also result in a fluid channel 104 that is at least partially sealed on input surface 101 or output surface 102 side of fluid channel 104, for example, with a thin membrane-like film (sometimes called a "floor layer" herein) covering all or part of a fluid channel 104 entrance/exit area as will be discussed in more detail below.

Which of the two-possible input/output sides of a given reactor core element 100 is the input side is typically not important, but a particular orientation may aid in the manufacturing process of a reactor core subcomponent 250, reactor core 200, and/or fluid reactor unit 300 and/or may help with the formation of the seal creating a sealing zone. In embodiments, the flatter side of reactor core element 100 is chosen as its input side. In other embodiments, the input side of the reactor core element 100 is chosen randomly. In yet other embodiments, the input side is chosen as the less flat side or as the side which has less blockage with foreign matter inside the ends of its fluid channels 104. Such distorted and/or partially and/or fully blocked fluid channels 104, depending on the application of a given fluid reactor incorporating such reactor core elements 100 having at least some "less than perfectly shaped" fluid channels 104, typically will still at least partially contribute to the overall "reaction" capacity of the fluid reactor and often can be counted as active. Equation (1) below shows that the flow rate of a given fluid channel is proportional to $\phi^4_{FC}$ and inversely proportional to its height h. Since the thickness of such possible membranes are typically less than 100 nm, and more often less than 50 or 20 nm, such partial membrane blockages act more like an orifice restriction than a fluid channel diameter restriction. Above a specified "blockage/distortion" threshold (that is typically dependent upon the application of the fluid reactor incorporating a reactor core element), such fluid channels can be considered effectively fully blocked fluid channels and therefore treated as non-active. Such fully blocked and effectively fully blocked fluid channels (i.e. defective fluid channels) will not allow normal primary input fluid flow through them and thus will diminish the total flow capacity of a given reactor core element proportional to the ratio of the total number of such "defective" fluid channels to the total number fluid channels 104 fully inside the inner edge of a respective sealing zone. In addition, manufacturing defects like through-holes (at least below a certain cross-sectional size and quantity threshold) outside a sealing zone are typically less of a problem (minor mechanical strength loss) as compared to holes or through-holes located inside a sealing zone or near its inner edge since such holes (depending on their size compared to $d_{SZ}$ and location relative to inner edge) could prevent a proper seal from being formed, thus enabling primary fluid to leak outside its designated flow area.

Therefore, in embodiments, even somewhat imperfectly formed reactor core elements may be used to build a fluid reactor in accordance with this disclosure with the understanding that such fluid reactors have a proportionally diminished production capacity, also called fluid reaction capacity herein, but otherwise function normally, as long as all the sealing zones are functional, i.e. are sufficiently sealable for the intended use, and there are no large-sized through holes and/or the total area of through holes other than fluid channels 104 inside fluid channel zone 103 is below an application and fluid reactor design dependent threshold.

The fluid flow rate $F_{FC}$ controlling the fluid transport of an uncompressible fluid, for example a liquid, through a round fluid channel is related to the primary fluid pressure drop $\Delta P_{PF}$ along its length $L_{FC}$ (also called height h hereinafter) of the fluid channel, its fluid channel diameter $\phi_{FC}$, and the viscosity $\eta_{PF}$ of the primary fluid flowing through said fluid channel through the Poiseuille's law formula $$F_{FC} = \frac{\Delta P_{PF}}{R_{PF}} = \frac{\Delta P_{PF} * \pi * \phi^4_{FC}}{128 * \eta_{PF} * h} \quad (1)$$

with $R_{PF}$ representing the primary fluid flow resistance of the fluid channel.

For the special case where the primary input fluid and primary output fluid flow rate through a reactor core element is substantially similar (i.e. for the case where the quantity of primary fluid lost through porous sidewall can be neglected) the primary fluid flow rate $F_{FCZ}$ can be calculated with the below formula $$F_{FCZ} = \sum_{i=1}^{N} F^i_{FC} \quad (2)$$

with $F^i_{FC}$ representing the fluid flow through the i-th fluid channel defined by equation (1) and with N representing the number of active fluid channels 104 located inside all fluid channel zones. For the special case of a simple reactor core element having a single fluid channel zone with a hexagonal spatial layout arrangement of round fluid channels 104 located inside a rectangular fluid channel zone having a rectangular cross-sectional area $CA_{FCZ}=W_{FCZ}*L_{FCZ}$ with width $W_{FCZ}$ and length $L_{FCZ}$, the maximum number of active fluid channels N can be calculated or estimated with the full or simplified formula $$N = \frac{2*CA_{FCZ}}{\sqrt{3}*(\phi_{FC}+g_{FC})^2} + \frac{2*W_{FCZ}+\sqrt{3}*L_{FCZ}}{\sqrt{3}*(\phi_{FC}+g_{FC})} + 1 \approx \quad (3)$$

$$\frac{2*CA_{FCZ}}{\sqrt{3}*(\phi_{FC}+g_{FC})^2} \text{ for } (N \gg 1)$$

from the fluid channel diameter $\phi_{FC}$ and the smallest gap $g_{FC}$ between two neighboring fluid channels.

Similarly, the total active surface area $SA_{FCZ}$ of a reactor core element and its ratio to the envelope volume $V_{RCE}$ enclosing said reactor core element can be calculated from the formulas $$SA_{FCZ} = \sum_{i=1}^{N} SA^i_{FC} \quad (4)$$

and $$SA_{FCZ}/V_{RCE} = \sum_{i=1}^{N} \frac{SA^i_{FC}}{W_{RCE}*L_{RCE}*h} \quad (5)$$

for a reactor core element 100 having a width $W_{RCE}$, length $L_{RCE}$, thickness or height h, and surface area $SA^i_{FC}$ for the i-th fluid channel.

When all fluid channels are identical, active, laid out in a hexagonal pattern, and located inside a single fluid channel zone of a reactor core element, then the total primary input fluid flow rate $F_{FCZ}$ entering the fluid channel zone is $$F_{FCZ}=N*F_{FC} \quad (5a)$$

with $F_{FC}$ defined in equation (1). The total surface area of all fluid channels 104 is $$SA_{FCZ} = N*SA_{FC} \approx \frac{2*\pi*\phi_{FC}*h*CA_{FCZ}}{\sqrt{3}*(\phi_{FC}+g_{FC})^2} \text{ for } (N \gg 1) \quad (5b)$$

which reaches its maximum value $$SA_{FCZ}^{max} = \frac{\pi*h*CA_{FCZ}}{2*\sqrt{3}*\phi_{FC}} \text{ for } \phi_{FC}=g_{FC}. \quad (5c)$$

FIG. 2A shows a top view and FIG. 2B shows a side, cross-sectional view of other embodiments in the form of a more complex shaped reactor core element 100, shown here in the form of a cylindrical disk shaped reactor core element 100 with a height h, where input surface 101 and output surface 102 have optional multiple spatially isolated fluid channel zones 103-*m* (with m=1 through 4 shown in FIG. 2A), and where multiple complex shaped sealing zones (shown as 105-*t* type) surround fluid channel zones 103-*m*. FIG. 2B shows an embodiment where both input surface 101 and output surface 102 are flat and substantially parallel to each other. The bottom view of this element 100 is not shown in FIG. 2A but is substantially equivalent to FIG. 2A. Near the center of input surface 101 and output surface 102, an optional channel extrusion 119 is depicted as having a cylindrical shape. Other optional channel extrusions 119 are also shown throughout input surface 101 and output surface 102 in the not intended to be limiting cases of hexagonal, triangular, and racetrack cross-sectional shapes. An optional notch 117 is shown along outer edge 109*a* of reactor core element 100 as one example of the many possible alignment feature and/or ID marker options. Channel extrusions 119 differ from alignment notches 117 in that channel extrusions are isolated by a sealing zone. Similar to notches 117, channel extrusions 119 may be used as ID markers and/or alignment features. FIG. 2A also shows three secondary fluid channels 132 that perforate reactor core element 100 in a direction parallel to fluid channels 104 and that allow a secondary fluid to flow therethrough. FIG. 2B shows an alternative form of a notch 117 in sidewall 129 as an example of an alignment feature and/or ID marker that that is not extruded.

FIG. 2A depicts multiple embodiments of sealing zones: a sealing zone 105-*t* enclosing just a single fluid channel zone 103-1; a sealing zone 105-*t* enclosing a fluid channel zone 103-2 that includes an optional channel extrusion 119 and a secondary fluid channel 132, with both channels being sealed by another single contour shaped sealing zone 105-*t* and isolated from fluid channel zone 103-2; and a sealing zone 105-*t* that encloses two fluid channel zones 103-3 and 103-4, as well as multiple channel extrusion 119 and a secondary fluid channel 132. In embodiments, when geometrically possible, all sealing zones 105-*t* could be sealed with a single complex shaped gasket having appropriate cut-outs for fluid channel zones 103-*i*, and all secondary fluid channels 132 and channel extrusions 119. All sealing zones 105-*t* in FIG. 2A are located either on input surface 101 or output surface 102. In alternative embodiments, 105-*s* or 105-*c* type sealing zones may be used alone or in various combinations for a complex reactor core element 100 of the type shown FIGS. 2A and 2B.

A sealing zone isolates (a) any enclosed fluid channel zones 103, (b) any enclosed secondary fluid channels 132, and/or (c) any enclosed channel extrusions 119 from one another. In embodiments, at least one channel extrusion 119 or secondary fluid channel 132 is located inside a single zone 105-*t*. FIG. 2A shows multiple embodiments for fluid channels 104 having different cross-sectional shapes, sizes, gaps, and/or spatial arrangements as suitable for a given fluid reactor application. Not explicitly shown, but intended to be included herein, are also continuous and discontinuous cross-sectional areas, cross-sectional shape changes, and/or gap changes between neighboring fluid channels 104 when transitioning along the direction from input surface 101 to output surface 102 or inside various fluid channel zones 103.

A sealing zone surrounding a fluid channel zone 103 on an input surface 101 and on an output surface 102 can be substantially similar or can be different. For example, a single sealing zone 105-*t* on output surface 102 is also envisioned as one of the embodiments of this disclosure that surrounds two or more available fluid channel zones 103-*i* on its input surface 101. In embodiments, all sealing zones may be substantially similar on both input surface 101 and on output surface 102 at least near the vicinity of secondary fluid channels 132 and/or extrusions 119 to prevent any primary fluid leakage.

In other embodiments (not depicted in any figures), one or more of these channel extrusions 119 can also serve as a secondary fluid channel 132, if an alignment tube (not shown) is positioned inside a channel extrusion 119, and the alignment tube has, at a minimum, a suitable sized hollow core that can deliver the required flow for a secondary fluid into targeted locations, i.e. it has, at a minimum, a tube-like structure with appropriate entrance/exit holes. Optionally, the alignment tube may connect multiple reactor core elements 100 in series (referred to as a reactor core stack 210, as discussed below). Optionally, such an alignment tube also has at least some perforations at strategic locations along its sidewalls allowing a secondary fluid to enter or exit a gap between two neighboring input surfaces 101 and output surfaces 102 of two serially stacked reactor core elements 100 (see more details below) and/or to diffuse in or out of the material surrounding such secondary fluid channels 132 along its length.

Various examples of complex reactor core elements 100 are shown in FIG. 5 with the round (ST10), hexagonal (ST11), and square (ST12) shaped complex reactor core elements 100 having a round, hexagonal, and square shaped channel extrusion 119 or secondary fluid channel 132, depending on the application, that can also be used to localize the center of each reactor core element and in the ST11 and ST12 case also aids in their orientation. Additional notches 117 are also incorporated along sidewall 129 of some of these samples. In other embodiments, such complex reactor core elements 100 can have a fully sealed sidewall 129 with a single sealing zone 105-*s* or a partially sealed sidewall 129 with at least two sealing zone 105-*s* or 105-*c* types.

FIGS. 1B and 2B show an embodiment where the fluid channels 104 are arranged substantially perpendicular to the average plane of input surface 101 and output surface 102. FIG. 2B shows an embodiment where both input surface 101 and output surface 102 are flat and substantially parallel to each other. FIG. 1B shows an embodiment where input surface 101 is flat and where output surface 102 is slightly curved with a distortion zone 126. Possible local bending 128 of the impacted fluid channels 104 near local distortion zones 126, also allowed in a further embodiment, is also shown in FIG. 1B, while possible related cross-sectional area and/or shape changes (also allowed) are not shown.

Other arrangement embodiments are also considered for this disclosure where, either intentional or due to manufacturing limitations, or due to intentional additional manufacturing steps applied during the manufacturing of such reactor core elements 100, input surface 101 and/or output surface 102 have (i) parallel surfaces to each other, (ii) a substantially similar curvature, (iii) a different curvature (as shown in FIG. 1), (iv) a convex or concave shape (as shown in FIG. 1), (v) a raised lip-like input surface 101 and/or output surface 102, (vi) a lowered bullnose-like input surface 101 and/or output surface 102, or (vii) a combination thereof.

Optionally, reactor core elements 100 with two parallel input surfaces 101 and output surfaces 102 may be bowed, as long as they are sufficiently mechanical resilient and spring-like and they can be flattened or bent to the surface of a primary fluid connection manifold 203, 204, or 206 during a sealing zone formation process; such flattening or bending can be done by applying a pressure that is not strong enough to cause a structural damage to such a reactor core element 100. Such bowing of reactor core element 100 can arise, for example, from the limitations of a chosen manufacturing process of reactor core element 100, for example, an uneven drying process step 184. In embodiments of this disclosure, the average plane of input surface 101 and/or output surface 102 are tilted either against each other (for example, forming a wedge) and/or are non-perpendicular against the average extrusion direction of its fluid channels 104. Such non-perpendicular and/or non-flat input and output surfaces can be achieved, for example, with intentional or accidental wedge grinding of reactor core element 100 as known to those skilled in the art, and/or as a side effect of a given manufacturing process step and/or due to a secondary intentional manufacturing process step, for example, process step 176, 179, or 182.

The sum of all surface areas (sometimes also called regions or zones) located on the input surface 101 or output surface 102 (and, in some instances, also located on at least part of the sidewalls 129) within the inner edges 107 of all sealing zones enclosing at least one fluid channel zone 103, but excluding (i) the sum of all primary fluid entrance and exit areas of all fluid channels 104 located inside all sealing zones and (ii) the sum of all areas formed by all outer edges 106 of any optional sealing zones located inside another sealing zone surrounding a secondary fluid channel 132 and/or channel extrusion 119, form the primary input fluid contact surface or primary output fluid contact surface. The sum of all fluid channel sidewalls 125 of a reactor core element 100 form the fluid channel primary fluid contact surface which has a total surface area $SA_{FCZ}$, as defined above in Equation (4). The sum of the primary input fluid contact surface, the primary output fluid contact surface, and the fluid channel primary fluid contact surface form the primary fluid contact surface of a given reactor core element 100, i.e. the portion of a given reactor core element 100 that is in actual contact with a primary fluid, whether it is a primary input fluid and/or a primary output fluid. The transformation of a primary input fluid to the primary output fluid happens inside fluid channels 104, as will be discussed in more detail below.

The secondary fluid external contact surface for a given reactor core element 100 includes of all surface areas of the reactor core element 100 (including the sidewalls of any secondary fluid channels 132 or channel extrusions 119) except those surface areas located within a fluid channel zone 103 and those surface areas that later become a sealing zone. The secondary fluid external contact surface can be a secondary fluid external input surface or a secondary fluid external output surface, as discussed below.

In embodiments, a single secondary fluid is delivered or removed from reactor core element 100 through at least a portion of the secondary fluid external contact surface, which includes in its majority the unsealed part of the reactor core element sidewall 129 and the sidewalls of any available secondary fluid channels 132 and/or channel extrusions 119. In other embodiments, a first secondary fluid, i.e. a secondary input fluid, is delivered to a first portion of the secondary fluid external contact surface and a second secondary fluid, i.e. a secondary output fluid, is removed from a second portion of the secondary fluid external contact surface, with both portions of the secondary fluid external contact surface being fluidly isolated from each other by any sealing means known to those skilled in the art and as discussed below.

In embodiments, for a reactor core element 100, one or more suitable gaskets, O-rings, epoxy fillings, caulking means, plastic molds, or other means known to those skilled in the art separate its sidewall 129 into at least two separate outside surfaces, i.e. a secondary fluid external input surface and a secondary fluid external output surface, and optionally further block at least most of the remaining portions of its secondary fluid external contact surface located on sidewall 129 from participating in secondary fluid transmission. For example, in further embodiments, the left and right sidewalls of the cuboid-like reactor core element 100 shown in FIG. 1A or FIG. 1C are sealed against secondary fluid flow. In this case, a secondary input fluid enters reactor core element 100 only through secondary fluid external input surface, travels through reactor core element 100, and then exits as a secondary output fluid only through the secondary fluid external output surface, thus providing a substantially uniform front to back primary output fluid flow for this type/shape of reactor core element 100. When no secondary input fluid exists, the source of a secondary output fluid is the active fluid channels 104, as will be discussed in more detail below. When there is both a secondary input fluid and a secondary output fluid, the transformation of the secondary input fluid to the secondary output fluid happens inside fluid channels 104, as will be discussed in more detail below.

Figure 10A:
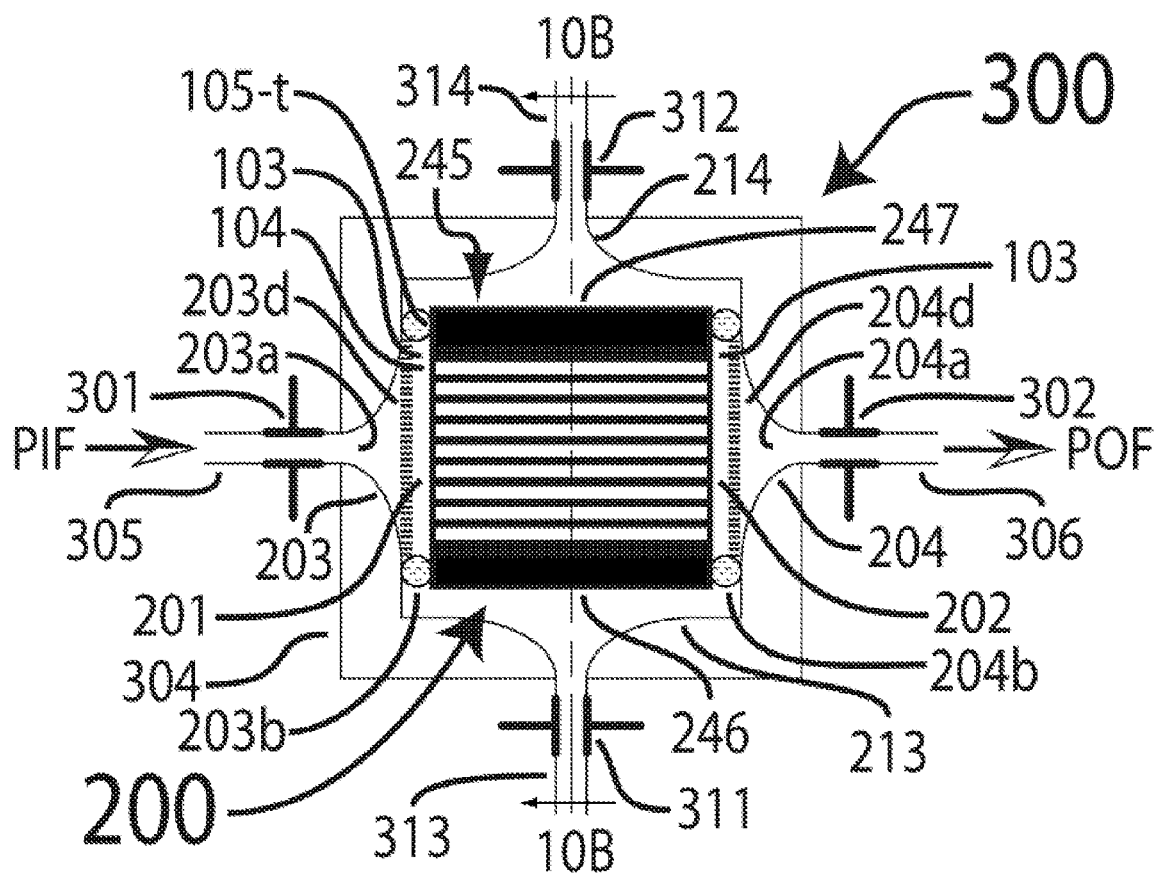
FIG. 10A-D shows a three- or four-port fluid reactor unit with a fluid reactor unit housing enclosing a reactor core.
Figure 10B:
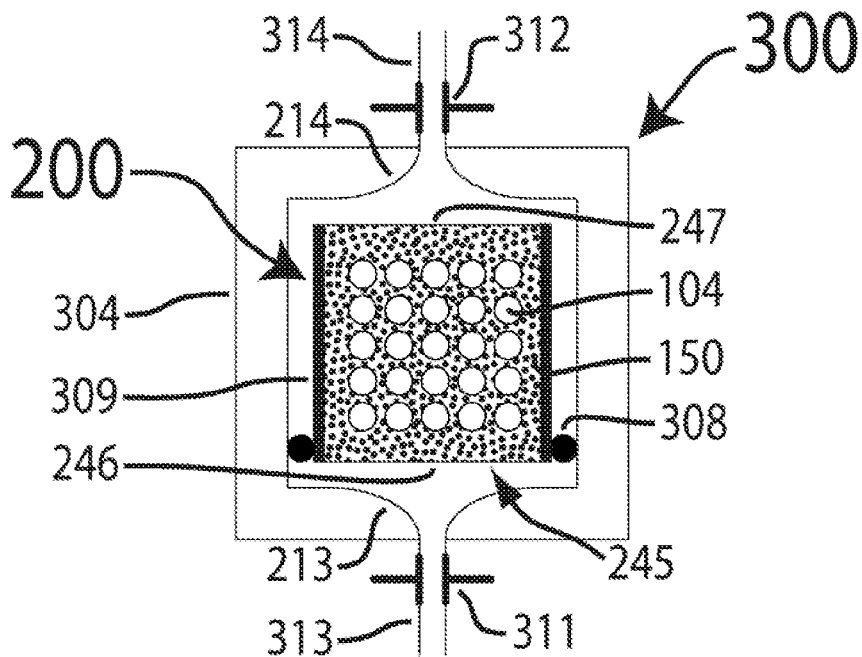

Reactor core elements 100 which have part of secondary fluid external contact surface sealed (for example, as discussed in the previous paragraph or as shown in FIG. 10B) are called hereinafter E-type reactor core elements 100, with "E" standing for "partial edge sealed."

In embodiments, as indicated in FIGS. 2A and 2B, one or more sealing zones 105-$t$ enclosing a secondary fluid channel 132 are used to spatially separate a secondary input fluid from a secondary output fluid. In embodiments, the sidewall 127 of at least one secondary fluid channel 132 or channel extrusion in a complex reactor core element 100 can be used as a secondary fluid external output surface or secondary fluid external input surface, or at least as a portion of it, as can the sidewall 129. In embodiments, for a complex reactor core element 100, the sidewall 127 and/or sidewall 129 is either fully sealed and optionally is part of sealing zone, or at least the portion of sidewall 127 or sidewall 129 that does not have a sealing zone partially sealing it comprises the secondary fluid external contact surface, which can be a secondary fluid external input surface, a secondary fluid external output surface, or divided into both an input surface and output surface.

In embodiments, the secondary fluid travels from a larger sized secondary fluid external input surface to a smaller sized secondary fluid external output surface. For example, when the secondary input fluid travels from an outside peripherally located larger secondary fluid external input surface on the sidewall 129 through the body of a complex reactor core element 100 to a smaller inside located secondary fluid external output surface (for example, the centrally located hexagonal, round, or rectangular shaped secondary fluid channels 132 shown in FIG. 5 for samples ST10, ST11, and ST12), the secondary fluid velocity increases, thus compensating for the local concentration change of the secondary input fluid and/or secondary output fluid, and thus providing a more uniform fluid channel 104 chemical composition change performance than when the secondary fluid external input surface and secondary fluid external output surface are reversed. The reverse secondary fluid flow direction is also embodiments, but typically produces inferior productivity results. For three-port fluid reactor applications, all of the available secondary fluid external contact surface can be used for delivery or removal of a secondary fluid.

TABLES 1 and 2 show reactor core element performance-related values for a group of special sample cases of reactor core elements having a hexagonal pattern of evenly spaced, round identical fluid channels inside a single fluid channel zone. TABLE 1 shows the sample performance for reactor core elements having an exclusion zone width $d_{EZ}$=1.5 mm. TABLE 2 shows the sample performance for $d_{EZ}$=0.5 mm. $V_{FCZ}$ and $SA_{FCZ}$ represent the total volume and total active surface area of all available and active fluid channels and $CA_{RCE}$ represents the top cross-sectional area. The performance of the individual reactor core elements affects the efficiency of a fluid reactor unit incorporating such reactor core elements.

and $V_{RCE}$ listed in TABLES 1 and 2 include the volume of the centrally located secondary fluid channel or alignment channel.

For the samples listed in TABLE 1, 16%-34% of the envelope volume $V_{RCE}$ enclosing the reactor core element is occupied by fluid channels, i.e. $V_{FCZ}/V_{RCE}$ represents the active primary fluid volume percentage and therefore relates to its maximum theoretical production capacity under the assumption that the delivery and/or removal of at least one secondary fluid is not limiting said respective production capacity. For the samples listed in TABLE 2, 21%-42% of the envelope volume $V_{RCE}$ enclosing the reactor core element is occupied by fluid channels. For a given sized reactor core element, the value of $V_{FCZ}/V_{RCE}$ is primarily dependent on the layout arrangements of fluid channels inside all available fluid channel zones; the parameters $\phi_{FC}$, $g_{FC}$, and

TABLE 1 reactor core elements with sealing zones 105-t, h = 2 mm, and $d_{EZ}$ = 1.5 mm

| Sample Type | $\phi_{FC}$ (μm) | $g_{FC}$ (μm) | N | $CA_{RCE}$ (cm$^2$) | $SA_{FCZ}$ (cm$^2$) | $V_{FCZ}/V_{RCE}$ (%) | $SA_{FCZ}/V_{RCE}$ [m$^2$/m$^3$] | $N/N_{ST1}$ |
|---|---|---|---|---|---|---|---|---|
| ST1 | 46.5 | 18.5 | 89,024 | 4.5 | 260 | 34 | 28,900 | 1.00 |
| ST2 | 36.5 | 18.5 | 123,732 | 4.5 | 284 | 29 | 31,529 | 1.39 |
| ST3 | 26.5 | 18.5 | 185,108 | 4.5 | 308 | 23 | 34,246 | 2.08 |
| ST4 | 21.5 | 18.5 | 234,572 | 4.5 | 317 | 19 | 35,209 | 2.63 |
| ST5 | 16.5 | 18.5 | 303,712 | 4.5 | 317 | 15 | 35,215 | 3.43 |
| ST6 | 11.5 | 18.5 | 416,262 | 4.5 | 309 | 10 | 33,420 | 4.68 |
| ST10 | 41.5 | 18.5 | 153,165 | 7.1 | 399 | 29 | 28,250 | 1.72 |
| ST11 | 31.5 | 28.5 | 195,016 | 5.6 | 386 | 26 | 33,014 | 2.19 |
| ST12 | 31.5 | 18.5 | 280,823 | 9.0 | 556 | 24 | 30,878 | 3.15 |
| ST20 | 10.0 | 10.0 | 936,243 | 4.5 | 588 | 16 | 65,362 | 10.52 |
| ST21 | 5.0 | 5.0 | 3,743,586 | 4.5 | 1,176 | 16 | 130,676 | 42.05 |

TABLE 2 reactor core elements with sealing zone 105-s/105-c, h = 2 mm, and $d_{SZ}$ = 0.5 mm

| Sample Type | $\phi_{FC}$ (μm) | $g_{FC}$ (μm) | N | $CA_{RCE}$ (cm$^2$) | $SA_{FCZ}$ (cm$^2$) | $V_{FCZ}/V_{RCE}$ (%) | $SA_{FCZ}/V_{RCE}$ [m$^2$/m$^3$] | $N/N_{ST1}$ |
|---|---|---|---|---|---|---|---|---|
| ST51 | 46.5 | 18.5 | 111,303 | 4.5 | 325 | 42 | 36,132 | 1.25 |
| ST52 | 36.5 | 18.5 | 152,232 | 4.5 | 356 | 36 | 39,556 | 1.74 |
| ST53 | 26.5 | 18.5 | 232,200 | 4.5 | 387 | 29 | 42,958 | 2.61 |
| ST54 | 21.5 | 18.5 | 294,030 | 4.5 | 397 | 24 | 44,133 | 3.30 |
| ST55 | 16.5 | 18.5 | 382,998 | 4.5 | 397 | 18 | 44,118 | 4.3 |
| ST56 | 11.5 | 18.5 | 521,213 | 4.5 | 377 | 12 | 41,846 | 5.85 |
| ST60 | 41.5 | 18.5 | 191,457 | 7.1 | 499 | 37 | 35,313 | 2.15 |
| ST61 | 31.5 | 28.5 | 249.223 | 5.6 | 493 | 33 | 42,190 | 2.80 |
| ST62 | 31.5 | 18.5 | 351,029 | 9.0 | 695 | 30 | 38,598 | 3.94 |
| ST70 | 10.0 | 10.0 | 1,173,859 | 4.5 | 738 | 21 | 81,951 | 13.19 |
| ST71 | 5.0 | 5.0 | 4,690,917 | 4.5 | 1474 | 21 | 163,744 | 52.69 |

Images of actual samples ST1-ST6 and ST10-ST12 can be seen in FIG. 5. Samples ST1-ST6 and ST10-ST12 were made in accordance with the teachings of this disclosure, as discussed below in relation to FIG. 7. All these samples have a porosity of $V_P$=9200 and are made from an open-pore cellular network material with a bi-continuous tortuous phase structure as discussed below. The rectangular samples ST1-ST6, ST20 and ST21 have a maximum width $W_{RCE}$=15 mm and maximum length $L_{RCE}$=30 mm. The samples ST10 (round), ST11 (square), and ST12 (hexagonal) have a maximum width and length $W_{RCE}$=$L_{RCE}$=30 mm and a centrally located secondary fluid channel or alignment channel (depending on how a respective reactor core element is incorporated into a reactor core subcomponent 250) that has a maximum width and length of 8 mm. For the samples ST10-ST12 and ST50-62, the values and/or ratios for $SA_{RCE}$ and $V_{RCE}$ listed in TABLES 1 and 2 include the volume of $d_{EZ}$; the sum of all cross-sectional areas of any available secondary fluid channels and/or channel extrusions; and the mechanical integrity of remaining material structure filling the volume of such a reactor core element.

Equation (5c) teaches that the highest active surface area $SA_{FCZ}^{max}$ is achieved when $\phi_{FC}$=$g_{FC}$ and $\phi_{FC}$ has the smallest manufacturable value acceptable for a fluid reactor unit application incorporating such a reactor core element. The ST21, ST20, ST71, and ST70 samples are maximized for surface area for a $\phi_{FC}$=5.0 and 10.0 μm and are manufacturable with the below described manufacturing method discussed in relation to FIG. 7.

Equation (8) below teaches that under certain conditions, the theoretical maximum primary fluid flow $F_{FCZ}^{max}$ of different reactor core elements having a height h is proportional to the number N of available active fluid channels for each reactor core element. The column labeled ($N/N_{ST1}$) in TABLES 1 and 2, therefore, allows a theoretical maximum primary output fluid productivity performance comparison between the different samples ST1-ST71 relative to sample ST1.

Figure 3:
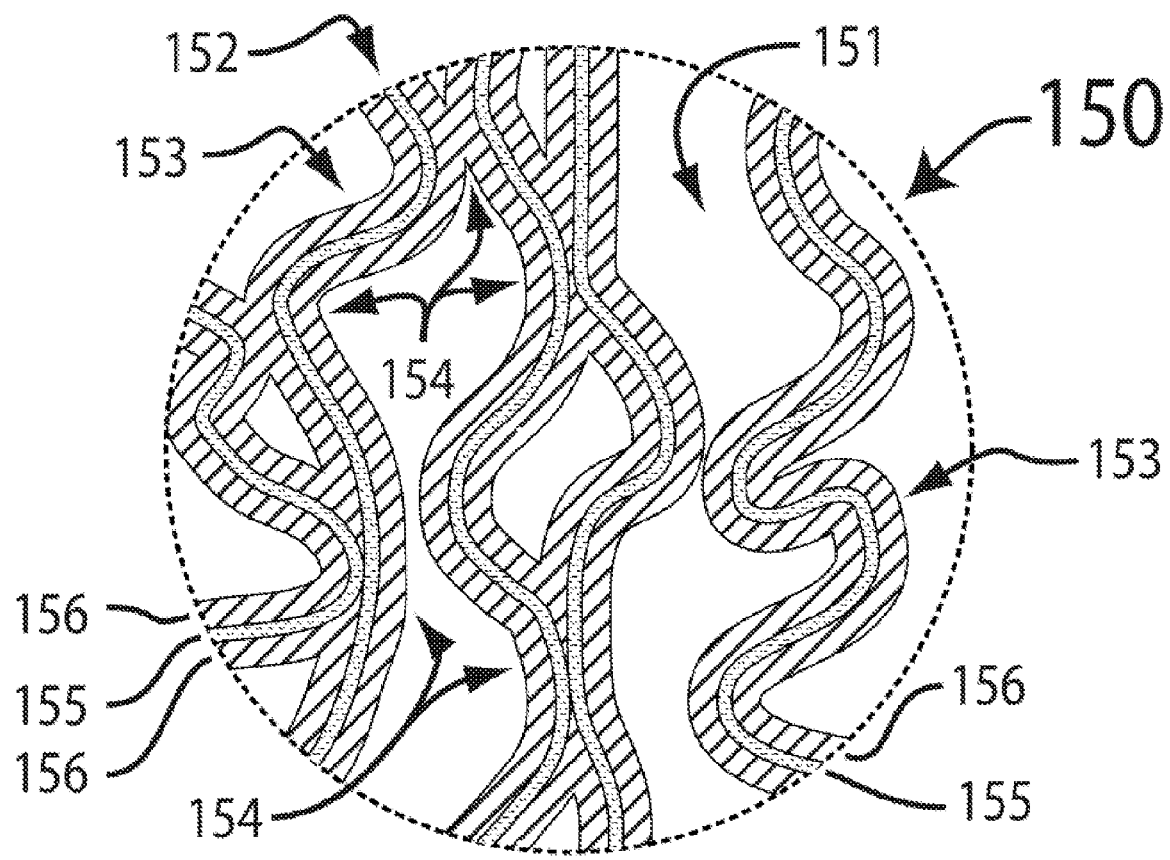
FIG. 3 shows a schematic, not-to-scale magnified view of a cross section through a tortuous, bi-continuous, open-pore cellular network material filling the bulk volume of a reactor core element.

The bulk volume of a given reactor core element is defined as the volume enclosed by sidewall(s), reactor core element input surface, and reactor core element output surface minus the volume of all extruded fluid channels and any available secondary fluid channels, notches, and channel extrusions located within the sidewalls. For all reactor core elements of this disclosure, the bulk volume is filled (as depicted in FIG. 3) with an open-pore cellular network material that has a bi-continuous tortuous phase structure including a void phase and a solid phase.

"Phase," as used in this disclosure refers to a region of material that has a substantial uniform material composition which is a distinct and spatially separated portion of a heterogenous system. The term "phase" does not imply that the material make-up a given phase is chemically homogenous, but rather implies that selective physical properties are essentially uniform throughout the material, and that these physical properties significantly differ from the physical properties of another phase within the material. Examples of such selective physical properties include density, chemical composition, electrical conductivity, structural connectiveness, and structural arrangements.

Structural arrangements and make-up of a given solid material or phase can be observed, for example, with a Scanning Electron Microscope (SEM) and/or other characterization equipment as known to those skilled in the art by looking at a material sample in either top, tilted and/or cross-sectional view. The local chemical composition of material elements forming a solid phase and its material consistency or compositional change along a scan line or scan region can, for example, be analyzed with an EDX and/or XRD system. With these and/or other characterization tools one can, for example, check (i) if a given porous solid phase includes one or more individual physically separated elements; (ii) if these individual elements are all made from one or from more than one type of material; (iii) if all these elements have a similar structural shape; (iv) if there is a mixture of elements that have similar chemical composition but have a different shapes (for example, filaments, tubes or platelets, and so on); and (v) if a given solid phase includes at least one large continuous single element (for example, a single or multi layered skin of an open porous cellular network structure that has optionally subsequently been removed).

Smaller elements of a solid material phase are also referred to herein as ligaments. Using diagnostic tools, one can further investigate if any observed ligaments are (i) mechanically intertwined, (ii) locally structurally connected and/or attracted to each other only by Van der Waal forces, and/or (iii) mechanically spot-welded to each other in selected spatially isolated locations. Additional investigations can show if these ligaments are themselves homogeneous or include multiple material layers of one or more materials surrounding a common solid or hollow core material (for example, like a tree ring pattern). Further analysis can show if a given solid material includes multiple types of ligaments with each of the ligament types having substantially a 1-D, 2-D, or 3-D structure, as will be discussed more below. It can further show from what material or materials (homogeneous or non-homogeneous mixtures of material and/or material layers) each ligament type is made. If there was a starting material that was originally present when the ligament type started to form, diagnostic tools can detect whether such starting material is still present or if it has since been removed by means known to those skilled in the art (for example with a chemically selective liquid or gas material removal processes). Removing such starting material creates a second void phase that in itself can be continuous or non-continuous, but is typically much smaller than a (primary) void phase or solid phase.

"Continuous," as used herein, generally refers to a phase wherein all points are directly mechanically connected; therefore, for any two points within a continuous phase, there exists a path which connects the two points without leaving the phase. "Bi-continuous," as used herein, refers to a material containing two separate phases such that each phase is continuous, and in which the two phases are interpenetrating, such that it is impossible to separate the two structures without destroying at least one of them.

"Tortuous," as used herein, refers to a phase that requires numerous and frequent changes in direction when moving from one point in a phase to another so that, on average, the shortest line physically connecting two points in a phase, while traveling only inside the phase volume, is much longer than the line of sight distance between the two points.

The transport of one or more secondary fluids through a simple reactor core element is controlled in part by the void phase which has a volume porosity $V_P$, defined as the ratio of the total volume of the void phase to the volume of the open-pore cellular network material, where the volume of the open-pore cellular network material is defined as the bulk volume of the reactor core element. One of the main purposes of the void phase in this disclosure is secondary fluid transport between the sidewalls and the secondary fluid external input surface and/or secondary fluid external output surface. The pore size distribution of the void phase is relevant for the secondary fluid transport. The pore size distribution of the sidewalls is relevant to keep at least one component of the primary input fluid contained inside the fluid channels, as will be further discussed below. In embodiments, these pore size distributions can either be substantially uniform or non-uniform and can either be symmetrical or asymmetrical, with the longer direction of the pores being typically aligned parallel or perpendicular to the long axis of respective fluid channels. In embodiments having an asymmetric pore size distribution for both the sidewalls and the open-pore cellular network material, the average pore size dimension pi in a direction perpendicular to the fluid channels flow direction is about 2 to over about 10 times smaller than the average pore size dimension $p_{\parallel}$ parallel to the fluid channels flow direction (see FIG. 6A).

The solid phase is responsible for the mechanical strength of the open-pore cellular network material and, thus, of the free standing, i.e. substrate support-free, reactor core elements of this disclosure. It also provides mechanical support for an optional thin membrane film grown and/or deposited onto the primary fluid contact surface, or at least over the sidewalls, of a reactor core element, as will be discussed further below. Sufficient mechanical strength for the free standing open-pore cellular network material facilitates subsequent fluid reactor unit manufacturing and application dependent operation for extended times. In embodiments, a particular solid phase is selected for its ability to mechanically survive a drying process step of a respective reactor core element. Such a liquid drying process step may be necessary, for example, due to exposure of a reactor core element to a liquid during its manufacturing process, or afterwards during its incorporation into a reactor core subcomponent, reactor core, or fluid reactor unit, or after a primary fluid or secondary fluid stops flowing into a fluid reactor unit incorporating such a reactor core element. The solid volume fraction $V_S=1-V_P$ of the solid phase fills out the rest of the volume of the reactor core element except for regions where fluid channels and optional secondary fluid channels, notches, and channel extrusions are located.

In certain circumstances, the solid phase can notably contribute to the flow resistance and thus the pressure drop for the secondary fluid flow through an open-pore cellular network material. For many fluid reactor unit applications (especially for gaseous secondary fluids), open-pore cellular network materials can be made sufficiently mechanically strong even with $V_S \ll V_P$ to minimize such secondary fluid flow resistance. In embodiments, $V_S<20\%$, <10%, or <5%. All samples shown in FIG. 5 have $V_S \approx 8\%$. In particular, when a liquid secondary fluid is used, the solid phase can significantly add to the flow resistance/pressure drop of the secondary fluid flow through the open-pore cellular network material, i.e. through the reactor core element, whether the secondary fluid originates at a sidewall or at some other portion of the secondary fluid external contact surface (e.g., the sidewalls of secondary fluid channels and/or channel extrusions). Such a secondary fluid flow resistance depends in part on if there is a "philic" or "phobic" affinity for the liquid-based secondary fluid and the most outer surface of the solid phase. Depending on the intended application of a reactor core element, i.e. on the chemical nature of any relevant secondary fluids, in embodiments, the whole solid phase forming the open-pore cellular network material of the respective reactor core element is conformally surface treated to make it more "philic" for any secondary fluids that need to travel through it. In embodiments, such a treatment is done during the manufacturing phase of the reactor core element, and in other embodiments, subsequent to it, for example after the reactor core element has been incorporated into a fluid reactor unit. Such surface-only treatments can be selected from the non-intended to be limiting group of treatments of the solid phase including (i) up to a few monolayers thick conformal coating; (ii) a 1-100 nm thick conformal film coating; (iii) a liquid-based acid or base (for example HCl, $HNO_3$, $H_2SO_4$, chlorosulfonic acid, HF, NaOH, KOH, mixtures thereof, etc.) soaking and subsequent drying; (iv) a gas phase exposure (HCl, $Cl_2$, HF, $O_2$, CO, $CO_2$, Et-OH, KOH, organo-silanes, HMDS, PFOS, mixtures thereof) treatment with or without heat and/or plasma, wherein such treatment can occur below, at, or above atmospheric process conditions; and/or (v) combinations thereof.

Other surface treatments, sometimes referred to as coatings herein, can include a CVD based deposition of a thin polymeric film. For example, to make a carbon-based solid phase more hydrophilic, $HNO_3$, $H_2SO_4$, HF liquid acid bath, or a gas phase surface oxidation process can be used to create defects and/or dangling bonds at or near its surface, thereby creating a more hydrophilic contact surface for water-based liquid secondary fluid to interact with. Oxygen-based reactive ion etching or KOH liquid acid-based process, in general will also cause the as-grown somewhat hydrophobic open-pore cellular network material 150 to become more hydrophilic, which in turn aids in the subsequent liquid-based or acid-based separation of the open-pore cellular network material 150 from a growth support wafer. However, once the surface layer of the solid phase gets attacked, thus creating defects, such damages cannot sufficiently be reversed, even if such structures are annealed at 900° C. under a pure $H_2$ atmosphere for 30 minutes. In embodiments, a much high temperature $T_A$ annealing process for an extended time under inert and/or hydrogen atmosphere with $T_A>2000°$ C., or $T_A>2500°$ C., for 30 minutes to 900 minutes is used to heal the carbon surface layer defects (recrystallizing it and graphitizing it over time, with higher temperatures requiring shorter times) thus turning the defective and at least partially hydrophilic open-pore cellular network material as separated from the growth substrate into a more hydrophobic open-pore cellular network material thereafter.

FIG. 3 schematically depicts that the solid phase 152 of an open-pore cellular network material 150 of this disclosure includes ligaments 153 (also called herein "struts") that are mechanically linked (also called herein "interlinked," "interconnected," or "connected") by welds 154 (also called herein "weldments," "spot welds," "material welds," or "joints").

Figure 4:
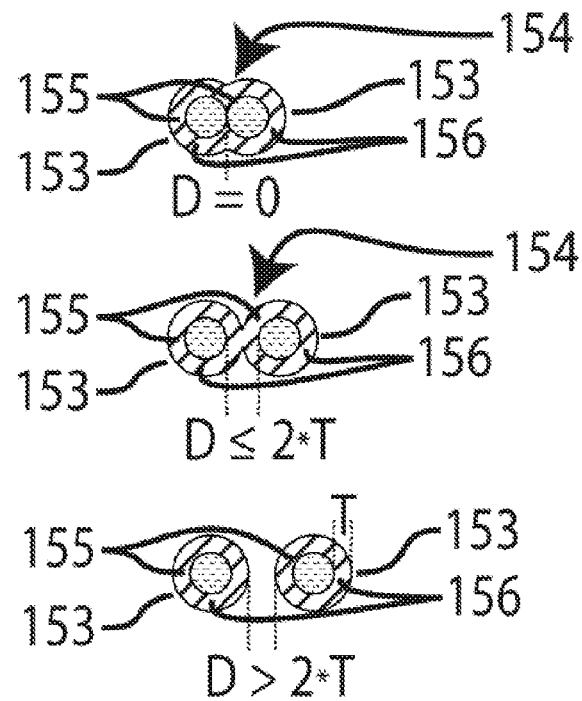
FIG. 4 shows a series of two ligament preforms with a conformal coating layer.

FIG. 3 and FIG. 4 depict ligament preforms 155 of the solid phase 152 that are overcoated substantially uniformly with a conformal coating layer 156 having an average thickness T. The conformal coating layer may include multiple coating layers applied to the ligament preforms 155. This conformal coating layer 156 increases, on average, the starting width of each such ligament preform 155 by 2*T. The underlaying ligament preforms 155, together with the subsequently applied conformal coating layer 156, form the ligaments 153. As FIGS. 3 and 4 depict, wherever the local line of sight distance D between two adjacent ligament preforms 155 is D≤2*T, the two ligaments 153 locally weld (spot weld) together, thereby forming a material weld 154. The more tortuous (bent, crinkled, corkscrew-like, mechanically intertwined, etc.) such ligament preforms 155 are, the more often they cross each other's path or approach each other sufficiently close to form a local material weld 154. The more often they mechanically weld together and/or the thicker the ligaments 153, the mechanically stronger the open-pore cellular network material 150 becomes. Also, the thicker such a chosen conformal material layer 156 is, the more material welds 154 get formed and the more mechanically strong such a solid phase 151 of the open-pore cellular network material 150 becomes and the more densified (denser) it becomes.

In embodiments, and as shown in FIGS. 3 and 4, ligament preforms 155 may be substantially 1-dimensional (1-D) shaped loose objects that optionally are only connected by Van der Waal forces. Loosely agglomerated objects with a high aspect ratio (with average length/width≥25) are one of the ligament preform 155 embodiments of this disclosure. Such ligament preforms 155 can include single wall, few wall, or multiwall type carbon nanotubes, and in particular vertical aligned carbon nanotubes and Si nanowires.

In embodiments, ligament preforms 155 have at least one dimension in the nanometer range, i.e. less than 1 μm, less than 500 nm, less than 100 nm, or less than 25 nm and include solid, hollow, or porous 1D, 2-D, and/or 3-D like objects that have the shape of wires, filaments, tubes, posts, pillars, flakes, disks, wrinkled sheets, partial round or cuboid shaped hollow partial "egg-shell" like structures, particles with spikes attached to it, and furcated and/or dendritic nanostructures. Such ligament preforms 155 are typically not mechanically connected when formed or after they have been rearranged into a suitable starting shape, for example in a mold. Such ligament preforms 155 may be made from materials selected from the non-intended to be limiting material group of carbon, metals, metal alloys, semiconductors, metal oxides, metals or metal alloy cores with oxide surface skin layers, metal nitrides, metal carbides, polymers, and/or combinations or layered structures thereof.

The 1-D like ligament preforms 155 may be in the form of carbon nanotubes, nanowires, carbon fibers, or electrospun solid or hollow fibers having an organic, inorganic, or mixed organic and inorganic composition. Ligament preforms 155 having an organic (polymer) or mixed inorganic and organic composition can optionally first be converted into a carbon fiber or tube preform through slow annealing in inert and/or hydrogen-based atmospheres, as known to those skilled in the art.

The 2-D like thin sheet-like objects may optionally be heavily wrinkled, have a high aspect ratio between the average length and thickness of these two-dimensional sheets (i.e. >25), and/or have at least a thickness in the nm range. Such 2-D like objects are commercially available as graphene-like thin nano-platelets (sold by XG Sciences and others) and graphene-oxide powders (sold by Sigma-Aldrich) that are later reduced to graphene-like carbon platelets or other exfoliated two-dimensional materials (as sold by Sigma-Aldrich and others).

The solid and/or hollow 3-D shaped objects are typically sold as powders and can be round, spiky (Ni powders as sold by VALE), elongated, and/or partially agglomerated, forming dendritic, tentacle-like, or spiky structures with nm size diameters. Examples of such 3-D shaped agglomerated particles that may be used as ligament preforms 155 include acetylene carbon black (sold by Cabot Corporation); colloidal $SiO_2$; colloidal $Al_2O_3$ (sold by Sigma-Aldrich); and 50-100 nm cube-shaped egg-shell type nanosized powders, like the 3-D graphene powder (sold by Graphene Technologies) or nm sized metal powders, i.e. Ti based.

In further embodiments of this disclosure, 1-D, 2-D and/or 3D objects are mixed together to form a loosely connected body of ligament preforms 155 and subsequently are coated with a conformal material layer 156, thus forming an open-pore cellular network material 150.

In embodiments, heat and/or a $H_2$ treatment (to de-oxidize, for example, a surface layer of a ligament preform 155) is applied to the arranged body of ligament preforms 155 so that the ligament preforms 155 locally sinter (weld) together wherever they are in intimate contact to each other, as can easily be done with ligament preforms 155 made from Ti, Ni, or other sinterable metals below the melting point of the metallic ligament preforms 155, thus making an open-pore cellular network material 150. In other embodiments, a metal-based ligament preform 155 arrangement is overcoated with at least one conformal layer 156 that is thick and strong enough to withstand a subsequent wet or dry etching process to remove the metal-based ligament preform 155.

In some instances, at least some of these ligament preforms 155 (for example, vertical aligned carbon nanotubes or Si nanowires) can experience attractive Van der Waal forces between them, especially when they are freshly manufactured and still in a very clean and pristine form with little surface layer contamination, i.e. before they adsorb a few monolayers of another material (for example volatile organic compounds (VOCs) or $H_2O$) on their other surface. These attraction forces have a $\sim 1/D^6$ dependency on the closest distance D between the ligament preforms 155 and are not a result of any chemical electronic bond. Due to these Van der Waal forces, whenever and wherever two such 1-D objects locally touch each other, they can locally, on a nanometer scale, get attracted to each other and thereby get stuck together. Bare carbon nanotube forests, patterned in a particular manner when grown on a substrate, held together solely by Van der Waals forces are not very stiff; therefore, if a load is applied to the forests, they may deform, thus destroying at least part of the pattern in which they were manufactured. So, if their spatial arrangement is minimally changed after they have been grown on a substrate in the form of a special pattern, then such carbon nanotubes or nanotubes can get stuck to each other like Velcro due to a small side load, thereby destroying at least some area of the previously manufactured pattern.

A suitable wetting/drying test with all relevant liquids can prove, for example, if an apparently bonded porous open cellular network material candidate is suitable as an open-pore cellular network material 150 for this disclosure or not, i.e. if the solid part of such a material forms a continuous solid phase 152 that is mechanically strong enough to be usable in a reactor core element to be later incorporated in a fluid reactor unit of this disclosure.

In embodiments, a loose agglomeration of 1D, 2D, and/or 3D type ligament preforms 155 is localized temporarily inside a suitably shaped gas porous mold or holder. Suitable porous holders or molds can be made out of copper foam, nickel foam, other gas porous materials, and/or a combination of solid and gas porous materials as known to those skilled in the art, with the gas porous materials acting as "windows" that (i) have sufficiently small pore sizes to contain the loose ligaments preforms 155, (ii) are otherwise as open as practical to minimize any reductions of flows of CVD precursor gases into and out of the mold, (iii) are otherwise inert (non-catalytically active) during a CVD coating process resulting in targeted conformal material layer 156, and (iv) are easily subsequently removable as known to those skilled in the art, for example by wet etching or dry etching methods (defined herein as selective corrosive process gas exposure at sufficiently high temperatures chosen to gasify the porous mold material at a reasonable rate without substantially etching/gasifying an open-pore cellular network material 150 located inside the mold). Such holders/molds may be suitably filled with a such loose ligament preform 155 using methods known to those skilled in the art: for example, with the assistance of vibratory and/or ultrasonic shaking and/or a vacuum infiltration process assist.

In embodiments, the mold has the shape of the sidewall 129. In other embodiments, the mold is larger than the reactor core element 100. In embodiments, the fluid channels 104 and any optional secondary fluid channels 132, notches 117 (where the notches are channels), and channel extrusions 119 can be formed (i) before the CVD coating process resulting in the conformal material layer 156 (hereinafter synonymously called an infiltration process), (ii) after the infiltration process resulting in the conformal material layer 156, or (iii) after forming the welds 154 without the use of a conformal layer 156 deposition process step (e.g. if a sintering type processes is used instead). In embodiments, the mold contains sacrificial inserts (for example metal wires, metal posts and/or hollow metal tubes) positioned where the fluid channels 104 and/or other channels 117, 119, and/or 132 are desired to be located for one or more reactor core elements 100 which are later removable either prior, after, or at the same time as the mold is removed.

In embodiments, the subsequent removal of the open-pore cellular network material 150 material from the mold results in a material block that can be further shaped into the desired reactor core element 100 shape by means know to the skilled in the arts (drilling, milling, stamping, reactive ion etching through a mask, etc.). Additional extrusion features and/or sidewalls 129, secondary fluid channels 132, notches 117, channel extrusions 119, and/or other shaped cutouts can be created as needed.

In embodiments, at least one process is applied to conformally coat a loose arrangement of ligament preforms 155, with a conformal material layer 156 (for example, containing at least one carbon, a metal, an oxide and/or a nitride thin film layer) thereby forming material welds 154 wherever the ligament preforms 155 fulfill the condition D≤2*T and thus forming an open-pore cellular network material 150 with a bi-continuous tortuous phase structure.

Other suitable techniques to conformally coat many substrates with many types of different coatings, including conformal CVD coatings. In embodiments, the conformal material layer 156 is applied with one or more low pressure, atmospheric, and/or high-pressure Chemical Vapor Deposition (CVD) process steps utilizing sufficiently low pressure or precursor gas dilution to achieve the desired infiltration level uniformity. In other embodiments, the conformal coating layer 156 is manufactured by (i) soaking with a liquid carbon precursor (for example, diluted carbon fiber resin and/or polymer dispersion) a mold filled with an agglomerate of loosely bonded ligament preforms 155, (ii) pressing it to the desired density and height, and (iii) subsequently heat treating it under an inert gas environment to convert the liquid carbon precursor coated film into a conformal carbon film, thus forming welds 154. If needed, multiple such coatings of one or more material types can be applied until the desired thickness T is achieved for the conformal material layer 156.

Liquid-based coating methods for the deposition of at least one conformal coating layer 156, for example electro plating or electroless plating, may also be used, but they typically are less likely to produce uniform coating thickness throughout the open-pore cellular network material 150, compared to the gas phase processes which are more suitable for conformally coating tortuous porous materials having nano-sized pore diameters and which enable the manufacturing of open-pore cellular network material 150 having a thicknesses h>1 mm.

In embodiments, the precursor ligaments 155 are carbon-based and the coating 156 is also carbon-based. Patterned vertical aligned carbon nanotube forest may be infiltrated with a carbon, Si, SiN, and/or $SiO_2$ film by an atmospheric or low-pressure CVD based method and/or converting one material film into another (for example, oxidizing it thereafter). The application of a thin conformal carbon coating after a patterned carbon nanotube structure has been grown on a patterned catalyst Si wafer may be performed at an atmospheric 900° C. temperature CVD process utilizing $H_2$ and $C_2H_4$ at a ratio of from about 0.8:1 to about 1:6:1, or typically 1.3:1. The thickness of the conformal coating T is primarily controlled by time once the process gas ratios have been optimized for a given CVD infiltration deposition system.

In embodiments, growth substrates for making patterned catalyst substrates are Si or oxidized Si wafers optionally having at least a fine polishing finish on their growth side and which obtain their catalytic film pattern through a standard photolithography-based lift-off process, as known to those skilled in the art. In other embodiments, any other vertical aligned carbon nanotube growth process and conformal coating layer deposition process-compatible support structure can alternatively be used instead of a Si wafer as growth substrate. For example, a quartz, sapphire, a metal or metal alloy wafer, or a metal or metal alloy foil (for example, a stainless-steel alloy) can be used as long as a suitable patterned catalytic film can be deposited or created on its top surface by any appropriate means. In embodiments, photolithography-based lift-off, printing, laser assisted deposition and/or laser assisted ablation process steps and any infiltration process-compatible substrates are considered for manufacturing patterned catalyst substrates as long as they can fulfill the resolution requirements for all the extruded features of a reactor core element that is first grown and then removed from such a starting substrate.

In embodiments, a 5-100 nm thick $Al_2O_3$ film is deposited over a patterned polymer film carbon nanotube catalyst film stack followed by a 0.5-5 nm thick Fe film, thus forming a basic carbon nanotube catalyst film stack. After the catalyst film stack deposition, the thus prepared growth substrates move to a final stripping process that removes any remaining patterned polymer film covering the fluid channels and any other regions on the wafer where the presence of open-pore cellular network material was not wanted, e.g., outside the edge 109a, any optional secondary fluid channels, notches, and/or channel extrusions. This final photolithograph process step exposes the patterned catalytic Fe or $Fe/Al_2O_3$ film stack, thus creating the regions from which vertical aligned carbon nanotube forest structures grow substantially vertically from the patterned catalyst growth substrate. As known to those skilled in the art, the presence of the $Al_2O_3$ layer allows the growing of taller patterned Vertical Aligned Carbon Nanotube (VACNT) structures and thus of taller reactor core element precursors than without it, e.g., typically with a height h<0.5 mm in one hour or less.

First, patterned vertical aligned carbon nanotube structures can be grown on Si wafers with h up to 5 mm for reactor core elements having fluid channel diameters $\phi_{FC}$ from about 100 µm down to about 4 µm and a $g_{FC}$ from about 150 µm down to about 5 µm. These vertical aligned carbon nanotube structures can then then substantially uniformly infiltrated with a carbon film, with a thickness T from about 2 nm up to about 30 nm, thus creating reactor core element precursor structures with different mechanical strengths. This forms a ligament having an average diameter up to about 10-80 nm (typically about 20-25 nm), where the starting ligament preform is in the form of loosely bound vertical aligned carbon nanotubes having an average thickness of about 8-12 nm.

For many fluid reactor applications, a conformal material layer is applied with a thickness T in the 1 nm to 100 nm range, 2 nm to 50 nm range, or 3 to 20 nm range, depending, amongst other factors, on (i) the fluid channel diameter $\phi_{FC}$; (ii) the thickness, tortuosity, and stiffness of the ligament preforms; (iii) the average distance between the ligament preforms; (iv) the average separation between the welds; (v) the desired $V_P$ and mechanical strength of the resulting open-pore cellular network material; (vi) the total number of coating layers to be applied; and (vii) the targeted total thickness T of the conformal material layer. In embodiments, a CVD process can deposit one or more thin film coatings of the same material as the ligament preforms or one or more films of different material.

In embodiments, for a fluid reactor application incorporating a reactor core element, an open-pore cellular network material is selected to first provide a sufficient low flow resistance between the fluid channel primary fluid contact surface and the secondary fluid external contact surface for up to the maximum intended secondary fluid flow range, i.e. with an acceptable range of $V_P$, pore side distribution, and "philicity" for the outer surface of the solid phase. The open-pore cellular network material is further selected to be mechanically strong enough to be free standing on its own (based on the physical size of the chosen targeted reactor core element, i.e. its height, width and length or diameter) and selected to be strong enough that it can be gripped and moved by suitable mechanical grippers, including hands or vacuum grippers, without the aid of a solid, porous, flexible or rigid temporary substrate support, thereby enabling the support-less (also called substrate-free) manipulation and utilization of such a material as a reactor core element. Such an open-pore cellular network material selection, when possible for a given targeted fluid reactor application, makes a fluid reactor much more manufacturable by (i) helping to increase its production yield, thereby lowering its average production cost, (ii) potentially extending its usable lifetime, (iii) increasing its robustness against process parameter variations during its first-time utilization phase, and/or (iv) enabling repeated utilizations.

Optionally, the open-pore cellular network material is further selected to be strong enough to survive the fluid flow introduction and fluid flow of any primary fluids and secondary fluids into and out of such a reactor core element for at least the intended flow duration for which such a reactor core element was designed and made. If multiple open-pore cellular network material types are available for a given fluid reactor application, cost and yield considerations come into play to help further narrow down the options. In embodiments, the reactor core element is made from a selected open-pore cellular network material chosen to be strong enough to also mechanically survive, at least once, the total removal of any fluids from its body. Such removal of fluids may be necessary, for example, when one, two, or more liquid fluids are used to form an antithrombotic coating on at least part of the primary fluid contact surface, or during a manufacturing process step of the reactor core element, as discussed further below in relationship to FIG. 7. In embodiments, the selected open-pore cellular network material survives all the capillary forces pulling on any of its ligaments during a drying phase of liquid based primary input fluids from all of its fluid channels. In other embodiments, the selected open-pore cellular network material also survives the drying after having been soaked in water and/or selected organic solvents (ethanol, methanol, butane, hexane, acetone, oil, or mixtures thereof). For example, the samples ST1-ST6 and ST10-ST12 shown in FIG. 5 all survived even an acetone wetting test (local acetone wetting followed immediately by an air-drying step) despite having only a small solid phase volume porosity, i.e. $V_S \approx 8\%$.

The selected open-pore cellular network material can either have isotropic or anisotropic pore size distribution in the void phase and related isotropic or anisotropic mechanical strength properties. In embodiments, an anisotropic pore size distribution is used since, typically for the same secondary fluid flow rate, better mechanical filtering or primary fluid component confinement properties and/or hydrophobic properties can ultimately be obtained with such an asymmetric pore structure as long as it is mechanically strong enough for the targeted application. Whether the narrower pore distribution of an open-pore cellular network material is parallel or perpendicular to the flow direction of the fluid channels is typically not important for the maximum fluid reactor application dependent flow rate of a reactor core element. The alignment direction of these pores typically results in a corresponding influence asymmetric fracture strength and, thus, can affect the mechanical handleability and/or probability of surviving a liquid fluid exposure and subsequent drying phase manufacturing process step of a reactor core element. For example, if 1-D shaped nanofibers/tubes/filaments are used to form an open-pore cellular network material, their overall average alignment direction in relation to one another results in a similar alignment of the resulting pore size distribution. If vertically aligned carbon nanotubes are chosen as ligament preforms, the narrow pore directions will be perpendicular to the main alignment direction of the fluid channels, as shown in FIG. 6A.

FIG. 5 shows a photograph of multiple type of substrate-free reactor core element 100 samples made with an open-pore cellular network material 150 in accordance with embodiments of this disclosure with $V_P \approx 92\%$ making it robust enough to survive water, ethanol, and even acetone soaking/drying events and strong enough to make it easily handleable with human hands, as well as with robotic suction cups and/or pressure driven grippers for mass production pick and place operations aided by optional image processing for visual feedback. Some of these rectangular samples have different semicircular notches 117 (vertical semi-circular extrusions with a width of 100 µm along sidewall 129); these notches 117 can act as ID markers, allowing the model type of a sample to be easily recognized by eye or with a digital camera showing a magnified view (by visual identification and/or image processing). The round sample ST10 has multiple notches 117 along its sidewall 129 to allow a rotation specific part orientation, when desired. In embodiments, by using a minimum separation of at least about 20-200 µm between two neighboring reactor core element precursor samples on the catalyst support substrate, and by utilizing notches 117 and protrusions 118 as ID markers, multiple of the same and/or different reactor core element precursor sample types can be manufactured simultaneously on a single substrate before being removed for further processing. More details about these samples are listed in TABLE 1. In embodiments, to make the samples in FIG. 5, twelve rectangular reactor core element precursor samples having the outer dimensions of 15 mm×30 mm (i.e. of the reactor core element samples ST1-ST6 or ST20-ST21) were grown simultaneously using a conventional 4" Si wafers as a temporary growth substrate and such reactor core element precursor samples were 100 µm spaced apart, thus maximizing the usable "real estate."

The optional use of notches 117 and protrusions 118 as ID markers for reactor core element parts facilitates the sorting of the different types of reactor core elements. Additionally, the ID markers aid in optimizing the quality control and/or yield of some of the manufacturing process steps. In embodiments, reactor core elements 100 that have sealing zones of type 105-s or 105-c have no notches 117 or protrusions 118, thus providing a notch free sidewall 129 that is smooth and easier to side seal. Alternatively, such reactor core elements 100 with type 105-s or 105-c sealing zones may only have rounded corner notches 117 that may also help make the sidewall 129 easier to side and/or corner seal.

Figure 6A:
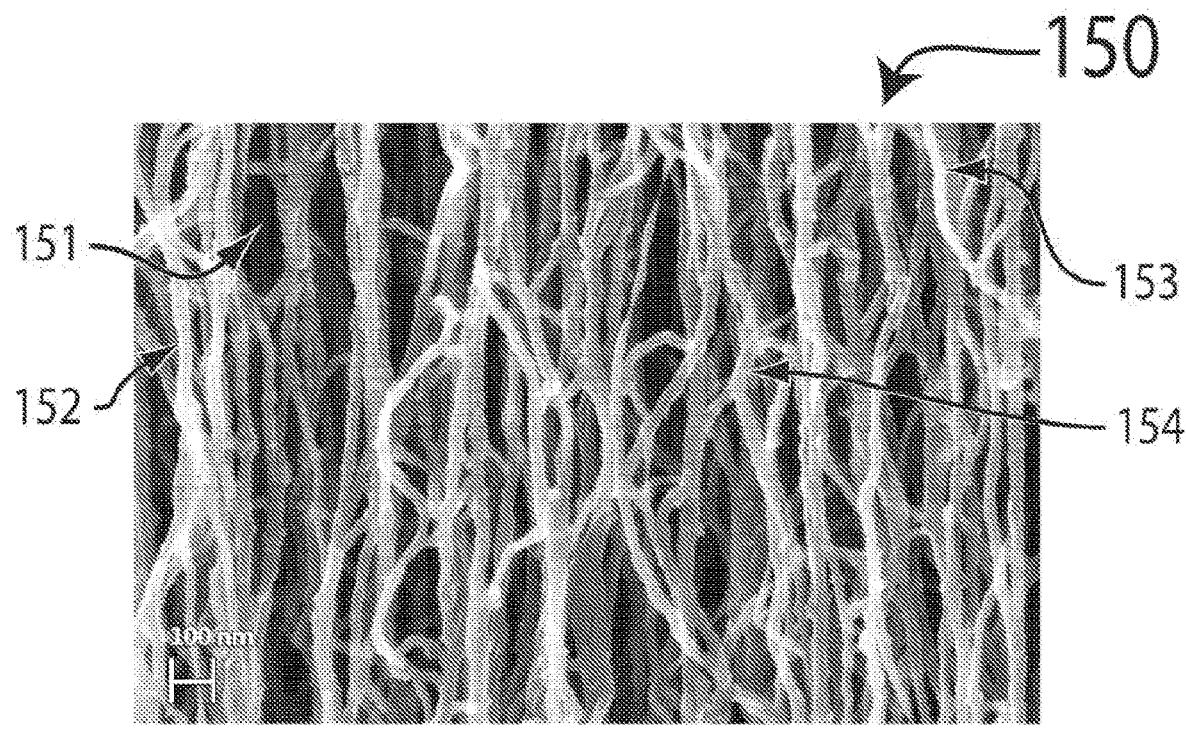
FIG. 6A shows a 150K times magnified SEM image of the middle cross section of a reactor core element sample of the type ST12.

FIG. 6A shows a 150K times magnified SEM image of the nanostructure of the open-pore cellular network material 150 used for all reactor core element 100 samples shown in FIG. 5 (specifically of sample ST12), allowing to visualize its asymmetric pore structure with $p_\perp \approx 20\text{-}50$ nm and $p_\parallel \approx 200\text{-}500$ nm. It demonstrates, in particular, that the open-pore cellular network material 150 with a bi-continuous tortuous phase has a "mangrove forest type" asymmetric void structure and contains a continuous solid phase 152 that includes a carbon coated (infiltrated) vertical aligned carbon nanotube forest, which includes "spot welded" ligaments 153 that have an average diameter of $\approx 18\text{-}25$ nm. Since the ligament preforms 155, which are the precursor to the solid phase 152 material, are loosely bonded (by Van der Waal forces) and somewhat mechanically intertwined carbon nanotubes with a diameter of 8-12 nm, the average thickness of the conformal (carbon) coating 156 is T≅4-6 nm, resulting in ligaments 153 with an average thickness of 20-25 nm.

Figure 6B:
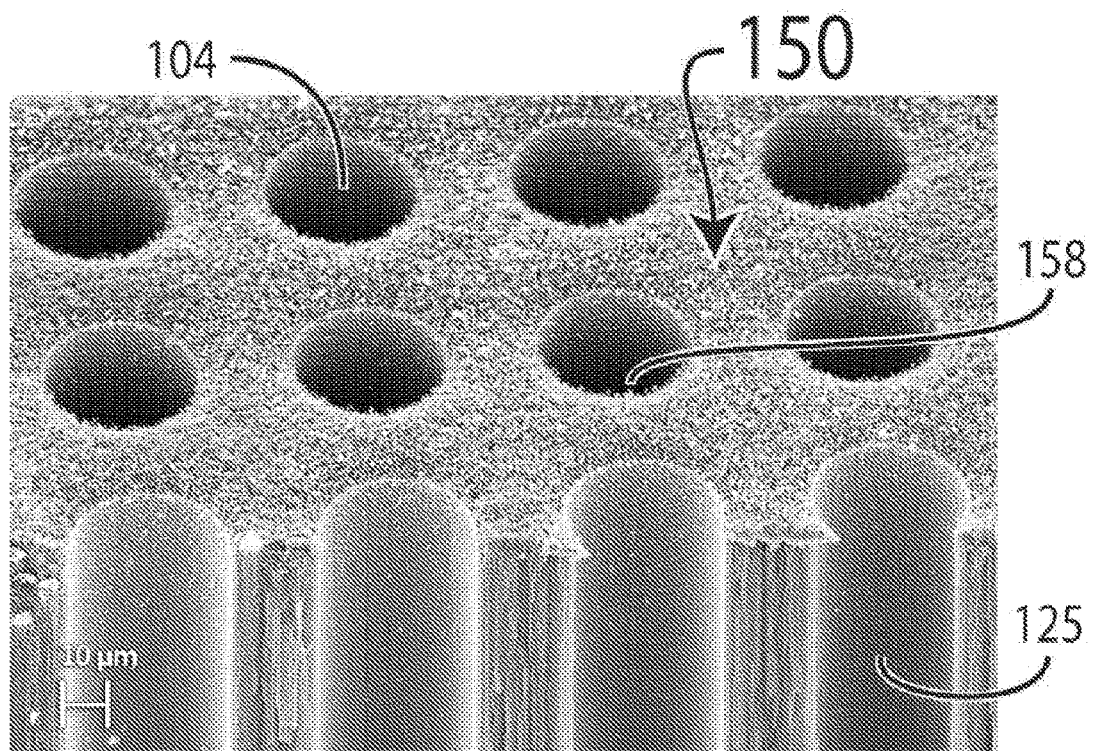
FIG. 6B shows a 1.5K times magnified SEM image of the top and side view of a reactor core element sample of the type ST12 broken apart.
Figure 6C:
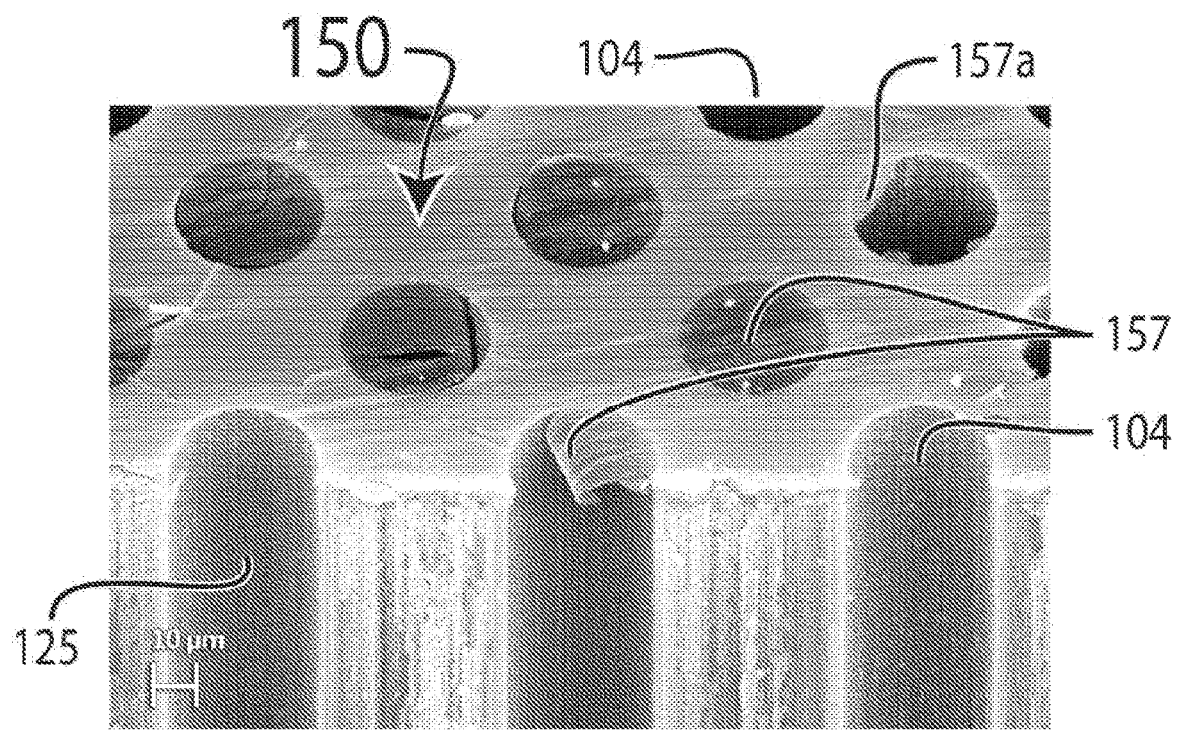
FIG. 6C shows a 1.5K times magnified SEM image of the bottom and side view of a reactor core element sample of the type ST12 broken apart, where the reactor core element is made without process step 181 of FIG. 7.
Figure 6D:
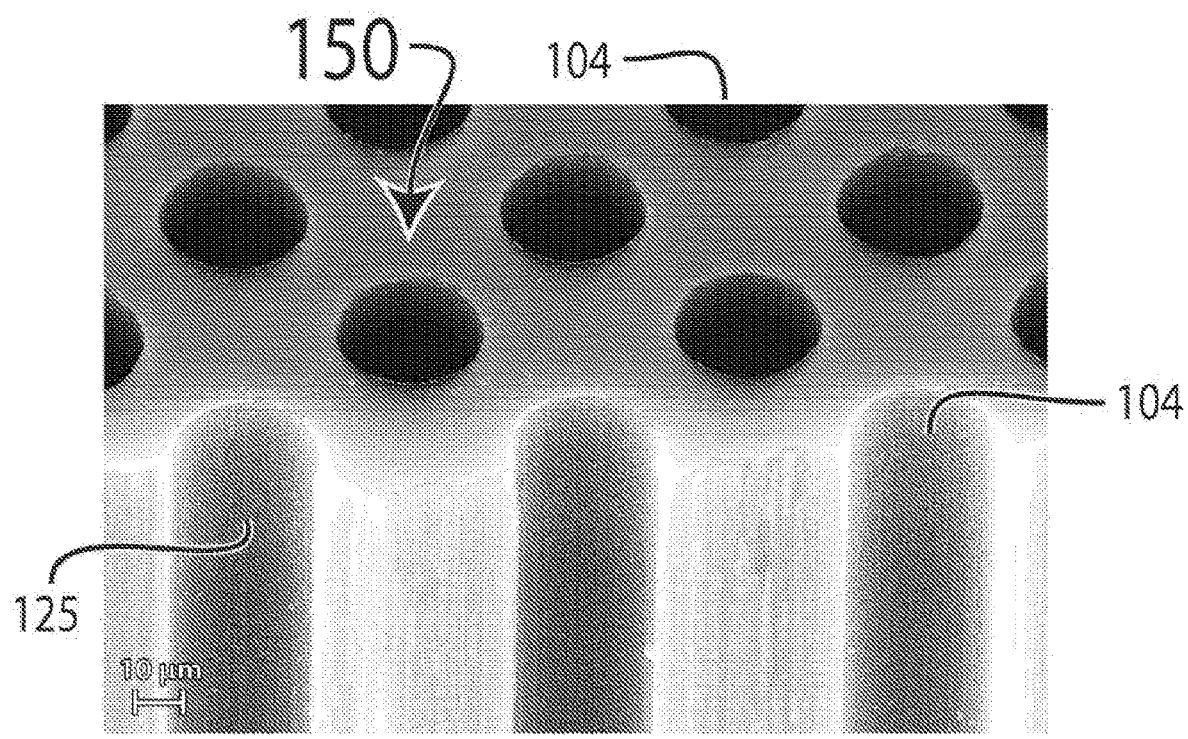
FIG. 6D shows a 1.5K times magnified SEM image of the bottom and side view of a reactor core element sample of the type ST12 broken apart, where the reactor core element is made with process step 181 of FIG. 7.

FIGS. 6B, 6C, and 6D show a 1.5K times magnified SEM image of the side view as well as a partial top (6B) and bottom (6C and 6D) view of a cut reactor core element sample of the type ST12 having fluid channels 104 with a fluid channel diameter $\phi_{FC} \approx 31.5$ μm. FIGS. 6B, 6C, and 6D show a side view of the cut open reactor core element 100 with the sidewall 125 of the fluid channels 104 and the material 150 between them. FIG. 6C and FIG. 6D also show the bottom view of the fluid channels 104 from a reactor core element 100 sample (i.e. from its flat side) of the type ST12 that was made without (6C) and with (6D) the manufacturing process step 181 listed in FIG. 7. The floor layer 157 is essentially a conformal coating 156 of the growth substrate in the catalyst free areas, e.g. the bottom cross sectional area of fluid channels 104 (and of any other perforations), and therefore has substantially the same thickness, e.g. T≅4-6 nm, and is made of the same material composition as the conformal layer 156. Despite this floor layer 157 being so thin, it is typically also very strong (depending on the strength and process conditions of the conformal coating 156). For the types of reactor core element 100 samples shown in FIG. 5, the floor layer is an ultrathin carbon film that is very strong for its mass and has a multilayer graphene-like (or hybrid graphene/amorphous film) strength to it. A partially leftover floor layer 157a is visible in FIG. 6C for most fluid channels 104.

Figure 7:
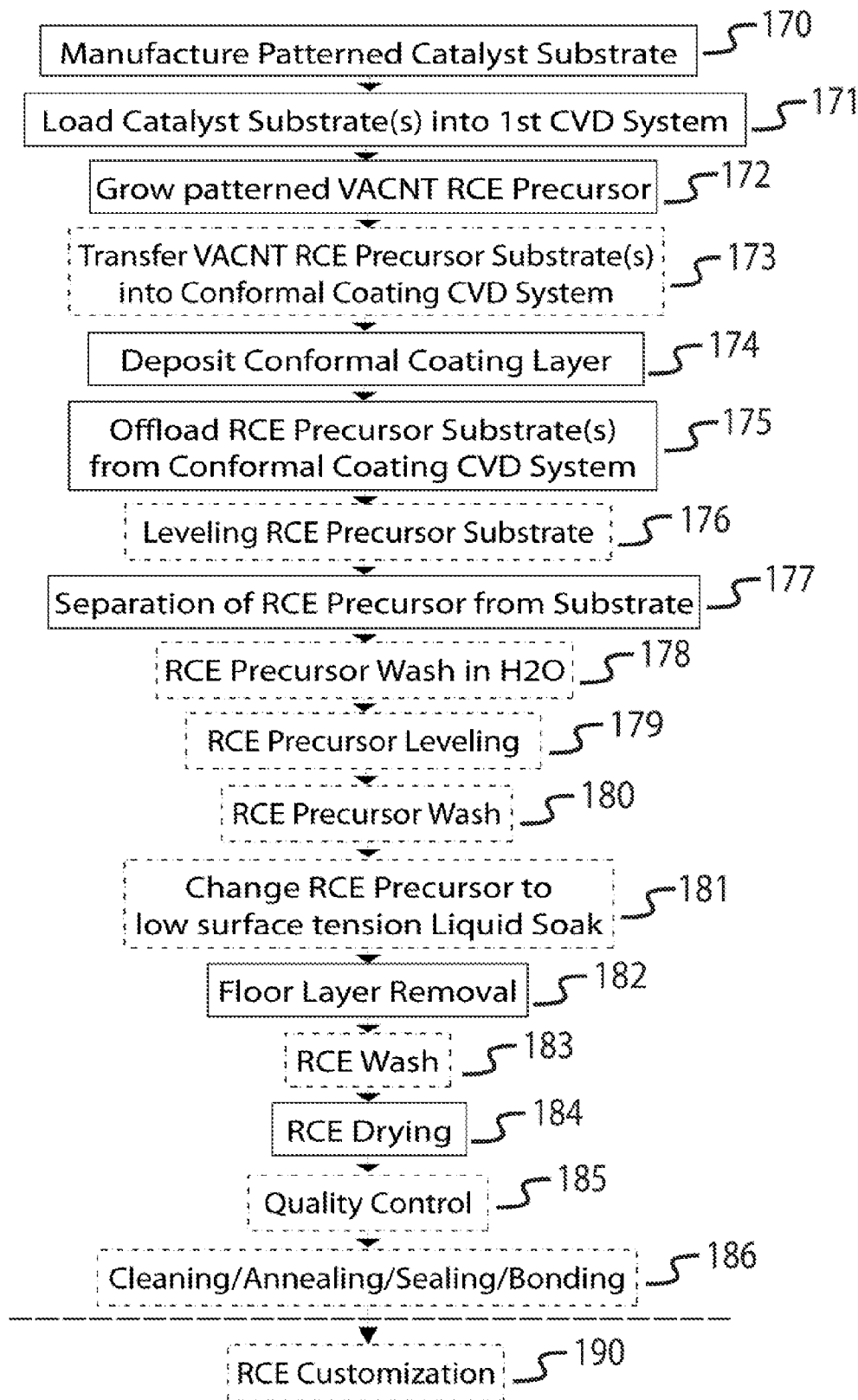
FIG. 7 is a flow chart showing the manufacturing steps used to manufacture the reactor core element samples of FIG. 5, as well as other manufacturing steps that may be used for manufacturing suitable reactor core elements.

A non-limiting, illustrative manufacturing process used to manufacture the different reactor core elements 100 sample types shown in FIG. 5 are summarized in FIG. 7 together with a few other embodiments. Several of the hereinafter discussed manufacturing process steps, i.e. step 170-184, can be replaced with other suitable process steps. The methods discussed hereinafter are various embodiments for processing c-VACANT reactor core element 100 precursor structures, defined below; however, other suitable process steps either known to those skilled in the art or discussed previously herein may be used for processing c-VACNT precursor structures as well. Additionally, the process steps discussed hereinafter, as well as other process steps either known to those skilled in the art or discussed previously herein, may be suitable to form structures made from a material other than c-VACNT, such as carbon infiltrated agglomerations of first grown vertical aligned carbon nanotubes and then liquid dispersed carbon nanotubes (carbon nanotube paper-like structures), graphene platelets, nanopillars, nanowires, and/or nanofibers. Such materials can be used to form the reactor core elements 100 of the present disclosure together with either a conformal layer 156 deposition process or a sintering process.

Multiple reactor core element manufacturing embodiments are discussed below in relation to FIG. 7, with dashed outlines indicating optional process steps. While in general the reactor core element manufacturing process outlined in FIG. 7 follows a linear order, in embodiments, at least some of the steps after process step 175 are done at least one time outside the order listed. In other embodiments, at least one of the steps is repeated multiple times, sometimes with different process parameters, e.g. processing time, etc.

After a patterned catalyst substrate (also called "growth substrate" herein) is made in step 170, at least one patterned catalyst substrate is loaded into a first CVD system in process step 171.

To make the samples shown in FIGS. 5 and 6A-6D, a bare Si wafer was used as a starting substrate that was photolithographically processed with a patterned 1.7 μm thick negative photoresist (nLOF 2020 as sold by Integrated Micro Materials with all accessory chemicals needed to process it).

In embodiments, the catalytic vertical aligned carbon nanotube growth thin film coating stack includes a 20 nm $SiO_2$ film, a 10 nm $Al_2O_3$ film, and a 0.8 nm Fe film, all deposited in series with an e-beam deposition system. The 0.8 nm Fe film gave the fastest vertical aligned carbon nanotube growth rate (from a Fe film thickness range of 0.5-2.0 nm) and the addition of the 20 nm $SiO_2$ diffusion barrier/isolation layer allowed to increase the growth height of vertical aligned carbon nanotube and c-VACNT precursor structures to h>2 mm in 70 min and to h>5 mm in 180 min in vertical aligned carbon nanotube growth time with the vertical aligned carbon nanotube process conditions discussed below. Other methods known to those skilled in the art and as discussed throughout this disclosure may be used to make such patterned catalyst substrates for process step 170.

CVD systems suitable for step 171 include, for example, a commercially available CVD horizontal tube furnaces configured for vertical aligned carbon nanotube growth (EasyTube® ET2000 or ET3000 manufactured and sold by CVD Equipment Corporation under the FirstNano® brand). Such a commercially available system can grow at least one patterned vertical aligned carbon nanotube reactor core element precursor structure (also called vertical aligned carbon nanotube forest or VACNT herein) on the at least one loaded catalyst substrate, thus creating a VACNT reactor core element precursor substrate (also called VACNT precursor substrate) that holds at least one VACNT reactor core element precursor.

In embodiments, at least one growth substrate is loaded in process step 171 having a single sided, suitably patterned catalytic film stack, with the catalytic side positioned on the top of the substrate, while the back side of the substrate is supported by a tray made from quartz or some other process compatible material. In other embodiments, double sided catalyst substrates are made in process step 170 with a double-sided photolithographic process so that both sides have a suitable patterned catalytic film stack deposited onto them. In embodiments, at least one pair of substantially identically sized, single-sided catalytic active substrates are loaded with their backs against each other so that the catalytic film is on the outside of each such pair. Each such back-to-back growth substrate pair is supported in embodiments by at least three, and in another by four, quartz posts that are sufficiently tall and free of gas flow limiting obstructions to allow sufficient gas exposure on the top and bottom of such pairs, so that the vertical aligned carbon nanotube height h is substantially similar on the top and bottom side of each of such pairs. In other embodiments, at least one double-sided catalytic active growth substrate is loaded. In further embodiments, at least one pair of single or double sided catalytic growth substrates is loaded with two catalytic active sides in contact with each other, so that both substrate wafers get the same gas exposure on their inner and outer surface sides; however the inner sides may optionally get a different gas exposure rate that the outer sides, thus resulting in a different height h for the inner vertical aligned carbon nanotube structures as compared to the height h for the outer vertical aligned carbon nanotube structures that are grown during step 172. In other embodiments, single- or double-sided catalytic active substrates or substrate pairs, are spaced in at least one horizontal or vertical loading plane along the hot zone of a first CVD system with a sufficient gap between the top and bottom of a vertically or horizontally oriented process tube and/or between each available horizontal or vertical substrate loading plane to allow substantially uniform process gas access to each substrate loading plane. In alternative embodiments, a group of vertically or horizontally arranged single-, back-to-back single-, or double-sided catalytic active substrates, with a sufficient gap (e.g., a gap at least three times the height of the vertically aligned carbon nanotubes) between each vertical or horizontal loading slot, are loaded with an appropriately designed holding means (for example a wafer boot or a rack with an optional slight incline plan) inside a horizontal or vertical process tube. The holding means can be made from quartz or any other process compatible material as known to those skilled in the art.

The samples shown in FIG. 5 were made with 3 back-to-back mounted pairs of single-sided catalytic active patterned 4" catalyst Si wafers supported by four vertical quartz posts arranged horizontally on a single plane with minimal spacing between them inside a 5" horizontal process tube (EasyTube® 3000), thus providing an ≈12" long usable c-VACNT processing zone capable of processing six 4" sized substrates in one batch with each holding 12, ≈15 mm×30 mm big, reactor core element 100 precursor samples. Similarly, up to 1447 mm×30 mm precursor samples can be made in one batch, for example, for side or corner sealed incorporation into a reactor core subcomponent 250.

In embodiments, at least one part of a VACNT precursor substrate containing at least one VACNT reactor core element precursor is then transferred to a second CVD system that is configured for a suitable conformal coating process. The conformal carbon coating 156 transforms the VACNT reactor core element precursors into c-VACNT reactor core element precursors, where the "c" stands for "carbon coated". Hereinafter, the c-VACNT reactor core element precursors may also be referred to as a reactor core element precursor or c-VACNT precursor.

As with step 171, step 174 can be accomplished with a commercially available CVD horizontal tube furnace (such as EasyTube® ET2000 or ET3000) configured for a suitable conformal infiltrating CVD film deposition (sometimes also called "growth"). Process step 174 can be used to deposit/grow the conformal coating layer 156 over the loaded VACNT precursor substrate, thus creating at least one c-VACNT reactor core element precursor substrate, also referred to herein a c-VACNT precursor substrate.

In embodiments, process steps 173 and/or 174 are repeated multiple times until the desired conformal coating layer 156 is obtained. More than one suitable second CVD system may be used. In other embodiments, both the process steps 172 and 174, hereinafter collectively called c-VACNT process, are done sequentially in the same first CVD system, as was done to make the various reactor core element 100 samples shown in FIG. 5.

In embodiments of process steps 172 and 174, the flow rates of the process gases are approximately scaled by the area ratio of the process tube's inner diameter. The use of oxygen-free gaseous precursors typically works for making patterned reactor core element precursors with a height h<0.5 mm, with appropriate height tuning through the growth time selection for process step 172 and thickness selection of the Fe catalytic film layer in process step 174. To grow taller VACNT forests and thus ultimately make taller c-VACNT precursors, a small amount of $H_2O$ vapor may be added during the process step 172. While $H_2O$ vapor addition during process step 172 extends the lifetime of the Fe catalyst layer and therefore allows the growth of vertical aligned carbon nanotube precursors with h>4 mm, the edge 109a of these patterned reactor core element precursors may curl up and the sidewall 129 bow outwards. Process steps 176 and 179 may be used to flatten the top surface of the c-VACNT precursor.

In other embodiments, a small amount of $O_2$ or air (instead of water vapor) is introduced as a precursor gas during the process step 172 to (i) accelerate the growth rate of vertical aligned carbon nanotubes structures, (ii) achieve an extended length zone of growth height uniformity, and (iii) create squarer-shaped parts with vertical sidewalls and a flatter top surface, i.e. to prevent the creation of muffin-top shaped parts. Using an appropriate amount of air or O2, superior squarer-shaped vertical aligned carbon nanotube precursor samples can be obtained over an extended distance along the heated furnace zone, and faster growth rates can be obtained and thus the yield and production capacity of c-VACNT precursors per batch can be significantly increased. Fine tuning the H2/C2H4 ratio also aids in achieving a balance between growth rate, catalyst lifetime, and height uniformity along the process tube length for a horizontal CVD process tube or height for a vertical CVD process tube. In other embodiments, a precursor gas may be selected from oxygen, water, carbon dioxide, carbon monoxide, ethanol, isopropyl alcohol or other oxygen containing gases.

For example, to make the reactor core element 100 samples of type ST1-ST6 and ST10-ST12 as shown in FIG. 5, three back-to-back pairs of suitably patterned single-sided catalyst substrates made in process step 170 (as detailed above) were loaded into a 5" process tube of an EasyTube® 3000 system in process step 171. During the 70 minute vertical aligned carbon nanotube growth process step 172, done at 750° C., these catalyst wafers were exposed to a mixture of process gas precursors having the flow rates of $N2/H_2/O_2/C_2H_4$=2769/3194/2/2396 sccm or $Ar/H_2/Air/C_2H_4$=2769/3194/10/2396 sccm. For these samples, the conformal coating 156 deposition process step 174 was accomplished at a process temperature of 900° C. and $H_2/C_2H_4$ 12,000/4,000 sccm. Reactor core elements 100 have also been manufactured by using the above process recipes for the c-VACNT process in an EasyTube® 3000 system with fluid channels 104 that have a fluid channel diameter $\phi_{FC} \geq 4$ μm and a channel to channel gap $g_{FC} \geq 5$ μm, even with h≈2 mm, thus demonstrating that reactor core element 100 samples of type ST 20 and ST21 listed in TABLE 1 are also manufacturable with the presently disclosed methods, although not shown in FIG. 5.

The first vertical aligned carbon nanotube growth step 172 allows the creation of the extruded shape of the desired reactor core element 100 cross sectional shape (especially when the $O_2$ or air assisted process step 172, as outlined above, is used) in the form of a very loose agglomerated patterned vertical aligned carbon nanotube structure (forest). As discussed above, this preliminary vertical aligned carbon nanotube structure has practically no usable stiffness, is too fragile to survive separation from its growth substrate, and typically locally deforms (collapses) after drying. The second carbon interlinking and densification manufacturing process step 174 transforms the fragile and otherwise unusable patterned vertical aligned carbon nanotube structure into an open-pore cellular network material 150 having a solid phase 152 with a bi-continuous tortuous phase, by effectively locally carbon-welding individual carbon nanotubes together wherever ligament preforms 155 come locally sufficiently close to each other, e.g. within D<2*T, and/or actually contact each other. These welds 154 are typically spread 200-5,000 nm apart providing the desired stiffness and mechanical strength to the structure. In FIG. 4, the material welds 154 represent the mechanically interlinked carbon nanotube regions.

The stiffening of the carbon nanotubes (i.e., diameter increase through the conformal coating 157) and frequent random interlinking (i.e., random separated local spot welds along the lengths of the carbon nanotubes) mechanically stabilize the total structure so that it behaves as a semi-flexible sponge-like material from which no individual carbon nanotube or carbon nanotube bundle can be removed without destroying the local structure.

The stiffness and mechanical strength of such a reactor core element 100 depends on the average diameter of each densified carbon nanotube inside the c-VACNT type open-pore cellular network material 150. Those skilled in the art reading this disclosure will understand that, for each fluid reactor application, the height h and/or mechanical strength of reactor core elements 100 and, therefore, their production costs need to be balanced against their value proposition for a given application. For example, it might cost less to make one 2 mm than two 1 mm tall reactor core elements. It may also not be cost efficient, after yield considerations, to make extra tall reactor core elements since while the vertical aligned carbon nanotube growth rate slows down over time, the heat up and cool down time is approximately fixed for each separate batch. The decaying growth rate of vertical aligned carbon nanotubes is process parameter and catalyst film stack dependent. Additionally, a catalyst wafer made in process step 170 has a finite lifetime (process parameter dependent). Therefore, sometimes the vertical aligned carbon nanotube growth rate comes to a halt prematurely for some catalyst wafers and/or for some localized regions of the wafers and not for others (for example, due to substrate quality, e-beam run processes, and/or processing liquid purity dependency), which makes growing until or beyond the average catalyst lifetime of the growth substrates less cost efficient, unless the optional leveling process step 176 and/or 179 is added to the overall c-VACNT precursor manufacturing process. Pushing the VACNT forest growth too close to or beyond the lifetime limit of a catalyst substrate can sometimes also lead to undesired height variations over extended growth areas and/or when multiple substrate wafers are loaded, thereby possibly reducing the yield of usable c-VACNT precursors for a targeted narrow range for height h values without the optional leveling process step 176 and/or 179, as will be further discussed below.

In embodiments, simultaneously with the formation of the open-pore cellular network material 150 of a given reactor core element 100, its outside edge 109a and any of its internal features are extruded substantially perpendicular to its input surface 101. Therefore, the reactor core element 100 can be used without any further surface height leveling and/or height shaping process steps 176 or 179. This is how the samples shown in FIG. 5 were made.

After the CVD system off-loading process step 175, the solid phase 152 of the resulting open-pore cellular network material 150 is often somewhat hydrophobic. This is the reason it can take a while (several minutes) for water to fill all the void phase 151 of the open-pore cellular network material 150. In embodiments, a small amount of surfactant or liquid is added to at least one processing liquid that is water-based and is used during any of the process steps 176 to 183 to lower the surface tension of this liquid. In particular, useful surfactants are those that have an affinity for carbon at one end of their molecules. Examples of such surfactants include those that are commercially available for creating dispersions of carbon nanotubes or graphene nanoplatelets, such as Triton™ X-100, sodium dodecyl sulfate, Tween® 20, Tween® 80, or sodium cholate, as well as other surfactants known to those skilled in the art. If some amount of these surfactants remains attached to the solid phase 152, after a prior washing step, they can be removed from its surface with a heat assisted cleaning/annealing treatment step 186, as will be further discussed below. Adding alcohol to a water-based liquid, for example ethanol at a 50/50 volume ratio, also lowers its surface tension significantly.

In embodiments, after the 2-step c-VACNT process, the top surface of a c-VACNT precursor substrate gets leveled in the optional process step 176 close to a controlled predetermined height h and/or flatness across the substrate. In other embodiments, height trimming is done either perpendicular to or at a slight tilt angle to the catalyst growth substrate in order to obtain reactor core elements 100 with either a parallel or angled input surface 101 and output surface 102. In embodiments, the leveling step 176 is done dry. In other embodiments, the leveling step is done wet with a suitable polishing liquid, liquid mixture, or emulsion (hereinafter "polishing liquid") selected from the not intended to be limiting group including water, ethanol, methanol, mineral oil, oil, grease, lubricant, acetone, surfactant solution, suspended nano-sized powders, and a colloidal, $SiO_2$ or $Al_2O_3$ based suspension (e.g. as sold by Buehler or Lesco). In embodiments, such a polishing liquid is constantly filtered, frequently filtered, renewed, refreshed, and/or topped off.

In embodiments, the leveling process step 176 is accomplished with a surface grinder, a milling tool, or other height trimming methods suitable for the patterned open-pore cellular network material 150 structure. The height trimming method selected for step 176 should minimize chipping at the multiple inside and outside edges of the reactor core element. In alternative embodiments, a reactor core element precursor wafer is placed upside down on a vibratory polisher (for example, VibroMet™ 2 sold by Buehler) that uses a standard vibratory polishing felt inside a polishing pan which is filled a suitable polishing liquid. To prevent the top surface of a reactor core element from being over-polished, a suitable tool should be used to hold the upside-down oriented c-VACNT precursor substrate at the correct distance from the vibrating pan polishing pad, i.e. to prevent polishing beyond a target height h set by suitable standoff feet of the respective c-VACNT precursor substrate holder.

In other embodiments, the process step 176 includes first a leveling process step followed by a 1-15 minute ultrasonication cleaning bath step to remove at least some of the accumulated polishing debris and/or polishing liquid components from the clogged portions of the fluid channels 104. A suitable sonication liquid is a polishing liquid. Another suitable sonication liquid is a liquid or liquid mixture, or emulsion from the not intended to be limiting group including water, ethanol, methanol, oil, acetone, surfactant solution, also called a cleaning liquid herein. After this polishing step is completed, the top surface leveled reactor core element precursor substrate needs to be moved to process step 177 without getting dry, otherwise some of the reactor core element precursors patterns might get damaged due to uneven capillary drying forces, for example, from uneven loading of the top parts of the fluid channels 104 with debris.

The process step 176 or 179 can be used to remove the typically <2 μm and often <1 μm long "nose hairs" 158 (conformal layer 156 overgrowth arising from the process step 174) along the edges of the top side of the fluid channels 104 (see FIG. 6B). These nose hairs 158 may (i) partially stick out into the flow path of a fluid channel 104 (depending on how aggressive/fast and/or uniform throughout the open-pore cellular network material 150 conformal layer 156 thickness T is), (ii) act as ultra-thin (<100 nm, typically <20 nm) flow restrictors for fluid channels 104 with fluid channel diameter $\phi_{FC}$<20 μm, and (iii) break off initially and/or over time during the startup/utilization of the reactor core elements. Therefore, process steps 176 or 179 provides the means to cost effectively remove these "nose hairs" 158, thus cleaning and/or rounding the entrance/exit edges of the fluid channels 104 and preventing the nose hairs 158 from restricting the flow through any ultra-narrow fluid channels 104. This is particularly useful for a reactor core element 100 with fluid channel diameter $\phi_{FC}$<20 μm, or more specifically, with a very small fluid channel diameter $\phi_{FC}$≈3-5 μm.

After the c-VACNT precursor substrates have been created via the two-step c-VACNT process, the c-VACNT precursors located on the growth substrates need to be separated from them in process step 177.

In embodiments, the manufacturing process step 177 separates the reactor core element precursors from their growth substrate, without any prior floor layer 157 removal process step 182, by using a low tech, vibratory shaker table that holds in a sealed container, partially filled with a separation liquid, at least one piece of a reactor core element precursor substrate containing at least one reactor core element precursor sample. This allows hands free separation of the reactor core element precursors from their growth substrate, typically in 15-120 minutes time, depending on the thickness T and defect quality (pinhole rate) of the conformal coating layer 156 and the design of the catalyst thin film stack on the support substrate previously applied during process step 170. In other embodiments, a separation of the reactor core element precursors from their growth substrate is achieved by just letting the reactor core element precursor substrate soak from 0.5-72 hours in a separation liquid filled bath. The c-VACNT precursor separation time from the substrate is typically not consistent from one c-VACNT precursor substrate to the next and depends on how dense and defect free a particular conformal coating layer 156 is for a given batch run.

With either of these two embodiments, multiple c-VACNT precursor substrates can be processed in parallel. An advantage from utilizing a vibratory table includes the ability to significantly (>10×) speed up, on average, the production rate of the process step 177, thereby resulting in a faster separation of all c-VACNT precursors from a given c-VACNT precursor substrate, even if there is a narrow gap between two neighboring c-VACNT precursors on a c-VACNT precursor substrate, e.g. 10-500 μm, or more typical 50-150 μm. In general, the bigger this gap, the faster all the individual c-VACNT precursors separate from the growth substrate.

A suitable separation liquid is any acid or base based etching solution that etches at least one of the intermediary thin film layers located between the growth substrate and the open-pore cellular network material 150 and conformal layer 156. Additionally, the separation liquid should be essentially inert to the solid phase 152 of the open-pore cellular network material 150 and should only minimally attack the growth substrate so that the substrate can optionally be recycled. In embodiments, for Si wafer-based growth substrate, the separation solution can be 2-10% HF by weight or volume in water.

The samples shown in FIG. 5 were separated in a 10% HF separation solution bath inside a sealed polypropylene box that was agitated for 15-60 minutes on a vibratory low-tech shaker table to separate all nine ST1-ST6, ST10-ST12 type c-VACNT reactor core element precursors having initially a 100 μm gap between them, from their common 4" Si wafer growth substrate. All ST type reactor core element 100 samples shown in FIG. 5 are mechanically strong enough to survive such a process for many hours without showing significant signs of wear and tear that would no longer make them suitable for their intended purpose. Thus, over-processing such c-VACNT precursor substrates during step 177 is typically not a point of concern.

After step 177, a separated substrate may be recycled by conducting either a single side re-polishing or a single side over-coating with a leveling film that is process compatible with process steps 170, 172, and 174.

In embodiments, each precursor substrate is placed inside a single sealable polypropylene separation box partially filled with separation liquid to more than cover the c-VACNT precursor substrate and many boxes are simultaneously stacked on top of each other and/or next to each other on the same vibratory shaker table. In other embodiments, multiple c-VACNT precursor substrates are stacked on top of each other, separated by a small gap that is >1.2 times the maximum height $h_{max}$ of the c-VACNT precursor substrates between them, for example, inside a tight plastic cylinder with optional suitable fluid channel communication means between each substrate level. This allows all c-VACNT precursors to eventually separate from their growth substrates while still staying localized near their original location, thus minimizing the interaction (bumping) between separated c-VACNT precursor samples from different growth substrates. In still further embodiments, the gap between the c-VACNT precursors on the growth substrate is >3*$h_{max}$. In further embodiments, the housing in which the separation occurs has a fluid exit port, thereby allowing fully separated c-VACNT precursors to float away into a collection area as the separation liquid moves with a suitable flow rate over each c-VACNT precursor substrate, thus minimizing any bumping, which further minimizes the degradation of the outer edges 109a of the reactor core elements 100 and any scratching of reactor core element top or bottom surfaces 101 and 102. In still other embodiments, one or more c-VACNT precursor substrates are stacked with a substrate>3*$h_{max}$ with a mostly open side (e.g. minimal sidewall obstructions) between them into a rack that is then placed in any manner into a suitable bath with a recirculation flow system that very gently pushes or sucks any separated c-VACNT precursors off the growth substrate into a collection area or "net."

In other embodiments, instead of a vibratory table, a vibratory conveyor belt or other similar functioning equipment moves containers filled with a separation liquid and at least one c-VACNT precursor substrate for a preset time from a loading to an off-loading location while agitating the liquid in these boxes during this time. In other embodiments of process step 177, at least one separation box or c-VACNT precursor substrate is placed in an ultrasonic bath to accelerate the separation rate. Optional multiple separation boxes, c-VACNT precursor substrates, or at least one mostly open rack holding a group of spatially separated c-VACNT precursor substrates are processed in parallel. In further embodiments, a combination of vibratory shaking, ultrasonic agitations, and/or other means of generating a pulsed or continuous gentle fluid motion is used to speed up separation process step 177.

In still further embodiments, a 10-100 nm $SiO_2$ underlayer is deposited between a bare Si wafer and the $Al_2O_3$ layer that may be applied during step 170. In other embodiments, a $SiO_2$ underlayer is deposited on a thermal oxide treated Si wafer having a film thickness of >10-100 nm. Deposition of such an SiO$_2$ underlayer may be done, for example, via e-beam, thermal evaporation, or sputtering in the same catalyst film stack deposition run or in a separated coating batch run or via a continuous conveyor belt driven SiO$_2$ flame spray deposition run. Adding such an easily HF etchable SiO$_2$ underlayer extends the lifetime of a Fe catalyst wafer and allows the use of a thinner Fe layer. This results in thinner and faster growing VACNT ligament preforms 155 and, thus, enables the use of more cost-effective bare Si wafers and aids in reducing the recycling cost of separated substrates recovered in process step 177. In embodiments, a thicker auxiliary SiO$_2$ underlayer is used to speed up the separation process 177 since it is easier for the separation fluid to penetrate a bigger gap between the bottom of the c-VACNT precursor structure and the growth substrate. Alternatively, SiO$_2$ wafers may be used as the starting substrates which can then be subsequently flame polished to recreate a suitable starting surface finish or they can be polished as needed to make them recyclable.

In other embodiments, a gas phase etching process (for example, HF gas with heat) etches one of the underlayers, thus allowing release of the c-VACNT precursors from the growth substrate with little mechanical bump-force and/or a slight bending and/or twisting of the substrate.

After the etch separation process 177, some of the fluid channels 104 of the thus detached c-VACNT precursors may have a thin floor layer 157 partially or fully blocking the bottom fluid channel 104 access, as can be observed in FIG. 6C. After the process step 177, the c-VACNT precursors typically become slightly more hydrophilic due to, for example, being soaked in diluted HF which reacts with defect sites of the open-pore cellular network material 150.

In the optional process step 178, the separated c-VACNT precursors get soaked and washed in a water-based cleaning bath until its pH value is close to neutral, e.g. pH=7±1. A suitable water-based washing liquid can include at least one of tap water, deionized water, activated carbon or hollow fiber membrane filtered water, purified water, sterile water, water coming from a reverse osmosis system, high purity deionized water with a conductivity of >14 MΩ or >18 MΩ, aqueous diluted HF, and/or other acid or base solution. To speed up the neutralization process of the solid phase 152 of the open-pore cellular network material 150, the water-based bath liquid can optionally be refreshed or replaced at least one time during process step 178. The bath may be continuously refreshed and/or recycled through a filtration and/or purification system to remove suspended particles, emulsions, oils, biological material, salts, surfactants, dissolved inorganic and organic chemicals, moieties, and/or ionic species. Such a filtration/purification system can include a pump, a UV light source, and/or at least one filter or purification element selected from the group including general-purpose filters, micro filters, ultrafiltration filters, reverse osmosis filters, activated carbon filters, string filters, hollow fiber membrane filters, sterilization filters, anionic resin tanks, and cationic resin tanks. In embodiments, to shorten the process time of the step 178, the washing tank may be agitated with air, at least one moving paddle, moving propeller, liquid pumps, ultrasound activator, and/or vibrational shaking method.

In other embodiments, at least one separated substrate gets washed until its surface pH or the pH of the washing liquid becomes close to neutral. Then it can be dried, for example via spin drying, and put aside for recycling at a later point in time.

In embodiments, the separated c-VACNT precursors are moved to the washing bath prior to partially or fully drying them. Alternatively, in other embodiments, the separation liquid gets replaced with at least one type of water-based washing liquid and the c-VACNT precursors get agitated and/or ultrasonicated while still in the separation container used for process step 177. In other embodiments, a suitable quantity of the c-VACNT precursors are soaked in a sealable box filled with a sufficient quantity of a water-based washing liquid and put into an ultrasonic bath for 5-30 min, typically for 10-15 min for reactor core elements 100 with a fluid channel diameter $\phi_{FC} \approx 50$ μm.

In embodiments, in the optional c-VACNT precursor leveling step 179, each separated c-VACNT precursor, after the process step 177, 178, 184, or 185 (as discussed below), gets leveled on its top side, so that its reactor core element input surface 101 and reactor core element output surface 102 are substantially parallel to each other and are separated by a targeted height h. Alternatively, a wedge angle or other targeted surface curvature is created between them by applying a suitable leveling method, such as an appropriately programmable CNC and/or a surface grinding system processing, to either flat or pre-bent mounted c-VACNT precursors. In embodiments, if leveling step 179 occurs after the reactor core element drying step 184, then the surface leveling process can be done with a wet or dry leveling process. Alternatively, if level step 179 occurs after steps 177 or 178 (i.e. prior to the drying step 184), then it is most efficient to apply a wet leveling step.

In embodiments, a suitable c-VACNT precursor holder offsets at least one of c-VACNT precursor in such a way that a vibratory polishing step (using similar equipment as in process step 176) yields the targeted surface relationship between its input surface 101 and output surface 102. In embodiments, this relationship is a parallel input surface 101 and output surface 102 that are offset from each other by a targeted height h. Alternatively, if the c-VACNT precursor holder has a small curvature to it, then the negative of this curvature can be transferred to the front part of the held c-VACNT precursor through a flat grinding leveling step since the c-VACNT precursor is flexible enough to follow a small curvature imparted by its holder.

A more aggressive VACNT growth process step 172 with a wider process window and/or a higher loading capacity for a given first CVD system in process step 171 can be used if at least one of the leveling steps 176 and 179 is included in the reactor core element manufacturing process. By incorporating height leveling process step 176, a water vapor based VACNT grow process step 172 or more aggressive carbon infiltration process step 174 can now be used, since the process step 176 can remove (when desired) many of the above discussed process artifacts. In addition, the more catalyst substrates are loaded in process step 171, the less the height uniformity of the resulting c-VACNT precursor samples will be. Therefore, leveling either all c-VACNT precursor substrates during a process step 176 or all separated c-VACNT precursors during a process step 179 to a desired height provides significantly increased production throughput capacity of the c-VACNT process. Additionally, for example, if height leveling is done during step 179, the height for each reactor core element precursor can be individually customized, thus providing the option of maximizing the usable height of each c-VACNT precursor.

In embodiments, reactor core elements 100 are made without a 176 or 179 top surface leveling step. In such embodiments, the reactor core elements 100 already have a top surface flatness and roughness that is good enough to make a top sealing zone 105-*t* or they are edge or corner sealed with 105-*s* or 105-*c* sealing zones. For example, the samples shown in FIG. 5 were made without employing steps 176 or 179. In other embodiments, reactor core element 100 are height sorted in the quality control step 185. For example, such height sorting may include sorting reactor core elements 100 into 100 µm separated height bins with a ±50 µm height tolerance range. The utilization of such height sorted reactor core elements 100 is discussed below in relation to reactor core 200 manufacturing and FIG. 8.

In other embodiments, the top surface of a c-VACNT precursor is finely polished in a vibratory polishing cup or equivalent system, as discussed above in relation to step 179, without any tooling and without a specific height adjustment goal, but instead with the goal to clear and slightly round off the edges of the top section of fluid channels 104, e.g., to remove any possible "nose hairs". For example, a briefly applied process step 179 makes the performance of reactor core elements 100 more consistent, when desired, even if they have very small fluid channel diameter, i.e. $\phi_{FC}$=3-20 m.

In the optional process step 180, top surface leveled and/or shaped c-VACNT precursors are washed with a washing liquid to allow the removal of at least some of (i) the polishing debris that accumulated in the top portions of the fluid channels 104 of the surface leveled c-VACNT precursors, (ii) the remaining solid particles and/or oils from a polishing liquid used during a prior leveling step 179, and/or (iii) the remnants from step 176. In further embodiments, during the c-VACNT precursor washing step 180, an ultrasonic bath and/or other mechanical, agitation, or fluid flow promoters are used to help at least partially unclog the top portions of the still bottom sealed fluid channels 104 from debris and/or polishing particles. In embodiments, if the solution used during a wet c-VACNT precursor leveling process step 179 has a non-neutral pH value, this washing step 180 also aids in bringing the solid phase 152 surface of a c-VACNT precursor closer to a neutral pH value. In embodiments, the polishing liquid from step 180 is exchanged with a washing liquid having a lower surface tension to enhance the removal rate of debris. In embodiments, the washing liquid is exchanged at least once during the process step 180.

In embodiments, the washing liquid for step 180 is either a water-based washing liquid, as described in relation to step 178, or a liquid or liquid mixture selected from water, ethanol, methanol, acetone, oil, and mineral oil and may contain one or more surfactants and other compatible additives that help with the removal of debris and/or foreign particles and their extraction ability from the washing liquid, for example, in a filtration stage. In other embodiments, the unbalanced pH of the reactor core element precursor from process step 177 or 179 is corrected in a later process step 186, as will be discussed below, and the separated c-VACNT precursors will be handled properly in the meantime (i.e., via gloves, plastic grippers, plastic bath containers, etc.).

In the optional process step 181, a c-VACNT precursor is soaked in a low surface tension liquid. In embodiments, the separated c-VACNT precursors are removed from a prior liquid and then placed directly into the low surface tension liquid before they start to partially dry out. In other embodiments, the c-VACNT precursors are not moved at all and, instead, the washing liquid is exchanged with at least one low surface tension liquid. In further embodiments, the c-VACNT precursors are removed from a prior liquid and placed on an absorbent material, e.g. at least one sheet of absorbent paper, to soak out quickly at least the liquid contained inside all through channels (any fluid channels 104, SFC 132, or channel extrusions 119). Then, this partially dried c-VACNT precursor is optionally moved to another dry absorbent material and then sprayed down with a low surface tension liquid. These last two steps can be repeated as needed. Then, the wet c-VACNT precursor is moved to the bath containing a low surface tension liquid and soaked therein, optionally with the aid of ultrasonication and/or other fluid motion inducing means (e.g. vibration, moving propellers, flow pump, air agitation, etc.). The optional intermediary partial drying/rewetting steps outlined above can help to extend the lifetime of the low surface tension bath solution.

Suitable examples of such a low surface extension liquid, without intending to be limited, are liquid or liquid mixtures selected from the group of methanol, ethanol, water, and liquid surfactant.

At this point in the reactor core element manufacturing process, as observable in FIG. 6C, the floor layer 157 at the bottom of the fluid channels 104 of the separated reactor core element precursors is still mostly (or at least partially) present. As stated above, and as can be seen in FIG. 6C, at the substrate side of the fluid channels 104, a floor layer 157 is also grown during the process step 174. The floor layer 157 needs to be removed to enable normal flow rates through fluid channels 104 so that such fluid channels 104 can contribute fully (not only partially) to the fluid reactor processing rate of the reactor core element 100 and thereby become fully active.

In embodiments, at least one c-VACNT precursor is soaked in a polishing fluid and sonicated until most of the fluid channels are without these floor layers 157. For example, to make the reactor core element 100 sample type ST1 having fluid channels 104 with a fluid channel diameter $\phi_{FC}$=46.5 µm, as shown in FIG. 5, on average a 5 hour ultrasonication process (60 minutes on and 30 minutes off, repeated 5 times) produced reactor core elements 100 that have between 80% to 95% of these floor layers 157 removed, or at least removed to the level of a partial floor layer 157*a*, as shown in FIG. 6C, thereby making it active. If during an optical quality control step 184 (as will be discussed below), a reactor core element sample was found that had a lower than desired percentage of floor levels 157 removed, then these parts can be reworked again another time with the same floor level removal process 182, until the part clears the quality control step 185. By comparison, reactor core elements 100 having fluid channels 104 with $\phi_{FC}$=100 µm can get to the same or better floor level removal percentage level typically in ≤60 minutes. However, the smaller fluid channel diameter $\phi_{FC}$ becomes, the harder it is to remove the floor layers 157 with this method.

The floor layer removal step 182 may be improved if some of the debris from a prior leveling step 176 or 179 is still located inside the fluid channels 104. Ultrasound waves help push at least some portion of this debris towards the floor layer 157. Given their higher mass density, this debris has a higher probability of clearing the bottom entrance of the fluid channels 104 than a particle free liquid, i.e. there is a higher probability of removing even the partial layers 157*a*. Therefore, in embodiments, c-VACNT precursors that have undergone a prior leveling process step 176 or 179 are put through the floor level removal ultrasonication process without any, or at least only with a minor, prior debris removal/washing process step 178 or 180.

In embodiments, most fluid channels 104 are partially or fully filled with removable debris and/or the ultrasonic floor layer removal solution intentionally includes a suspended small hard and/or soft particle with a diameter<5× or <50× of the fluid channel diameter $\phi_{FC}$. This debris or particle load inside the ultrasonication liquid and/or fluid channel accelerates the removal of the floor layer film 157 or 157a covering at least part of the fluid channel 104 input. In embodiments, the particle material added to the sonication liquid to accelerate the floor removal process step 182 has a substantially smooth and spherical shape and is made from an easily removable and/or etchable material with a method that is basically not destructive to the solid phase 152, e.g. colloidal $SiO_2$ that can be easily removed with a diluted HF solution.

In further embodiments, such a floor layer removal process 182 exposes c-VACNT precursors to one or multiple liquids having similar or different densities or viscosities and/or to liquid mixtures or emulsions (oil and water mixtures). Such liquids or liquid mixtures may be optionally agitated by mechanical, gas flow, or ultrasonic means, thereby breaking the floor layer 157 and "washing away" the broken floor layer pieces and/or polishing material remnants. Alternatively, gas or liquid fluids may be forced through the fluid channels 104 in a continuous or pulsed mode, thereby "pressure washing" the floor layer 157 with suitable, optionally slightly abrasive or impulse transmitting fluid sprays that do not cause sealing problems in the sealing zones.

In other embodiments, at least one separated c-VACNT precursor from process step 177, 178, 180 and/or 181 undergoes an accelerated floor level removal process step 182. Such accelerated step 182 can be done by transferring c-VACNT precursors to a vibrator polishing pan with its smoother substrate contact side touching the polishing felt, i.e. without any mounting tooling, and while floating the c-VACNT precursor in a polishing liquid that reaches at least up to 15% of its height. Unlike for certain other embodiments of a floor removal process 182, the size of the fluid channel 104 does not significantly affect this vibratory felt polishing based floor removal process 182 from achieving a targeted >90% or >95% floor level removal rate. With this embodiment, a sealing zone 105-t located at the bottom side of the c-VACNT precursor remains very smooth and only shows signs of very shallow scratches; therefore, it is typically still smooth enough to be usable as a sealing zone 105-t.

For example, all samples shown in FIG. 5 have been processed in an undiluted ethanol solution for ≈5 minutes, with up to 24 c-VACNT precursors loaded at one time in a 12" vibratory pan. Depending on the size of the vibratory processing pan, many c-VACNT precursors can be processed at the same time. A 5-7 minute processing at medium to full power causes the c-VACNT precursors to dance around in a quasi-circular motion without the aid of any mounting tools; therefore, such processing can remove the floor layers 157 at a level of better than 95%, even for reactor core elements that have a fluid channel diameter of $\phi_{FC} \leq 3\text{-}20$ μm. The sample ST12 shown in FIG. 6C was prepared with an alternate embodiment and polished for 5 minutes with a colloidal $SiO_2$ based polishing solution (Buehler or Lesco) in process step 182.

After a vibratory polishing process step 182, the removed c-VACNT precursors are optionally washed in process step 183 in a washing liquid to remove debris from the fluid channels 104, input surface 101, and output surface 102. The washing solution can be refreshed and/or changed from time to time as needed until the c-VACNT precursors are sufficiently clean. In embodiments, this washing process is accelerated with some form of liquid agitation, e.g. vibration, ultrasound, fluid motion, and/or recirculated through a filtering system. For the reactor core element samples shown in FIG. 5, a 15 minute ultrasonication bath washing step 182 was done with deionized water as the washing liquid. The washing step 183 can include a diluted HF bath followed by at least one deionized water bath to neutralize the pH of the reactor core element 100 surface. Optionally, such an aqueous bath is followed by a process step 181 as discussed above to facilitate the follow-on drying process step 184.

To transform c-VACNT precursors after process step 170 through 183 into usable reactor core elements 100 (also called reactor core element parts or sample herein), the c-VACNT precursors first need to be first dried in step 184 since they have undergone at least one prior wet processing step. Given the nanosized pore structure of the solid phase 152, any liquid that temporarily fills the void phase 151 of the open-pore cellular network material 150 evaporates from it spatially unevenly. Generally, any liquid filling the void phase 151 evaporates from the outside in. During the drying process step 184 of a wetted reactor core element 100, capillary drying-induced compression forces shorten the distance between neighboring ligaments 153. In addition, the evaporation rate in the direction of the top surface is higher than in the direction of the bottom surface (substrate side) because, even after a process step 182, the bottom surface is still partially gas tight sealed with a conformal layer 157, thus slowing down the evaporation rate in the bottom direction. The different evaporation rate between the top and bottom surface of the reactor core element 100 and its center and outer regions causes the reactor core elements 100 to curl up into an eggshell-like structure with the substrate side on its inside. Drying the wet c-VACNT precursors beyond their maximum bend stage causes the part to uncurl again and to move back to a substantially flat state, i.e. conformal to the growth substrate surface shape, which typically is flat. The maximum bend stage depends on the maximum gradient of the vapor/liquid phase front and its spatial distribution throughout the part. If this gradient is too steep or the drying c-VACNT precursor is too constrained during this curling phase, these asymmetric compression forces can locally exceed the elastic threshold of its open-pore cellular network material 150 and thus cause it to break into smaller pieces, thus destroying the reactor core element 100 shape. The c-VACNT based, open-pore cellular network material 150 of this disclosure with is bi-continuous tortuous phase structure has been engineered to have a high elastic threshold and to be strong enough to survive these capillary induced drying forces encountered during a normal manufacturing process as outlined in FIG. 7.

As stated above, the mechanical strength and elasticity of the open-pore cellular network material 150 comes from the thickness of the conformal coating layer 156 and its flexibility, i.e. its composition, structure, thickness uniformity and chemical bonding strength to the precursor ligaments 155, as well as from the spatial frequency of the welds 154 and the thickness and material composition of the ligaments 153. A minimum thickness of T≥4 nm for a high quality uniformly deposited/grown conformal layer 156 is typically sufficient to give the resulting c-VACNT based reactor core elements 100 sufficient strength to survive an unconstrained drying process, especially when, at least prior to the drying step 184, most of the liquid filling the void phase 151 is replaced by a liquid having a lower surface tension than water, for example methanol or ethanol, as described above for a process step 181.

In embodiments, at least one wet reactor core element part is first partially dried in process step 184 by (i) placing it on an absorbent material for a period of time (e.g., one to two minutes), (ii) placing it between a sandwich of multiple dry fiber-based sheets (for example, clean room wipes made from plastic fibers or paper towels made from wood or cotton fibers) that are enclosed by a solid gas-tight flat surface (e.g., plastic, glass, or quartz plates, metal sheets, etc.), and then (iii) leaving it to slowly dry over a few days. By performing step 184 with this drying process, capillary forces in the wet absorbent fiber-based sheets that enclose the reactor core element 100 assure a slow and more uniform drying of its open-pore cellular network material 150 (lower gradient), thus assuring that its local elastic threshold is not exceeded and, thereby, allowing to make dry reactor core elements 100 that are intact and substantially flat after said drying process step 184.

In embodiments, at least one partially wet c-VACNT precursor is dried in process step 184 by first placing it, unconstrained, on a thin metal plate (for example, on a Teflon® coated tray with the reactor core element's 100 substrate side in contact with the metal plate) that is then put into a preheated commercial available, standard laboratory oven for a predetermined time period, after which the plate gets removed and the dried and flat reactor core elements 100 get removed. The samples shown in FIG. 5 used this fast oven drying process step with a 120° C. oven temperature and a 20 min oven drying time. Over-processing typically has no damaging consequences for such reactor core elements 100, so the timing of the heating is not critical beyond a minimum processing time, typically determined experimentally for a given tray/oven temperature combination. Multiple wet c-VACNT precursors on metal plates can get processed at one time to increase the productivity of the process step 184, limited only by the oven size, tray heights and sizes and tray stacking density.

In other embodiments, a commercial conveyor belt oven that is convection heated or infrared heated (e.g., Conceptronic® HVN series reflow oven as sold by CVD Equipment Corporation) is used to continuously move plates loaded with wet c-VACNT precursors through a heated oven zone for a controlled amount of time. The orientation of the wet c-VACNT precursors can be optimized for a heating system to minimize the processing time. In embodiments, the substrate side gets heated first, although the process can be tuned to work for either orientation type. These oven-drying embodiments take advantage of the fact that the surface tension of a liquid is lower at a higher temperature and that, in embodiments, the open-pore cellular network material 150 is heated from the substrate side first, thus lowering the compression force gradients during the drying stage.

In the optional quality control step 185, reactor core elements 100 are evaluated against at least one specification criteria and optionally thereafter either moved to inventory while being sorted by height and/or other quality criteria or moved to a suitable rework process line that may subsequently result in an improvement of at least one quality aspect of the reactor core element 100. For example, if too many fluid channels 104 are not fully open, e.g. still blocked by a full or partial floor layer 157, such a part can be re-sent to process step 182 which will improve and open up more fluid channels 104, i.e. make more channels active 104.

In embodiments, such quality control step 185 can be done fully manually and visually with a microscope and/or height measuring device. In other embodiments, at least one optical camera is used to visualize the captured images and display on a monitor. In embodiments, imaging processing hardware/software is used to judge at least one quality parameter. The quality control parameter criteria can be selected from the not intending to be limiting group of height; average diameter $\phi_{FC}$ of the fluid channels 104; average fluid channels 104 gap $g_{FC}$; fluid channel 104 layout; size and number of unintentional through holes located within an inner edge 107; top and/or bottom surface flatness and/or roughness; wedge angle between input surface 101 and output surface 102; through hole size distribution and location inside and near the edge of a sealing zone 105-$t$; sealability of a sealing zone; number of fully blocked fluid channels 104; number of partially blocked fluid channels 104; dimensions and integrity of the exclusion zone 109; presence, shape and integrity of any available notches 117, protrusions 118, channel extrusions 119, and/or secondary fluid channels 132, etc.

In embodiments, the quality control process 185 is done with at least one automatic motion step for grabbing, moving, and placing reactor core elements 100, where the automatic motion is accomplished with suitable robotic grippers/sucker or other means, along with suitable robotic hardware and software. In embodiments, the automated pick and placement operation is assisted by image processing and/or artificial intelligence. In embodiments, the quality control step is done fully automatically—from grabbing the next part from a container filled with reactor core elements 100, to performing all quality control operational steps, and to placing the part into suitable bin or cartridge for inventory or selective rework. In embodiments, the data acquired during the quality control process step 185 is analyzed and used to fine tune the reactor core element manufacturing process, for example for cost, yields, productivity, maintenance cycle determination, preventive maintenance feedback, as well as for other purposes.

In embodiments, in the optional process step 186, dry reactor core elements 100 are cleaned, annealed, bonded and/or sealed before being placed into inventory for storage. In embodiments, the step 186 can optionally be done before and/or after the QC step 185.

In embodiments, cleaning is done with a reactor core element 100 CVD cleaning system utilizing a suitable heat ramp that allows to sterilize, bake off, vaporize, decompose, chemically de-bond, gasify, react away and otherwise remove inorganic or organic, amorphous carbon and other not well bonded amorphous carbon-based particles or surface-absorbed molecules or moieties (for example, surfactants, $H_2O$, OH, ethanol, methanol, acetone, oils, HF, acid or base groups, VOCs, polymers, other remnants form polishing, separation, and/or washing liquids, etc.) from the surface of the solid phase 152 of the open-pore cellular network material 150. Adding $H_2$, $Cl_2$, or some other reactive process gas to a cleaning phase helps, in particular, with the removal of some inorganic and/or organic absorbed species and of loosely attached amorphous carbon (for example, from decomposition of absorbed organic material) and/or of any metals (when needed). Utilizing at least a partial vacuum processing step can aid in such a cleaning phase to help remove low vapor pressure molecules.

In embodiments, after the cleaning process step, the reactor core elements 100 are annealed at a high temperature for an extended time in an at least partially $H_2$ atmosphere. This can help recrystallize the solid phase 152 of the open-pore cellular network material 152, thus making such a part stronger, more defect free, more flexible, and/or more hydrophobic. The recrystallization effect occurs faster when the annealing temperature is high and close to the melting point of a solid phase 152, while still being below the melting point. For a 100% carbon-based solid phase 152, annealing can be done between 900-2700° C., with the higher temperature resulting in a faster graphitic (SP2-type) and more crystalline structural reorganization of the ligaments 153.

In embodiments, after an annealing step, the reactor core element parts are subjected to a bonding CVD coating process to bond together any possible loose parts that may have been left over from any prior process step, and particularly from a leveling step 176 and/or 179. In embodiments, this bonding step can be accomplished with another process step 174, using a suitable coating time. Since both ends of the fluid channels 104 are not in gas tight contact with any surface, no floor layer 157 will form during such an additional conformal coating layer 156 process step 174. For example, reactor core element 100 are loaded in such a way that they are positioned vertically on their narrow side edge in contact with a loading quartz plate, or a loaded horizontally on a quartz plate having a high surface roughness. In particular, this assures that any leftover conformal coating layer 156 at the bottom of the reactor core element 100 (see FIG. 6D) that has not yet been fully polished away is sealed together into a thin and continuous film. By changing the carbon infiltration process step 174 into a more aggressive deposition mode the outside surface of the reactor core element can be sealed liquid tights without closing the void space 152 of the material 150.

The cleaning, annealing, bonding and/or sealing steps can all be done in a suitable configured CVD system, for example an EasyTube® 2000 or 3000 (CVD Equipment Corporation) as long as the system is configured with a process tube system that can handle the chosen annealing temperature. In embodiments, a first CVD system configured for process step 172 and 174 is used for a cleaning and annealing or a cleaning, annealing, bonding and/or sealing process step 186, with a chosen annealing process temperature of 900° C. and a chosen 15 minute annealing time. For example, the samples in FIG. 5 were exposed to such a cleaning and annealing step, but not to a respective bonding or sealing step.

Hereinafter, reactor core elements 100 that were manufactured with process steps selected from the group of steps 170 through steps 186 may be called "N-type," with "N" standing for "native." To enhance the performance of a fluid reactor unit 300 for a fluid reactor processing application, it is often beneficial to customize reactor core elements 100 at least in part before they are incorporated into a fluid reactor unit housing 304. In embodiments, the manufacturing process step 190 is used, as will be discussed in more detail below, to modify N-type reactor core elements 100 into other types of reactor core elements 100 that can be further customized for a targeted application.

A reactor core element 100 of this disclosure has an open-pore cellular network material 150 with a tortuous bi-continuous phase structure that has a minimal average pore size $p_{min}$ which limits the size of fluid components that can physically travel through the open-pore cellular network material 150. Thus, N-type reactor core elements, at a minimum provide a spatial filtering (also called sieving) function for suspended objects inside a primary fluid. The flow resistance for different fluid components through the open-pore cellular network material 150 are additionally controlled by the width and/or length, the Vp, the tortuosity, and the surface chemistry of the solid phase 152, which in turn controls the surface energy of the solid phase 152 and which in turn influences wetting properties of the solid phase 152 for a particular liquid fluid. These wetting properties are further controlled by the micro- and nano-level surface roughness and 3D structure of the solid to liquid fluid contact surface (see, for example, the lotus leaf effect resulting in superhydrophobic behavior that is often quantified by a contact angle determination). Thus, two open-pore cellular network materials 150 with similar $V_p$ can have different phobic performance levels for a given liquid depending, in part, on the diameters and spacing distributions of its ligaments 153 and welds 154 within its primary fluid contact surface neighborhood and on its 3D structure at the primary fluid contact surface and its surface energy level. The surface energy of the external surface of the ligaments 153 and welds 154, i.e. the surface of the solid phase 152, determines whether the part displays phobic or philic behavior and combined with a nano structure determines its super-hydrophobic and/or philic level.

For the fluid reactors 300 of this disclosure, at least a key component of a primary fluid can only be transported through the fluid channels 104 of the incorporated reactor core elements 100 and secondary fluids enter or exit the reactor core element 100 through the sidewalls 125, sidewalls 129, and/or the sidewalls of the secondary fluid channels 132 and travel through the reactor core element 100 via the void space 151 of its open-pore cellular network material 150 surrounding its fluid channels 104. To keep these primary fluid and secondary fluid flow regions separate, the primary fluid contact surface (or, at a minimum, its fluid channel primary fluid contact surface) may (i) be covered by an actual membrane film or (ii) at its primary fluid contact neighborhood, up to a depth $d_{PF}$, have a membrane-like property. The purpose of such a membrane and/or membrane-like property is (i) to provide a high permeability rate for any secondary fluids and (ii) to provide a low permeability rate for at least one component of the primary fluids beyond its primary fluid contact neighborhood. A high permeability rate for any secondary fluids through such a membrane minimizes its impact on the respective primary output fluid production rate. A low permeability rate for at least one component of the primary fluid minimizes its leakage beyond the primary fluid contact neighborhood, thereby reducing the chance that over time the leaked primary fluid component occupies (fills up) a sufficiently large enough portion of the void space 151 to increase the secondary fluid flow resistance through the open-pore cellular network material 150 which could reduce the primary output fluid productivity of such an at least partially "flooded" reactor core element 100.

Therefore, for a given reactor core element 100, its primary fluid contact surface (or, at a minimum, its fluid channel primary fluid contact surface) may have (i) a lower spatially integrated permeability rate $PR_{PF}$ for at least one component of the primary fluids, (ii) a higher spatially integrated permeability $PR_{SF}$ rate for all secondary fluids; and (iii) a spatially integrated asymmetric permeability ratio $aPR_{RCE}$ of a reactor core element 100, defined as $aPR_{RCE}=PR_{SF}/PR_{PF}$, that fulfills the inequality $aPR_{RCE}>1$ when its local values are integrated over a (primary fluid depth penetration) distance $d_{PF}<g_{FC}/2$ from the fluid contact surface. A local effective primary fluid penetration depth $d_{PF}$ is defined hereinafter as the depth into the open-pore cellular network material 150 from the primary fluid contact surface where the local concentration of the at least one component of the primary fluid drops to ≤37% of its level inside a fluid channel 104.

Such primary fluid components can be selected from the non-intended to be limiting group of solid particles, fibers, nano to micron sized particles, liquid emulsions, biological material and/or objects, gases, liquids, ions, inorganic molecules, organic molecules, polymers, macro molecules, salts, flocculations, particle agglomerations, cell agglomeration, blood cells, blood plasma, blood components, proteins, urine components, proteins, DNA, viruses, and bacteria.

All reactor core elements 100 with $d_{PF} \cong 0$ for the primary input fluid contact surface and primary output fluid contact surface may hereinafter also called S-type reactor core elements, with "S" standing for "sealed input and output primary fluid contact surface." In embodiments, while making a S-type reactor core element 100, the reactor core element sidewall 129 gets also, at least substantially, sealed at the same time, while the fluid channel sidewall 125 does not. In further embodiments, process step 190 includes first substantially sealing the sidewall 129 and then unsealing at least some of the sidewall 129, thereby creating a secondary fluid external input surface and/or secondary fluid external output surface. Reactor core elements 100 with a partially sealed sidewall 129 may be called herein E-type reactor core elements 100.

If the entire surface of the solid phase 152 of the open-pore cellular network material 150 has been modified from its "native" state, such as through a process step 190 and/or a later process step, then a reactor core element 100 incorporating such modified solid phase 152 may be called hereinafter "PM-type," with "PM" standing for "phase modified".

In embodiments, the application of a membrane creation process to at least some of the primary fluid contact area of the reactor core element 100 is done in process step 190. In other embodiments, a first (precursor) process step is done in process step 190 and at least one final process step of a membrane creation process is completed after such preprocessed reactor core elements are incorporated inside a fluid reactor unit 300, as will be further discussed below. A reactor core element 100 that has been subjected to such a membrane creation process may hereinafter be called "M-type" reactor core element, with "M" standing for membrane or membrane-like film.

A membrane creation process or membrane film deposition process may be any process that (i) uses fluid channels 104 to deliver at least a partial film precursor material and (ii) enhances the asymmetric permeability ratio $aPR_{RCE}$ of a reactor core element 100 when it is applied to an open-pore cellular network material 150 of a reactor core element 100 in such a manner that it causes a material property change (from the rest of the open-pore cellular network material 15) that is primarily localized near the depth $d_{PF}$ of the primary fluid contact surface (for S-type reactor core elements 100, such localization may just occur at the fluid channel primary fluid contact surface). In embodiments, a membrane creation process includes at least one element selected from the non-intended to be limiting group of localized thin film deposition, polymer film deposition, membrane film deposition, membrane film growth, membrane film casting, solution casting, liquid-based film deposition, CVD based film deposition, and electrochemical based film deposition. Film casting, as that term is used herein, is at least one process step that results in the creation of a thin film (e.g., polymeric film) that is basically suspended and/or supported by a solid phase of porous structure and that is not penetrating deeper than a neighborhood thickness of such a support structure. If an actual thin (membrane) film is deposited onto and/or into the neighborhood of the primary fluid contact surface during such a membrane creation process step, it typically has an effective thickness of ≤1,500 nm, or ≤500 nm. Such a film itself can have nano- or angstrom-sized pores and/or at least one asymmetric fluid component permeability property, as discussed above. If instead the ligaments 153 are coated non-uniformly with a material (either the same or different than the material used in process step 174) close to the depth $d_{PF}$ of the neighborhood of the (not sealed) primary fluid contact surface, then the diameter of these ligaments 153 increases locally, with the biggest increase being located closest to the primary fluid contact surface. This leads to a shrinking of the pore dimensions near the primary fluid contact area and thus to an increase of the asymmetric permeability ratio $aPR_{RCE}$ of a reactor core element 100. A further coating thickness increase may lead to the formation of a thin film having only a few very small through-pores left, or a dense and practically through-pore free thin film that is supported by the solid phase 152 of the open-pore cellular network material 150, that then itself can still have an asymmetric permeability ratio $aPR_{RCE}$, i.e. is sufficiently permeable (for example, having nanosized or sub-nanosized tortuous pores or other suitable fluid permeability) to respective secondary fluids.

In embodiments, a reactor core element 100 can have multiple types selected from the non-intended to be limiting group of E-type, N-type, S-type, PM-type and M-type. For example, a reactor core element 100 can be both a S- and N-type or S- and M-type reactor core element.

All S-type reactor core elements have a primary input fluid contact surface and primary output fluid contact surface that is sealed against any fluid flow through it. In embodiments, such a reactor core element customization process step is done in process step 186 and/or 190. Sealing of the primary input fluid contact surface and primary output fluid contact surface can be done by any means known to those skilled in the art, as long as the resulting surface is chemically compatible (stable sufficiently long enough) with any primary fluids and secondary fluids flowing through a reactor core element 100. In embodiments, a thin layer of epoxy, silicone, rubber, solder, or plastic powder or paste is printed, at a minimum, onto at least one of the primary input fluid contact surface and primary output fluid contact surface and then such prepared parts are cured, heated, and/or exposed to UV light and/or other radiation or chemical transformation means usable to form a solid and adhering sealed layer that does not block the entrance and/or exit of any intended perforations (defined herein as the sum of all fluid channels 104 and of any available secondary fluid channels 132 and channel extrusions 119). In embodiments, both input and output surfaces 101 and 102 are sealed simultaneously or sequentially. Curing in this instance includes heat curing, polymerization initiation through interaction with air and/or humidity, bombarding with energetic particles, and/or waiting for a pre-mixed chemical to react to form the desired surface sealing film. In other embodiments, a liquid-based and/or physical vapor deposition coating process that does not significantly penetrate the intended perforations can be used, for example a glancing incident angle deposition. Alternatively, if the intended perforations are first temporarily filled (plugged) with a later removable material, these external primary input fluid contact surface and primary output fluid contact surface can be coated with any appropriate liquid and/or gas-based sealing means; afterwards, the temporary material plugs get removed to open up again the intended perforations. For example, water and/or organic solvent dissolvable polymers or solids with low melting temperature (e.g., wax, Ga, paraffin, solder, tin) or liquids with high phobicity to the solid phase 152 (mercury, water, etc.) can be used as temporary material plugs. This can be followed up by an optional cleaning step, as discussed in relationship with process step 186 or with suitable other liquid-based cleaning means, i.e. solvents, surfactants, acids and/or base liquid treatment.

In embodiments, a S-type and E-type reactor core element 100 is made in process step 186 and/or 190 by (i) substantially sealing the sidewall 129 without also fully sealing the sidewalls 125, and (ii) by removing such a seal selectively from at least some of the area of the sidewall 129 to create at least part of a secondary fluid external contact surface. Should other areas of the secondary fluid external contact surface (e.g., the sidewalls of the secondary fluid channels 132 and/or channel extrusions 119) also be coated during the sealing process step (i), such seals can also be fully or selectively removed during the removal step (ii). In embodiments, the abovementioned seal removal process step (ii) includes grinding the edge surface, for example with a wet or dry belt sander, a surface grinder, or with a vibratory polishing table with suitable polishing liquid and tooling positioning at least one reactor core element 100 so that the to-be-ground sealed surface edge area is exposed to the grinding media/surface. In embodiments, the sealing process step (i) is a tuned carbon film deposition process done at higher process temperatures and with a suitable $H_2$/hydrocarbon ratio and process pressure that results in a CVD based carbon film coating process that, in embodiments, coats the sidewall 129 so that it is sealed, and coats the neighborhood of the sidewalls 125 in a less than fully sealed manner. In embodiments, the sealing coating step (i) creates a localized thin film coating over the ligaments 153 near the sidewall 125, thereby reducing its pore size and/or concentration locally and thus effectively creating a membrane-like film near the neighborhood of the sidewalls 125 up to a depth $d_{PF}$, thus producing a reactor core element 100 that is a S-, M-, and E-type.

The long-term stability of the fluid reaction efficiency of a fluid reactor unit 300 is dependent on the long-term mechanical stability of the solid phase 152. For N- or PM-type reactor core elements 100, stability is further dependent on the chemical stability of its most exterior layer that is in direct contact with the primary fluids and secondary fluid(s). For M-type reactor core elements, stability is also dependent on the chemical and mechanical stability of the membrane film and/or membrane-like functioning neighborhood of the primary fluid, i.e. the primary fluid contact surface up to an approximately depth $d_{PF}$.

A typical fluid reactor application of this disclosure utilizing such N-type or PM-type reactor core elements 100 is a micro- or ultra- or nano-filtration process. For this application, the primary input fluid includes at least one fluid containing one or more types of suspended objects, where the suspended objects are the at least one component of the primary input fluid. At least part of the fluid containing this component needs to be purified and thus removed from primary input fluid, while this component stays behind. Thus, the purified fluid becomes the secondary output fluid. The primary input fluid, with a now increased concentration of suspended objects, becomes the primary output fluid. Therefore, the chemical composition of the primary input fluid changes, based on the increased concentration of the suspended objects, to that of the primary output fluid. The fluid reaction, in the context of this embodiment, is a concentration increase of the suspended objects. As long as the minimum dimensions $d_p$ of the suspended objects are $d_p > p_{min}$=minimum ($p_\perp$, $p_\parallel$), the entrance surface to the open-pore cellular network material 150 becomes an effective "zero-thickness" filtration membrane skin that prevents the oversized objects from penetrating the open-pore cellular network material 150. Since this size-based filtration process basically happens within a few voids layers of the void phase 151, i.e. $d_{PF} \leq 10^* p_{min} \ll g_{FC}/2$, the transmission of the secondary fluid is primarily driven by (i) the flow resistance $R_{SF}$ (as defined below) of the open-pore cellular network material 150, (ii) the width of the reactor core element 100 (iii) the pressure difference between the fluid reactor unit primary fluid input port 301 and its respective fluid reactor unit secondary fluid output port 312, and (iv) the pressure difference between input port 301 and the fluid reactor unit primary fluid output port 302. The more "philic" the properties of the solid phase 152 are in relation to its relevant secondary output fluid flow, the smaller its flow resistance is and, therefore, the less energy is needed to filter (purify) the primary input fluid, i.e. to convert a primary input fluid into a secondary output fluid while simultaneously also creating a primary output fluid, that in embodiments is a waste channel.

Another typical fluid reactor application is an artificial lung (often also called extra corporeal membrane oxygenator or ECMO) which is used to provide $O_2$ gas (secondary input fluid) to venous blood (primary input fluid), (e.g. with an $O_2$ saturation level $SO_2 \approx 70\%$) and to remove $CO_2$ gas (secondary output fluid) from the primary input fluid, thus creating an arterial blood (primary output fluid), e.g., a blood with an oxygen saturation level $SO_2 \approx 95\%$. The blood is primarily composed of blood cells and plasma (which is primarily composed of water). $O_2$ and $CO_2$ can be stored in the hemoglobin molecules inside the blood cells and, to a much lesser degree, also inside the plasma. In this fluid reactor application case, the at least one component of the primary fluid includes both the blood cells and the plasma and the fluid reaction is blood oxidation and removal of $CO_2$ from it. Since ≈95% of the oxygen is stored in the hemoglobin molecules of the red blood cells, the oxygenation of blood is essentially a saturable fluid reaction. The more hydrophobic the properties of at least the fluid channel sidewall 125 neighborhood (sidewall skin) is, the shorter the primary fluid penetration $d_{PF}$ becomes for the water portion of the blood, as will be further discussed below.

Therefore, in embodiments, the open-pore cellular network material 150 is surface treated in process step 190 (i.e., its surface chemistry gets modified) to increase the "philic" properties of the solid phase 152 with respect to a secondary output fluid and/or to increase the "phobic" properties of the solid phase 152 with respect to at least one key component of the primary fluids. Many such "philic" and "phobic" treatments are within the purview of those skilled in the art for the purpose of changing the "philic" or "phobic" level of the solid phase 152 against specific liquids and/or liquid suspended components. For example, if the solid phase 152 has an SP2-type external carbon surface layer (for example, the c-VACNT processed reactor core element 100 described in FIG. 7), its external surface is very graphene-like with near perfect hexagonal-shaped carbon atom arrangements, thus forming a substantial non-polar "skin," especially if a high temperature annealing process step 186 is applied to the reactor core element 100 part. To make such a carbon surface, more hydrophilic (polar) defects in such a "perfect" carbon structure need to be created, which allows molecules to bond (forming a skin) over such a carbon surface that have a polar end, thus creating a more and more hydrophilic surface so that more such polar molecules bond to such a more defective carbon surface. In other embodiments, the open-pore cellular network material 150 may be surface treated in process step 190 in order to give it application specific properties, such as surface treatment in order to make the primary fluid contact surface antithrombotic right at the surface and hydrophobic slightly below it in order to minimize water penetration and red blood cell damage over time.

In embodiments, in step 190, N-type reactor core elements 100 with a hydrophilic solid phase 152 are soaked in an acid or base including at least one element selected from the non-intended to be limiting group of acids (HNO$_3$, HF, H$_2$SO$_4$, HCl, chloroformic acid) or bases (NaOH, KOH), with or without the aid of ultrasound results or other agitation means, as was discussed above in relation to process step 180, thus creating PM-type reactor core elements 100. In other embodiments, to make PM-type reactor core elements 100 with a more hydrophilic solid phase 152 from a hydrophobic N-type reactor core element 100, a heat and/or plasma assisted gas phase treatment is applied during step 190, with at least one gas selected from the non-intended to be limiting group of O$_2$, H$_2$O, CO, CO$_2$, hydrocarbons, fluorocarbons, alcohols, HCl, and KOH. Such a process step can also be a precursor step that will then facilitate/enhance the chemical bonding of another material in another follow-on process step (for example the application of an antithrombotic coating). In yet other embodiments, in process step 190, the application of a uniform conformal coating of the solid phase 152 with a thin non-polar film creates a more hydrophilic open-pore cellular network material 150 and, thus, a more hydrophilic PM-type reactor core element 100. Such non-polar films can be selected from the non-intended to be limiting group of HMDS; paralene C, N, or D; polyhexafluoropropylene; polytetrafluoroethylene; perfluorodecyltrichlorosilane; organosilanes; polymethyl siloxane; diclorodimethylsilane; polypropylene; polychlorotrifluoroethylene; and polyethylene. Many of these coatings can be applied with a gas phase deposition and are typically used in MEMS production to prevent stickiness of MEMS components. HMDS and other organosilane gas phase coating systems are commercially available. A wide range of polymeric coatings, including PTFE via CVD methods, some of which are commercially available from GVD Corporation, can be applied at a sufficiently low pressure to get sufficient uniform penetration of the open-pore cellular network material 150.

In embodiments, by increasing the pressure of a gas phase process during process step 190, the deposition and/or film formation on a N-type reactor core element 100 gets more localized to the easier accessed area for precursor delivery, i.e. to the fluid channel sidewalls 125 and/or to the input surface 101 and output surface 102. Therefore, M-type reactor core elements can be made this way. For example, PTFE coating deposited onto carbon nanotubes can be used to create a superhydrophobic surface (contact angle≈160-170°). This superhydrophobicity comes, in part, from the hydrophobic properties of PTFE (commonly known as Teflon), having a contact angle of 109.2 for a flat surface, and the nano-sized roughness of the PTFE coated carbon nanotubes (also commonly known as lotus leaf effect) or, in embodiments, of the c-VACNT solid phase 152. By further increasing the coating thickness of such a PTFE film, a thin PTFE membrane-like film can be made with nanosized pores for fluid reactor applications that need it. PTFE coatings have typically good antithrombotic properties and, therefore, are typically used on medical parts that handle blood flow to reduce blood clotting incidents. To further increase the blood compatibility of PTFE coated parts, process step 190 may additionally include (i) activating the M-type reactor core element 100 before and/or after a PTFE coating is deposited over or near its primary fluid contact surface in a H$_2$ and/or carbon-fluorene gas plasma, (ii) attaching an acrylamide, and (iii) immobilizing hirudin, a potent antithrombogenicity protein from leeches, to the surface. Examples of such processes are described in Onder et al., "Alteration of PTFE Surface to Increase its Blood Compatibility," 22 Journal of Biomaterials Science 1143-1157 (2011).

In further embodiments, in process step 190 a continuous film coating and/or discontinuous nanoparticle film layer is deposited onto at least part of the primary fluid contact surface. Such nanoparticles decorating the fluid channel sidewalls 125 can, for example, serve as a catalyst particle that promote a desired fluid reaction between a primary input fluid and a secondary input fluid, thus creating at least a primary output fluid and optionally also a secondary output fluid. Such optional coatings of films or particles can further be chosen to locally change the surface energy, wettability, hydrophobicity, hydrophilicity, charge, asymmetric fluid transfer selectivity, ionic repellant ability, conductivity, biofilm fouling rate, sterilization activity, antithrombotic activity, anticoagulant activity, cell damage activity, selective chemical and/or biological material adhesion and/or deposition ability, cellular damage inducing ability, catalytic properties, and/or other desired properties for surface modifications and/or to increase the lifetime of such changes for such a primary fluid contact surface neighborhood, i.e. approximately up to a depth $d_{PF}$.

In other embodiments, in process step 190, a pyrolytic graphite coating is applied to the primary fluid contact surface of N-type reactor core elements to create M-type reactor core elements 100 that have a good antithrombotic and hydrophobic or superhydrophobic primary fluid contact surface. Such biocompatible pyrolytic graphite coatings are typically done in a fluidized CVD reactor by pyrolyzing hydrocarbons in the presence of other process gases at process temperatures of 1200-1400° C., thereby resulting in a surface concentration of about 85% carbon and 15% oxygen. These biocompatible pyrolytic graphite coatings are commercially available from CryoLife.

In other embodiments, step 190 includes (i) exposing the contact surface of the primary fluid to a polymer or colloidal polymer solution having a suitable surface tension and polymer molecule size distribution (for example, PMEA based) for a few minutes, (ii) removing the solution, and (iii) leaving the remaining surface film covering the primary fluid contact surface to dry for one or more hours. This can result in the formation of an antithrombotic membrane film usable for blood oxygenation applications, thus transforming N-type reactor core elements into M-type reactor core elements 100.

Other coatings of interest, whether they are directly attached to the N-type reactor core elements or to M-type reactor core elements with or without S-type treatment, are other commercially available antithrombotic coatings that are based on albumin or polypeptide coatings that subsequently get a covalent end point attachment of heparin (for example, low molecular weight heparin, Liquemin) or many other biocompatible coatings and coatings of interest to specific industrial, semiconductor, pharma, and/or biological applications. Trillium© Biosurface is a polymer coating with heparin applied to the blood-contacting surfaces of cardiopulmonary bypass devices, also called ECMO devices. Its structure mimics characteristics of the vascular endothelium by providing a hydrophilic, negatively charged surface that features heparin.

There are already a range of available coating technologies that make fluid reactors more productive may be beneficial to customize reactor core elements 100 of the present disclosure for specialized fluid reactor applications. Such customizations may be selected from the not intended to be limiting group of industrial processing, water processing, chemical processing, biological reactor, gas-based processing, pervaporation applications, osmosis applications, blood-based fluid processing, and/or urine-based processing.

For a given fluid reactor application having a saturable primary input fluid to primary output fluid conversion process (i.e., fluid reaction) with a substantially similar primary input fluid and primary output fluid flow rate (e.g., liquid gasification or blood oxygenation), every incorporated reactor core element 100 having a height h has a maximum primary output fluid production rate $Q_{FCZ}^{max}$ that is directly proportional to the maximum primary fluid flow rate $F_{FCZ}^{max}$ of the primary input fluid into its fluid channel zone above which a fully saturated primary output fluid flow will no longer be achieved, i.e., $Q_{FCZ}^{max} \sim F_{FCZ}^{max}$. The direct proportionality of the primary fluid pressure drop $\Delta P_{RCE}$ along the height h of the reactor core element to the primary fluid flow rate through the fluid channel zone of the reactor core element and to its height h can be derived from equations (1) and (2), i.e., $\Delta P_{FCZ} \sim h^* F_{FCZ}$. These equations show that if a maximum primary fluid flow rate $F_{FCZ}^{max}$ through a single fluid channel zone of a reactor core element corresponds to a pressure drop value $\Delta P_{FCZ}^{max}$, then a reactor core stack (RCS) representing a serial stack of n of the same reactor core elements with a total height H=n*h will require an $n^2$ times bigger total reactor cores pressure drop, i.e., $\Delta P_{RCS} = n^2 * \Delta P_{FCZ}^{max}$, to result in a n-fold increase of the primary output fluid production rate for the reactor core stack, i.e., $Q_{RCS} = n * Q_{FCZ}$. However, the primary fluid pressure drop for each individual fluid channel zone of each reactor core element 100 in the reactor cores only increases linearly, i.e., $\Delta P_{FCZ} \sim n * \Delta P_{FCZ}^{max}$.

The higher the fluid pressure is inside a fluid channel, the higher the quantity of the at least one component of the primary input fluid will leak through the membrane or membrane-like $d_{PF}$ deep neighborhood of the fluid channel sidewalls and at least partially start to flood at least some of the void space behind the fluid channel sidewall. If over time the void space starts to shrink, the secondary fluid flow resistance $R_{SF}$ will increase, and thereby cause a reduction in the primary and/or secondary output fluid production rate over time. Thus, for a given application with a targeted continuous production time $\Delta T_{POF}$ and an initial production output rate $Qi_{FCZ}$, a maximum primary fluid pressure $PFC_{max}$ can be defined for a fluid channel 104 which results in a maximum primary output fluid output productivity decay rate $(Qi_{FCZ} - Q_{FCZ})/(Q^i_{FCZ}) = 50\%$. The maximum fluid channel operation pressure $PFC_{max}$ therefore provides an upper boundary of a usable primary input fluid flow rate entering a fluid channel zone and thus of the maximum production output rate $Q_{FCZ}^{max}$ per reactor core element.

For certain conditions, the Poiseuille flow describes the velocity profile $v_{FC}(r)$ of the primary fluid flow dependent on its radius r inside a fluid channel resulting in a parabolic velocity profile having a maximum flow velocity $v_{FC}^{max} = v_{FC}(r=0)$ at its center defined by the formula $$v_{FC}^{max} = 2 * v_{FC}^{ave} = \frac{8 * F_{FC}}{\pi * \phi_{FC}^2} = \frac{8 * F_{FCZ}}{N * \pi * \phi_{FC}^2} \approx \frac{\sqrt{48} * F_{FCZ}}{\pi * CA_{FCZ}} * \frac{(\phi_{FC} + g_{FC})^2}{\phi_{FC}^2} \text{ for } N \gg 1 \quad (6)$$

which relates it to the average primary fluid flow velocity $v_{FC}^{ave}$ inside a single fluid channel, or to the total primary fluid flow $F_{FCZ}$ (defined by equation (2)) through N (defined by equation (3)) identical cylindrical fluid channels 104 inside a single fluid channel zone of a simple reactor core element having a fluid channel zone cross-sectional area $CA_{FCZ}$ enclosed by the outer edge of the sealing zone.

In embodiments, for a saturable primary fluid reaction where a sufficient secondary input fluid gets absorbed into all the available quantity of primary input fluid until approximately a maximum quantity of primary output fluid has been produced, a critical diffusion reaction time $t_c$ can be defined as the average diffusion time it takes for a secondary input fluid (or at least a component of it) to diffuse from the typically cylindrical-shaped fluid channel sidewall to its centerline. The formula $$h_c = v_{FC}^{max} * t_c \quad (7)$$

relates the diffusion reaction time $t_c$ to the height $h_c$ of a fluid channel or reactor core element above which (with sufficient available secondary input fluid quantity) even the fastest moving portion (center line of the fluid channel) of the incoming primary input fluid has already been substantially fully converted into a primary output fluid for a saturable primary output fluid, i.e., above which the primary output fluid production quantity rate saturates, i.e., $Q_{FCZ}(h \geq h_c) = Q_{FCZ}^{max}$.

The diffusion reaction time $t_c$ dependence on the fluid channel diameter $\phi_{FC}$ and diffusion constant D can be derived from a diffusion solution C(t, r) of Fick's second diffusion law for the case of an axially symmetric diffusion in an infinitely long cylinder with diameter $\phi_{FC}$ and with the following boundary conditions: (i) the primary input fluid entering a fluid channel has a uniform starting saturation concentration $C_{PIF}$, i.e. $C(0, r) = C_{PIF}$; (ii) the diffusion substance exists outside the fluid channel sidewall, penetrates the fluid channel sidewall, and diffuses towards the center of the fluid channel; (iii) when the diffusing substance contacts the primary input fluid across the fluid channel sidewall, the boundary layer is instantly fully saturated and remains so independent of the primary input fluid flow rate, i.e. $C(t, r=\phi_{FC}/2) = C_\infty$ with $C_\infty$ representing the substantially fully saturated primary input fluid concentration and therefore is also the maximum saturation concentration of the primary output fluid; and (iv) the diffusion solution $C(t, r=\phi_{FC}/2-x)$ for $x \ll \phi_{FC}/2$ is very similar to the diffusion solution for a semi-infinite domain. Solving for the time $t_c$ when the diffusion front just reaches the center line r=0 yields $$t_c \approx \frac{\phi_{FC}^2}{16 * D * v_c^2} \text{ with } v_c \approx 3.599703 \quad (7a)$$

which connects the critical reaction time $t_c$ to the fluid channel diameter $\phi_{FC}$ and diffusion constant D. $v_c$ is a constant related to the geometrical difference between a one-dimensional and a radial symmetric diffusion case.

The theoretical maximum primary fluid flow rate $F_{FCZ}^{max}$ and corresponding primary fluid pressure drop $\Delta P_{PF}^{max}$ for a given simple reactor core element with a height h for which a fully saturated primary output fluid can still be produced can be derived from the formulas $$F_{FCZ}^{max}(h=h_c) = 2*h*N*\pi*D*v_c^2 = \frac{4*h*\pi*D*v_c^2*CA_{FCZ}}{\sqrt{3}*(\phi_{FC}+g_{FC})^2} \quad (8)$$

and $$\Delta P_{PF}^{max}(h=h_c) = \frac{128*h*\eta_{PF}}{\pi*\phi_{FC}^4} * \frac{F_{FCZ}^{max}}{N} = 256*\eta_{PF}*D*v_c^2*\frac{h^2}{\phi_{FC}^4} \quad (8a)$$

which results from the constraint $h=h_c$ and the equations (7), (6), (7a), and (1) for certain embodiments of the reactor core elements. Any primary input fluid flow $F_{FCZ} > F_{FCZ}^{max}$ through a reactor core element 100 will exit the reactor core element as a less than fully saturated primary output fluid flow and have a primary fluid pressure drop $\Delta P_{PF} > \Delta P_{PF}^{max}$. Any primary input fluid flow $F_{FCZ} \leq F_{FCZ}^{max}$ will exit the reactor core element as a fully saturated primary output fluid (if sufficient secondary fluid is available) and have a pressure drop $\Delta P_{PF} \leq \Delta P_{PF}^{max}$. Equation (8) shows that the maximum productivity rate $Q_{FCZ}^{max} \sim F_{FCZ}^{max}$ of a given reactor core element for a saturable flow reaction as described above is $\sim h^2/\phi_{FC}^4$ or $\sim h*N$. As discussed above, TABLES 1 and 2 show the normalized ratio $N/N_{ST1}$ thus allowing a relative comparison of the theoretical maximum fluid reaction performance potential between the different samples ST1-ST71 (for the case where there are no other performance limits for a given fluid reactor application of a reactor core element).

Reactor Cores

Figure 8:
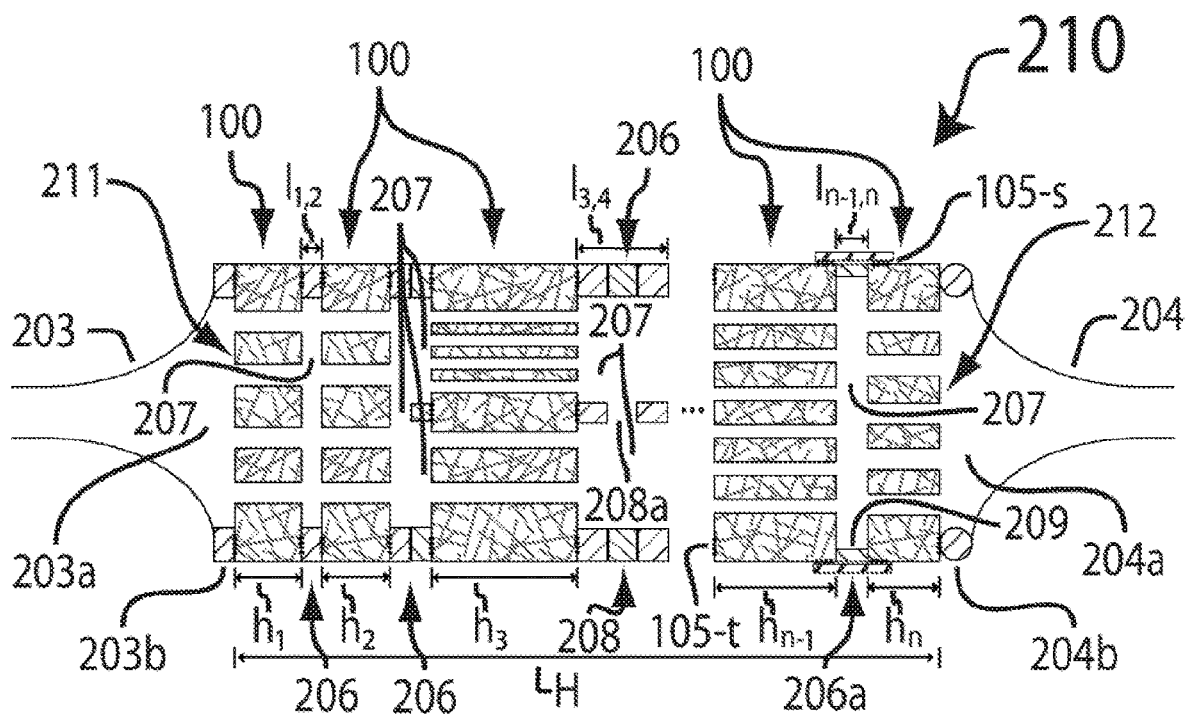
FIG. 8 shows a reactor core formed by a serial arranged stack of reactor core elements, resulting in a reactor core stack.

A reactor core 200 in accordance with this disclosure has a reactor core input surface 201 and a reactor core output surface 202 and includes at least one reactor core subcomponent 250. A reactor core subcomponent 250 can be selected from the group comprised of (i) a reactor core element 100, (ii) a reactor core stack 210, (iii) a parallel reactor core stack 230, and (iv) a serial and/or parallel connected combination thereof. At least one sealed reactor core primary fluid input manifold 203 having at least one reactor core primary fluid input line 203a is connected in a sealed manner to the reactor core input surface 201 through a seal 203b. At least one reactor core primary fluid output manifold 204 having at least one reactor core primary fluid output line 204a is connected in a sealed manner through a seal 204b to the reactor core output surface 202. FIG. 8 shows the not intended to be limiting examples of seals 203b and 204b in the form of a single sheet gasket and an O-ring as an alternative to semi-flexible or rigid "glue" or plastic molded type seals discussed above.

When multiple primary fluid input manifolds 203 are connected to a reactor core input surface 201, no primary fluid input lines 203a are connected to the same sealing zone of the reactor core input surface 201. However, each primary fluid input manifold 203 can be connected through one or more primary fluid input lines 203a to multiple sealing zones, if they are available. When multiple primary fluid output manifolds 204 are connected to the reactor core output surface 202, no primary fluid output lines 204a are connected to the same sealing zone of the reactor core output surface 202. However, each primary fluid output manifold 204 can be connected through one or more primary fluid output lines 204a to multiple sealing zones, if they are available. The number of primary fluid output manifolds 204 can be also less or more than the number of primary fluid input manifolds 203, i.e. when the output from different primary input fluids is combined or split into a common primary output fluid for special fluid reactor unit applications where such a setup is beneficial.

In embodiments, the reactor core 200 has multiple primary fluid input manifolds 203 importing the same fluid to the reactor core input surface 201. In other embodiments, different fluids are imported into the reactor core input surface 201. In embodiments, the reactor core 200 has multiple primary fluid output manifolds 204 exporting the same fluid from the reactor core output surface 202. In other embodiments, different fluids are exported from the reactor core output surface 202. In embodiments, the number of primary fluid input manifolds 203 and primary fluid output manifolds 204 are identical. In other embodiments, there are more primary fluid input manifolds 203 than there are primary fluid output manifolds 204. In yet other embodiments, there are less primary fluid input manifolds 203 than there are primary fluid output manifolds 204.

The sum of all secondary fluid external contact surfaces of all of the available reactor core elements 100 from which a reactor core 200 is made, is the reactor core secondary fluid external contact surface. By using one or more suitable gaskets, O-rings, epoxy seals, caulking means, plastic molds, or other sealing means, the secondary fluid external contact surface may be separated into at least two separate outer surfaces, a reactor core secondary fluid input surface and a reactor core secondary fluid output surface (see FIG. 10A). For the case where the reactor core 200 includes only a single reactor core element 100 (see FIGS. 1A and 1B), its reactor core element input surface 101 is also the reactor core input surface 201 and its reactor core element output surface 102 is also the reactor core output surface 202. Similarly, its secondary fluid external input surface is also the reactor core secondary fluid input surface 246 and its secondary fluid external output surface is also the reactor core secondary fluid output surface.

In embodiments, to increase the primary output fluid production output capacity of a reactor core 200 over the maximum delivery capacity of a single reactor core element 100, multiple reactor core elements 100 are combined, for example into reactor core subcomponents 250 and one or more subcomponents 250 can be serially and/or parallelly combined into a reactor core 200. When multiple reactor core elements 100 together form a reactor core 200, at least some of the available sealing zones of the output surface 102 or the input surface 101 of each individual reactor core element 100 can be connected to the available sealing zones of the input surface 101 and/or output surface 102 of another reactor core element 100 in a sealed manner. Three primary connection schemes are envisioned for this: serial, parallel, and a combination of serial and parallel.

FIG. 8 shows the special, not intended to be limiting, case of a reactor core 200 in the form of a reactor core stack 210 made from a combination of simple and complex reactor core elements 100 having single and multiple sealing zones 105-t, as well as 105-s, that have been stacked in series, with a single reactor core primary fluid input manifold 203 that is sealed against the reactor core stack input surface 211 with a seal 203b in the form of a sheet gasket and with a single reactor core primary fluid output manifold 204 that is sealed against the reactor core stack output surface 212 with a seal 204b in the form of an o-ring.

The input surface of the first reactor core element 100 is also the reactor core stack input surface 211. The output surface 102 of the n-th and last reactor core element 100 is also the reactor core stack output surface 212.

The reactor core stack 210 has a total height H and includes at least two reactor core elements 100 arranged in series. FIG. 8 shows an embodiment where multiple individual i-th reactor core elements 100 with an average height $h_i$ are connected in a sealed manner in series through at least one primary fluid connection line manifold 206 which connects to input surface 101 and output surface 102 in a sealed manner, thereby defining sealing zones (all depicted in FIG. 8 as a thick black line with 4 cross lines), herein depicted as 105-t and 105-s type sealing zones. Each primary fluid connection line manifold 206 has an average length $l_{j,\ j+1}$, where j=1, 2, . . . , n–1, and where n>1 is defined as the maximum number of reactor core elements 100 connected in series for a given reactor core stack 210. For each reactor core element 100 pair at least one internal reactor core element primary fluid line 207 lines up with at least two neighboring fluid channel zones 103. In embodiments, any sealing zone seals on a reactor core element 100 help to prevent undesired primary fluid and secondary fluid flow into or outside of their designated spaces up to a rated pressure limit. In embodiments, seals connecting an input surface 101 with an output surface 102 may also serve to seal up any perforations (whether intentionally or unintentionally created) in the open-pore cellular network material 150 that are located directly underneath the seals and are undesirable for the anticipated use of the reactor core 200. Such an embodiment allows lower tolerances for locating a sealing zone with respect to a given reactor core element 100, typically without losing any significant productivity rate for a given reactor core element 100.

In embodiments, a special version of a primary fluid connection line manifold 206, indicated as primary fluid connection line manifold 206a in FIG. 8, is used to create two 105-s type sealing zones. Primary fluid connection line manifold 206a can be used in conjunction with a spacer 209, as depicted in FIG. 8, to separate neighboring reactor core elements 100 and create the primary fluid line 207. Alternatively, an elongated primary fluid connection line manifold 206a may be used alone to separate neighboring reactor core elements 100 and create the primary fluid line 207. Without such spacer 209 or elongated primary fluid connection line manifold 206a, two serially arranged reactor core elements 100 would be in direct contact with one another, which may cause fluid flow problems, especially when the reactor core elements 100 are not identical, since the different fluid channel zones 103 and fluid channels 104 may not align with each other. In other embodiments, a special primary fluid connection line manifold 206 is used (not shown in FIG. 8) to create a 105-c type sealing zone. These last two embodiments allow for larger fluid channel zones 103 for reactor core elements 100 having a given fixed physical size; specifically, the size of the fluid channel zone 103 is increased by about the amount of space a top or bottom located sealing zone 105-t would have taken up.

This serial and sealed arrangement of the reactor core elements 100 allows at least one primary input fluid to flow through the reactor core stack 210. For each available primary input fluid, its chemical composition will be altered within the multitude of fluid channels 104 inside each fluid channel zone 103 through the delivery and/or extraction of one or two secondary fluids that is/are common to all reactor core elements 100 inside a reactor core stack 210, thus transforming each of the available primary input fluids into a primary output fluid. Optionally, more than one primary output fluid can be combined into fewer or a single primary output fluid at any primary fluid connection line manifold 206 along the reactor core stack 210 or at the primary fluid output manifold 204. Furthermore, this arrangement allows a single tall reactor core element 100 to be substituted with multiple, shorter reactor core elements 100 having a height $h_i \leq H$ and with $\Sigma_{i=1}^{n} h_i = H$. This is especially beneficial when a desired taller, single reactor core element 100 with h=H cannot be manufactured economically, or where it is otherwise beneficial to utilize a series of shorter reactor core elements 100 instead. If complex-shaped reactor core elements 100 are used to build a reactor core stack 210 that incorporates at least one secondary fluid channel 132, as illustrated in FIG. 2A, such secondary fluid channels 132 can be used to feed/extract a secondary fluid selectively to/from the gap between each reactor core element 100 inside its respective sealing zone, thus possibly providing higher system performance than an equivalently tall simple-shaped single reactor core element 100 element could provide.

In embodiments, multiple reactor core elements 100 having the same and/or different fluid channel 104 arrangements are stacked together to form a reactor core stack 210. For example, the stacking of reactor core elements 100 with different fluid channel 104 arrangements can be used to optimize the processing capacity for a given reactor core 200, when the composition of the primary fluid is changing in a predictable manner (for example, primary fluid concentration changes) when flowing from one reactor core element 100 to the next.

Each primary fluid connection line manifold 206 contacts a reactor core element input surface 101 and reactor core element output surface 102 inside the respective sealing zones in a sealed manner. In addition, at least near these input and output surfaces 101 and 102, the primary fluid connection line manifold 206 has an internal primary fluid line 207 for each individual fluid channel zone 103 which is not smaller than the fluid channel zone 103 and optionally is as big as the inside edge 107 of the sealing zone. In further embodiments, at least for part of the length $l_{j,\ j+1}$ of the primary fluid connection line manifold 206, the outputs of all available fluid channels 104 merge into a single primary fluid line 207, as shown for example in FIG. 8 for the primary fluid connection line manifold 206 with the length $l_{3,4}$. This can help to homogenize the primary fluids and thereby increases the primary output fluid production capacity.

In embodiments, the primary fluid connection line manifolds 206 are single sheet gaskets with appropriate vertical perforations for all available fluid channel zones 103, as shown in FIG. 8 for the primary fluid connection line manifold 206 with the length $l_{1,2}$. In other embodiments, a reactor core element primary fluid distribution plate 208 is sandwiched between two appropriately cut-out single sheet gaskets, as indicated in FIG. 8 for the primary fluid connection line manifold 206 with the length $l_{3,4}$. The primary fluid distribution plate 208 can optionally include at least one primary fluid line 208a that flows perpendicular to direction of the primary fluid lines 207, allowing the primary fluid from multiple primary fluid lines 207 to mix. Such single sheet gaskets may be made of a sufficiently compliant sheet material (for example, natural rubber, silicone rubber, Viton, PTFE, PVDE, acrylic latex rubber, etc.) that is inert to all the fluids to which a given reactor core 200 is exposed, and that under compression (to assure sealing against perfectly or imperfectly flat sealing zones) and over the intended use time does not significantly encroach (flow) over the outer edge 108 of the respective fluid channel zone 103, thus chocking fluid flow of nearby fluid channels 104. In alternative embodiments, at least one of the seals and/or primary fluid connection lines is not flexible, for example, made from localized cured epoxy.

A possible adaptation from one fluid channel 104 layout design to another is depicted in FIG. 8 between the second and third reactor core elements 100 with two single sheet gaskets that have different cutouts for the respective sealing zones 105-t (not specifically marked in FIG. 8), thus allowing the switch from a single sealing zone to a multiple sealing zone reactor core element 100 layout arrangement, and vice versa. When a primary fluid distribution plate 208 that has an appropriate arrangement of at least one internal primary fluid line 208a is sandwiched between two single sheet gaskets, as shown between a third and fourth reactor core elements 100 in FIG. 8, the flow from different sealing zones can be redirected, combined, redistributed, and otherwise rearranged.

In embodiments, rigid or flexible lines are used as primary fluid connection line manifolds 206 with appropriate sealing means at their ends, including glues or caulking means, that form a temporary and/or permanent seal with sealing zones, optionally after an appropriate curing/heating and/or other sealing/gasket forming processing tasks. In still further embodiments, printable, sprayable, squeezable, meltable, or curable powders, gels, pastes, one or multi-part epoxy formulations, monomers, caulks, or other sealing forming material or materials are delivered to sealing zones in a predetermined quantity, and then transformed into a desired conformal sealing primary fluid connection line manifold 206 through appropriate curing, activating, heating, and other forming means, thus forming a temporary and/or permanent gasket-like seal and, thereby, the effective primary fluid connection line manifolds 206 with its at least one internal primary fluid line 207.

In embodiments, the heights $h_i$ of all the respective reactor core elements 100 are within a given tolerance band, for example ±100 μm, or ±50 μm, or ±25 μm, or ±12 μm. In other embodiments, reactor core elements 100 with different heights are utilized to build a given reactor core stack 210. In still further embodiments of this disclosure, the height of at least one primary fluid connection line manifold 206 is chosen so that the total reactor core stack 210 matches a predetermined height H for a given selection of reactor core elements 100 and primary fluid connection line manifolds 206. This enables the serial stacking and piping of individual reactor core elements 100 that have a different height $h_i$ values, while still obtaining a reactor core stack 210 having a nominal height H. In further embodiments, the final target height H for a reactor core stack 210 is achieved and/or finalized by mechanically compressing the reactor core stack 210 as needed, e.g., by compressing one or more flexible primary fluid connection line manifolds 206 and/or respective seals 203b or 204b.

In embodiments, with appropriate compliant seals contacting the sealing zones, sealed reactor core stacks 210 can be manufactured from reactor core elements 100 having imperfections in their input and output surfaces 101 and 102. In embodiments, the reactor core stacks 210 are built only with reactor core elements 100 having reactor core element input and output surfaces 101 and 102 that are flat and parallel to each other within a given tolerance band. For economic reasons, it is further often desired to find a good balance between the shape tolerance of reactor core elements 100 and their manufacturing yields, the shape and manufacturing tolerances and sealing compliance ranges of the chosen primary fluid connection line manifold 206, and the manufacturing yield for the total reactor core stack 210 assembly process. In embodiments the seal 204b for a reactor core stack 210 is a side or corner seal to a 105-s or 105-c type sealing zone, thus allowing to accommodate for some height variations of the stack 210.

In embodiments, selected surface areas of the reactor core stack 210 are sealed and/or blocked, for example, at least along selected sections of all the sidewalls 129 of all the reactor core elements 100 that form said stack 210 to allow a physical separation between a secondary fluid input surface 246 and secondary fluid output surface 247 and a homogenous secondary fluid flow through the reactor core stack 210, as was discussed above in relation to FIGS. 1A and 1B.

The fluid flow rate $F_{RCS}$ through a single reactor core stack made from at least one simple reactor core element can be derived from the formula $$\frac{1}{F_{RCS}} = \sum_{i=1}^{n} \frac{1}{F_{FCZ}^i} \tag{9}$$

with $F^i_{FCZ}$ defined by equation (2) representing the fluid flow of the i-th simple reactor core element making up the reactor core stack. For the special case of a reactor core stack including identical type simple reactor core elements having N identical round active fluid channels and a height $h_i$ or $h_i$=h equation (9) simplifies to the below formula $$F_{RCS} = \frac{N * \Delta P_{PF} * \pi * \phi_{FC}^4}{128 * \eta_{PF} * H} = \frac{N * \Delta P_{PF} * \pi * \phi_{FC}^4}{128 * \eta_{PF} * n * h} \tag{10}$$

Figure 9:
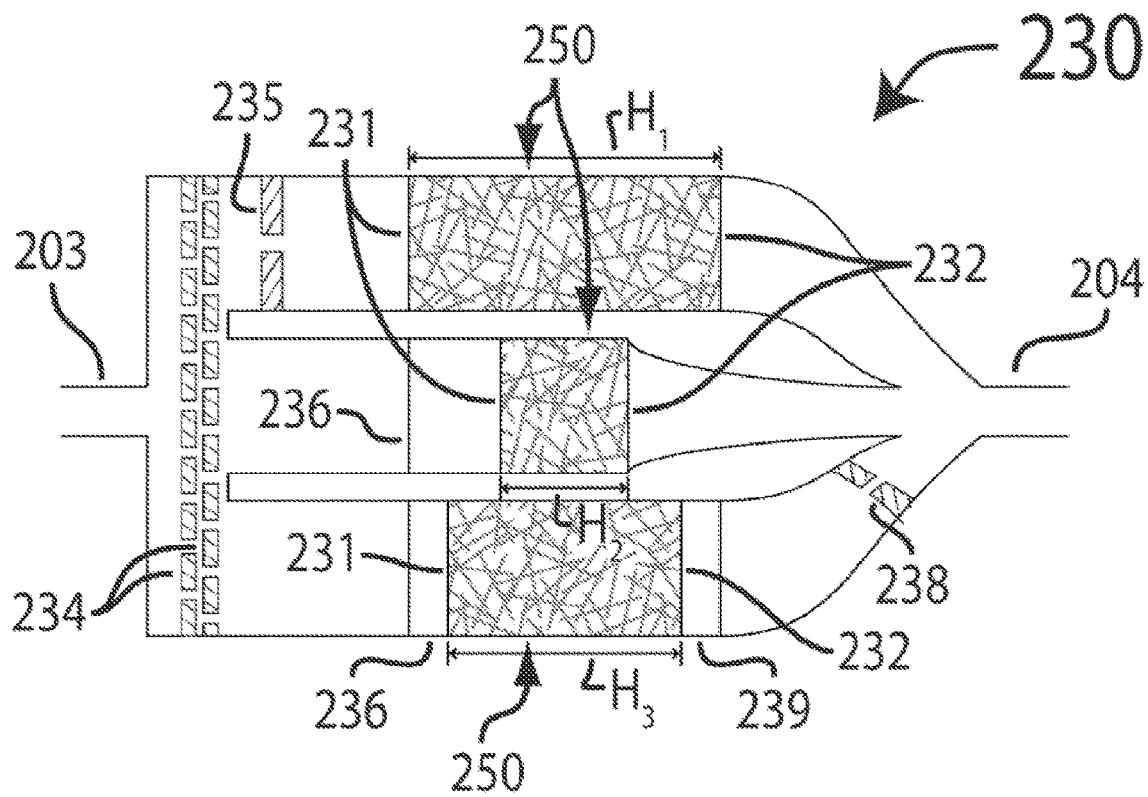
FIG. 9 shows a reactor core formed by a parallel arrangement of reactor core sub-components.

FIG. 9 illustrates a reactor core 200 in the form of a parallel reactor core stack 230 that parallelly connects, through at least one sealed reactor core primary fluid input manifold 203 and at least one sealed primary fluid output manifold 204, at least two reactor core subcomponent 250, each having a height $H_i$ for i=1, 2, . . . , m with m>1 representing the number of individual reactor core elements 100 and/or reactor core stacks 210 that are connected in parallel.

The parallel reactor core stack input surface 231 of a parallel reactor core stack 230 is the sum of the reactor core element input surfaces 101 of the first reactor core elements 100 of the first reactor core subcomponents 250 of each branch of the parallel stack 230. The parallel reactor core stack output surface 232 is the sum of the reactor core element output surfaces 102 of the last reactor core elements 100 of the last reactor core subcomponents 250 of each branch of the parallel stack 230. Where a reactor core 200 includes a single parallel reactor core stack 230, the reactor core input surface 201 is the same as the stack input surface 231 and the reactor core output surface 202 is the same as the stack output surface 232.

FIG. 9 illustrates an embodiment for the case of a primary fluid input manifold 203 suitable for a parallel reactor core stack 230 in the form of a single furcated pipe that connects in a sealed manner to the respective sealing zones enclosing all fluid channel zones 103 of the available reactor core input surface 201. In other embodiments, not shown in FIG. 9, a primary fluid input manifold 203 has a single input flow line that connects to a suitable complex-shaped flat (sheet) gasket at its end having appropriate cutouts for respective fluid channel zones 103, thus allowing the primary input fluid to only flow to all available respective fluid channel zones 103. The gasket is pressed against the input surfaces 101 of the reactor core 200 to obtain a seal and the appropriate gasket-cutouts create the primary fluid input lines 203a for each fluid channel zone 103. The primary fluid input manifold 203 may optionally include at least one internal flow redistribution baffle 234 for improving fluid flow distribution to all fluid channel zones 103, each connected to primary fluid input line 203a. The baffle 234 is one of the tools that can be used to assure appropriate fluid flow into each respective fluid channel zone 103 across a large area, which otherwise could lead to non-uniform primary input fluid flow distributions across all the available fluid channel zones 103. The internal flow redistribution baffle 234, as depicted in FIG. 9, may optionally be included upstream of a split into at least one primary fluid input line 203a of a reactor core primary fluid input manifold 203 and/or downstream at the level of at least one individual input line 203a.

In embodiments, the cross-sectional area of each branch of the primary fluid input manifold 203 is matched to the flow resistance and capacity of each connected subcomponent 250. In further embodiments, an optional input flow adjuster 235 is installed in-line with at least one branch of the primary fluid input manifold 203 to balance the respective primary input fluid flow distribution to the subcomponents 250. Such flow adjusters 235 can include a fixed or adjustable orifice, a needle valve, a sintered component, single or multiple optional offset patterned flow baffles, an adjustable butterfly valve, or combinations thereof.

FIG. 9 additionally shows a primary fluid output manifold 204 as a different shaped furcated pipe with smooth cross-sectional shape and/or size changes. Alternatively, an output flow adjuster 238 in-line with at least one branch of the primary fluid output manifold 204, i.e. after a fluid channel zone 103 of the reactor core output surface 202, is also considered for this embodiment.

FIG. 9 further shows the case where a shorter subcomponent 250 is preceded by an optional length adjusting sealed primary input fluid delivery line 236 that connects in a sealed manner to a branch of the primary fluid input manifold 203 and where a shorter subcomponent 250 is followed by an optional height adjusting sealed primary output fluid delivery line 239 that connects to a branch of the primary fluid output manifold 204 so that, optionally, at least (i) two subcomponents 250 connecting to branches of the primary fluid output manifold 204 terminate at the same height. Alternatively, rather than using a height adjusting sealed line 239, a shorter subcomponent 250 could be connected to a longer branch of the primary fluid output manifold 204, as also indicated in FIG. 9. In further embodiments, flexible primary fluid input or output connection lines are used.

In embodiments, each available primary fluid input manifold 203 and/or a primary fluid output manifold 204 can be a complex-shaped object (for example, cast or molded rigid, semi-flexible, or flexible manifold with a sealing gasket or other sealing means as discussed above; or a flexible molded rubber manifold with or without sealing gasket or auxiliary sealing means, such as a glue layer) that can include, in a sealed manner, one or more separate lines for delivering and/or extracting a secondary fluid to/from one or more secondary fluid channel 132. Optionally, at the end of a primary fluid input manifold 203, a flow redistribution plate sandwiched between appropriate gaskets having appropriate internal flow channels can be put before the input surfaces 201 to assure balanced primary input fluid flow to its respective fluid channel zone 103 and/or to deliver/remove a secondary fluid to at least one internally located secondary fluid channel 132. Similarly, a flow redistribution plate sandwiched between appropriate gaskets or rigid sealing means having appropriate internal flow channels can be used on the reactor core output surface 202 to allow also for delivery/extraction of a secondary fluid.

In further embodiments, as discussed above for the reactor core stack 210, part of the individual reactor core elements 100 that form the reactor core subcomponents 250 can be sealed off to allow a sealed separation between an input secondary fluid and an output secondary fluid flow, thus creating a reactor core secondary fluid input surface 246 and a secondary fluid output surface 247 (not shown in FIG. 9).

The primary input fluid flow rate $F_{PRCS}$ through a single parallel reactor core stack made from subcomponents, which themselves are made of reactor core elements with negligible primary fluid loss through the fluid channel sidewalls, can be calculated with the formula $$F_{PRCS} = \Sigma_{k=1}^m F^k_{RCPE} \quad (11)$$

with $F^k_{RCPE}$ being the primary input fluid flow through the k-th subcomponent of the parallel reactor core stack. For the special case where a reactor core includes a single parallel reactor core stack which parallelly connects (i) m reactor core stacks, each having n simple reactor core elements or (ii) m simple reactor core elements (n=1), with each reactor core element having N identical active fluid channels with low primary fluid flow loss through their sidewalls and a height $h_{i,k}$ for the i-th reactor core element in the k-th subcomponent and with and $h_{i,k}=h$, equation (11) simplifies to the below formula $$F_{PRCS} = \sum_{k=1}^m \frac{m*N*\Delta P_{PF}*\pi*\phi^4_{FC}}{128*\eta_{PF}*H_k} = \frac{m*N*\Delta P_{PF}*\pi*\phi^4_{FC}}{128*\eta_{PF}*n*h}. \quad (12)$$

In embodiments, a simple reactor core 200 includes one reactor core element 100. In embodiments, a complex reactor core 200 includes at least two reactor core subcomponents 250, where these subcomponents 250 are arranged in series, in parallel, or in some combination thereof in a sealed and connected manner.

Those skilled in the art will understand that this disclosure is intended to include all obvious extensions and variations of the various connection schemes depicted and discussed here. Similarly, variations and derivations of the formulas discussed herein, as necessary to build such varying complex reactor cores 200 for particular fluid reactor applications, including, amongst others, formulas to establish flow rates and other performance-related parameters, are also intended to be included in this disclosure.

Fluid Reactors

Figure 10C:
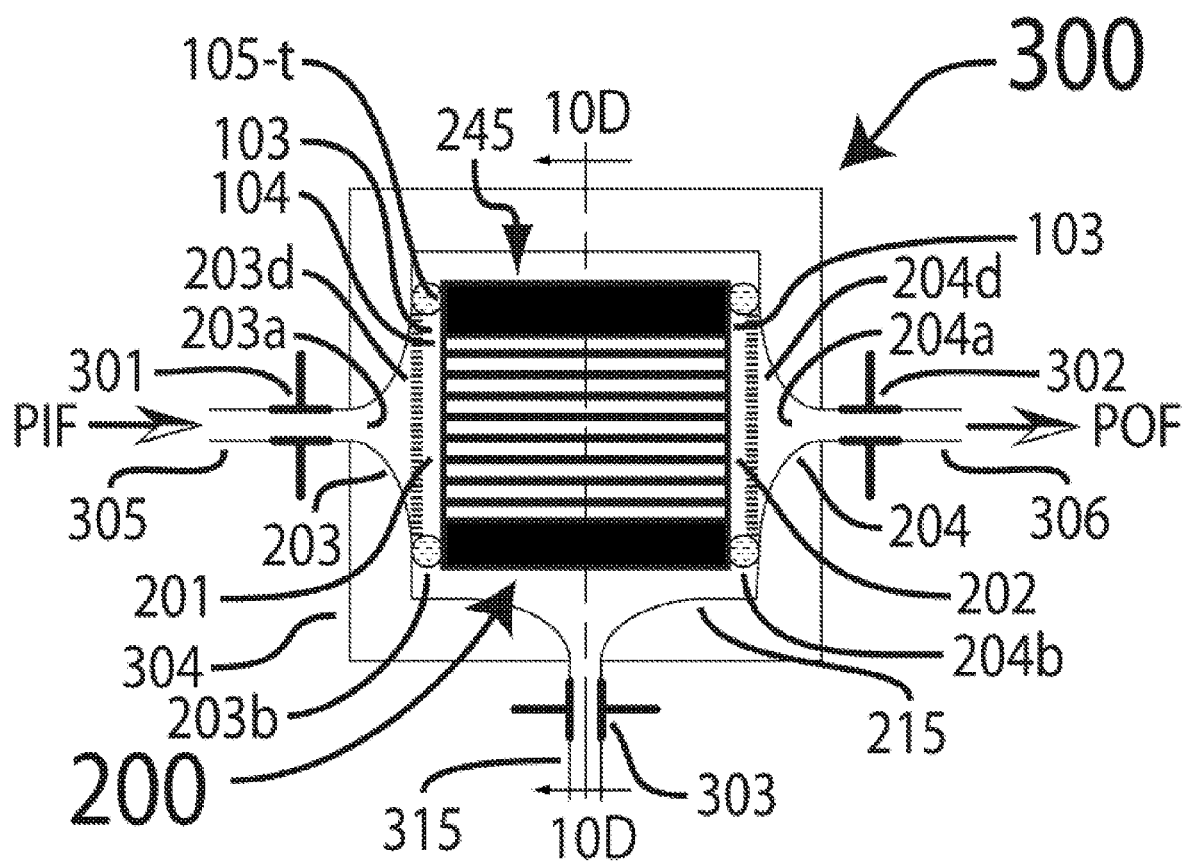
Figure 10D:
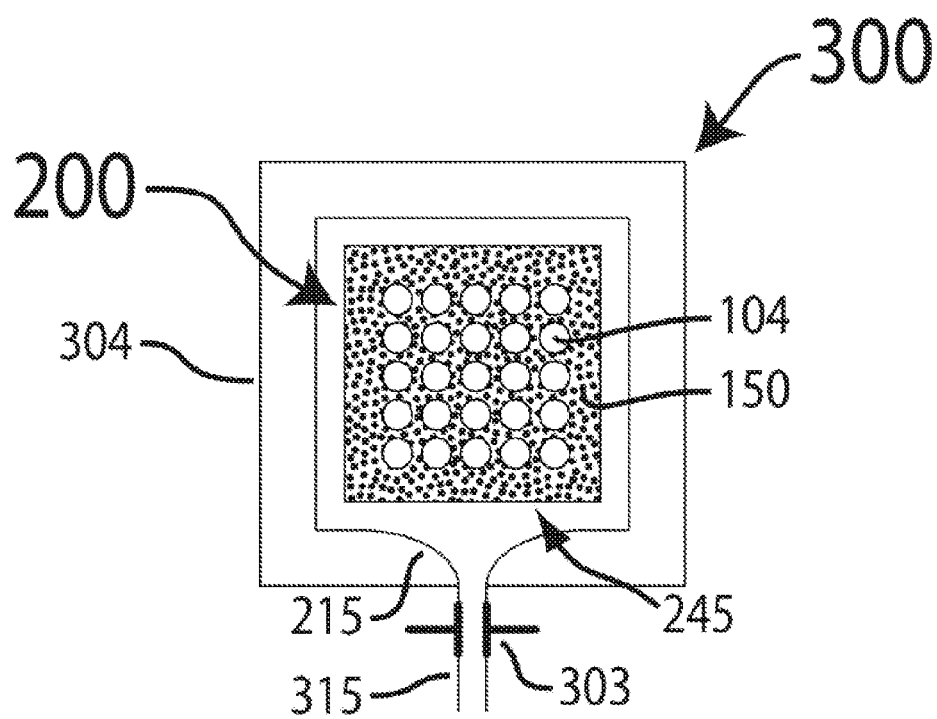

The simplest embodiment of a fluid reactor is a single fluid reactor unit 300 that transforms at least one primary input fluid into a primary output fluid with the aid of one or two secondary fluids. FIGS. 10A and 10C schematically shows a cross-section parallel to, and FIGS. 10B and 10D shows a cross-section perpendicular to, the primary fluid flow direction of a fluid reactor unit 300. Each fluid reactor unit 300 has at least one primary fluid input port 301, at least one primary fluid output port 302, and one or two secondary fluid ports 303 attached in a sealed manner to a single fluid reactor unit housing 304 that isolates an enclosed reactor core 200 from the environment. FIGS. 10A and 10B depict an embodiment of a four-port fluid reactor, while FIGS. 10C and 10D depict an embodiment of a three-port fluid reactor.

In many cases, a fluid input and/or output port is a flanged sealable connection port for mechanically connecting a rigid fluid line with a sealing gasket and/or O-ring in a semi-permanent way, or it is a suitable sealable hose connector, for example a barbed connector, for a temporary or permanent connection to a flexible fluid line. The sealing can be done by applying a mechanical force to an at least partially compliable sealing material, e.g., a polymer, metal or Grafoil-based gasket, an O-ring, or a flexible hose or tube end. Other sealing means within the purview of those skilled in the arts are also considered, like gluing, welding, soldering, molding, epoxying, compression fitting, swaging, quick connects. Teflon tape aided threaded seals, compression fitting seals, threaded seals, conical seals, ball and socket seals are viable options as well if they are compatible with the fluid flow through the port and/or fluid reactor unit 300.

Each primary input fluid arrives at the primary fluid input port 301 of the fluid reactor unit 300 through a primary fluid input line 305. Each available chemically altered primary output fluid leaves the fluid reactor unit 300 from a primary fluid output port 302 through a primary fluid output line 306.

Each primary fluid input port 301 is a sealable mechanical fluid interface (connection port) between an outside primary fluid input line 305 and a respective reactor core primary fluid input manifold 203 that delivers the primary input fluid to at least one respective fluid channel zone 103 at the input surface 201 of a reactor core 200. Similarly, the primary fluid output port 302 is a sealable mechanical fluid interface between the outside primary fluid output line 306 and the primary fluid output manifold 204 that collects a primary output fluid from at least one fluid channel zone 103 at the output surface 202 of a reactor core 200. Each primary fluid input and output manifold 203 and 204 contains at least one end sealable primary fluid input and output line 203a and 204a, respectively, through which the primary fluids of fluid reactor unit 300 are flowing to or from respective fluid channel zones 103. Each primary fluid input line 203a of a given primary fluid input manifold 203 has a sealed connection at a sealing zone of the input surface 201 of reactor core 200 as discussed above. Similarly, each primary fluid output line 204a of a primary fluid output manifold 204 has a sealed connection at a sealing zone of the respective output surface 202. FIG. 10A shows the example of seals 203b and 204b used to seal input surface 201 to input manifold 203 and to seal the output surface 202 to the output manifold 204, respectively, thus defining sealing zones at the interfaces, as discussed above.

An available secondary fluid port 303 can either be a secondary fluid input port 311 or a secondary fluid output port 312. The secondary fluid port 303 is a sealed mechanical fluid interface between an external secondary fluid line 315 and a secondary fluid manifold 215. The secondary fluid line 315 may be either a fluid input line 313 or a fluid output line 314; similarly, the secondary fluid manifold 215 can be either a fluid input manifold 213 or a fluid output manifold 214. A secondary fluid input port 311, when present, is a sealed mechanical fluid interface between a secondary fluid input line 313 and a secondary fluid input manifold 213 through which a secondary input fluid gets delivered to the secondary fluid input surface 246. Similarly, when present, a secondary fluid output port 312 is a sealed mechanical fluid interface between an external fluid reactor unit secondary fluid output line 314 and a reactor core secondary fluid output manifold 214 which collects any available secondary output fluid from a secondary fluid output surface 247.

For readability of the drawings, a reactor core 200 is depicted in FIGS. 10A through 10D in the form of a single and simple reactor core element 100 with a single primary input fluid, primary output fluid, and fluid channel zone 104, i.e. the case of a simple reactor core 200. As discussed above, each of the reactor core elements 100, of which a reactor core 200 is made of, is a substrate-free object made from an open-pore cellular network material 150 having a bi-continuous tortuous phase structure (shown in FIG. 10A with a solid black background and in FIG. 10B with a dotted background) and has an input surface 101 and an output surface 102 that has at least one, substantially parallel to each other, aligned group (or array) of perforating fluid channels 104 located between them. Each of the groups of fluid channels 104 is located inside a respective fluid channel zone 103 which is surrounded by a sealing zone 105-t located at and/or near the reactor core element input surface 101 and reactor core element output surface 102 of said reactor core elements 100. Alternatively, sealing zones 105-c, 105-s, or a combination of the different types of sealing zones could be used rather than just 105-t type sealing zones.

E, N, S, PM, and M-type reactor core elements 100 can be used to build reactor cores 200. Inside the fluid channels 104 of the reactor core elements 100 of which such a reactor core 200 is made, all primary input fluids of the fluid reactor unit 300 get converted, through at least one chemical composition change, to respective primary output fluids while traveling through the fluid channels 104 and while absorbing a secondary input fluid and/or releasing a secondary output fluid through the porous sidewalls 125 of the fluid channels 104. The sidewalls 125 have asymmetric fluid transfer properties for secondary fluids and at least one component of the primary fluids. Additionally, the sidewalls 125 are designed and manufactured to enhance at least the spatial confinement properties of at least one component of the primary fluids of the reactor core elements 100.

FIGS. 10A and 10B depict a four-port fluid reactor with two secondary fluid ports 303 where the secondary fluid external contact surface 245 is separated into a secondary fluid input surface 246 and a secondary fluid output surface 247 at a minimum through appropriate sealing means 308 (for example, from the non-intended to be limiting group of a sheet gasket, an O-ring, a caulking, a plastic molding, a solder, an epoxy seal, etc.) which connect, in a sealed manner, the secondary fluid input manifold 213 to the secondary fluid input surface 246 and/or the secondary fluid output manifold 214 to the secondary fluid output surface 247. FIG. 10B shows an additional embodiment where additional sealing means 309, represented here as two thick lines, are applied to the left and right sidewalls 129 of reactor core elements 100 to make E-type reactor cores 200 made of only E-type reactor core elements 100, and as discussed above. Together housing 304, seals 203b and 204b, and optional seals 308 and 309, isolate the secondary fluid input surface 246 from the secondary fluid output surface 247. Therefore, for the embodiments of FIGS. 10A and 10B, the only way a secondary input fluid can become a secondary output fluid, i.e. the secondary input fluid can reach the sidewalls 125 from secondary fluid input port 311 and the secondary output fluid can reach secondary fluid output port 312 from the sidewalls 125, is by traveling through the open-pore cellular network material 150. FIGS. 10C and 10D depict a three-port fluid device where secondary fluid port 303 can be either a secondary fluid input port 311 or output port 312, depending on the application. In such embodiments, the secondary fluid external contact surface 245 is connected to the single secondary fluid port 303 in a sealed manner with the sealed isolation arising from the seals 203b and 204b between reactor core 200 and housing 304. When the secondary fluid port 303 is an input port, a secondary fluid input must travel from the input port through the open-pore cellular network material 150 to reach the sidewalls 125. Similarly, when the secondary fluid port 303 is an output port, a secondary output fluid can leave the sidewalls 125 and reach the output port only by traveling through the open-pore cellular network material 150.

When more spatially isolated surfaces are available (see FIGS. 2A and 2B), the secondary fluid input surface 246 and/or secondary fluid output surface 247 is chosen in embodiments to optimize the efficiency of a single fluid reactor unit 300 for a targeted application. In embodiments, some of the secondary fluid external contact surface 245 can intentionally be sealed closed (for example, as indicated with thick black lines on the left and right side of the reactor core 200 in FIG. 10B) to facilitate the secondary fluid flow through each reactor core element 100 and to isolate secondary input fluid from secondary output fluid flows, when both are available and the respective fluid reactor application requires it.

FIGS. 10A through 10D show embodiments where reactor core primary fluid input manifold 203 and primary fluid output manifold 204 contain just one primary fluid input line 203*a* and primary fluid output line 204*a*, respectively, through which the primary fluids of reactor unit 300 are flowing to or from a fluid channel zone 103. As discussed above, each primary fluid input manifold 203 can include at least one primary fluid input line 203*a* and/or each primary fluid output manifold 204 can include at least one primary fluid output line 204*a*. In embodiments, the at least one primary fluid input line 203*a* and/or primary fluid output line 204*a* includes at least one flow restriction, pressure plate, or other passive flow redistribution means 203*d* or 204*d* (shown as thick fine dashed lines in FIGS. 10A and 10C) to assure uniform delivery and/or collection of primary fluid to and/or from fluid channel zones 103.

In embodiments, at least one auxiliary sealed line inside housing 304 that is part of a secondary fluid manifold 215 is used to connect a secondary fluid port 303 to at least one secondary fluid channel 132, when available. Optionally, when at least one secondary fluid channel 132 is available, at least one fluid flow redistribution manifold 203*d* or 204*d* is used at the reactor core side of primary fluid input manifold 203 or the primary fluid output manifold 204 or at least one primary fluid distribution plate 208 inside a reactor core stack 210 is used, when available, that includes at least one sealed auxiliary passage suitable for secondary fluid flow (line, hose, pipe, etc.) that allows connecting in a sealed manner to secondary fluid channels 132. Such a fluid flow redistribution manifold 203*d* or 204*d* and/or primary fluid distribution plate 208, when available and used for secondary fluid delivery and/or collection, form part of secondary fluid manifold 215, but at the same time also form part of primary fluid input manifold 203 or primary fluid output manifold 204.

Dynamically Self-Adjusting Fluid Reactor Units

In embodiments of an fluid reactor unit 300, a dynamically self-adjusting fluid reactor unit (DSAFRU) 320 includes (i) a fluid reactor unit 300, (ii) at least one sensor 325 connected to an input and/or output manifold or to the housing 304, (iii) at least one regulator (R) 326 or controller (C) 327 connected to an input and/or output manifolds or to housing 304, and (iv) at least one control box (CB) 328 or master control box (MCB) 329 connected electrically or by other means enabling the receipt and/or transfer of a control or output signal to sensor 325 and regulator 326 or controller 327. The control box 328 and/or master control box 329 interacts with at least one regulator 326 or controller 327 to minimize the difference between the present value (PV) of a sensor 325 and a target output value (TOV) over time.

The regulator 326 changes its output state in direct dependence of an input signal without the use of a feedback signal and can be selected from the non-intended to be limiting group of on/off valve; contactor; relay; SCR regulator; proportional valve; flow regulator; pressure regulator; vacuum regulator; heat exchanger; induction coil; lamp; or, visible, IR, FIR, microwave, or other electromagnetic energy emitters, (also called heaters herein).

The controller 327, over time, minimizes the difference between the present value and the target output value within the system's compensation capability range, independent of any other system inputs. Controller 327 can be at least one of element of the non-intended to be limiting group including mass flow controllers; liquid flow controllers; pressure controllers; on-off controllers based on high/low limits; flow or pressure regulating valve controllers; butterfly valve; proportional valve or adjustable orifice controllers; pump output speed; flow or pressure controllers; temperature controllers; heating/cooling system controllers; visible, IR, FIR lamps or induction or microwave power output controllers; PID controllers; on/off relay controllers; SCR controllers; digital, analog, FGA, microprocessor, or mechanically powered controllers; RS232, Ethernet, WIFI, Bluetooth, IR, microwave communication, or other communication enabled controllers.

In dynamically self-adjusting fluid reactor unit 320 embodiments, the sensor(s) 325 measure and report, and control box 329, control boxes 328, controller(s) 327, and regulator 326 together control a fluid variable selected from the non-intended to be limiting group including (i) flow rate, (ii) temperature, (iii) humidity, (iv) total pressure, (v) partial pressure for a selected gas, (vi) concentration of selected component, (vii) $O_2$ concentration, (viii) $CO_2$ concentration, (ix) blood oxygen saturation, (x) hemoglobin concentration, (xi) salt concentration, (xii) electrical conductivity, and/or (xiii) urea concentration.

Each control box 328 and/or master control box 329 communicates with and/or controls at least one sensor 325, regulator 326, another control box 328, or master control box 329 and optionally receives at least one output signal. In embodiments, when multiple control boxes 328 and/or a master control boxes 329 are available, individual control boxes 328 can operate in at least one control loop mode from the non-intended to be limiting mode-group including (i) receiving a target output value signal and operating dependently on only the present value received from a single sensor 325 and the target output value signal, (ii) operating dependent of a target output value signal received from a target output value from a master control box 329 or another control box 328, (iii) sending a present value signal to another control box 328 or to the master control box 329, (iv) all control boxes 328 are slaves to the master control box 329.

In embodiments, each available master control box 329, control box 328, or controller 327 receives a target output value and controls any connected subsystems receiving a single feedback present value signal from a sensor 325 in such a manner that, on average, the difference between each present value and target output value is minimized over time. Without intending to be limiting, at least one of the target output values can be derived from (i) the output of a different control box 328 or a master control box 329, (ii) a separate demand sensor (DS), (iii) a formula output value dependent on at least one measured and/or communicated input variable (IV), (iv) a forecasted time dependent demand table, (v) a manual entered demands signal, (vi) a remote communicated demand signal (RCDS), and/or (vii) a combination thereof.

Figure 11A:
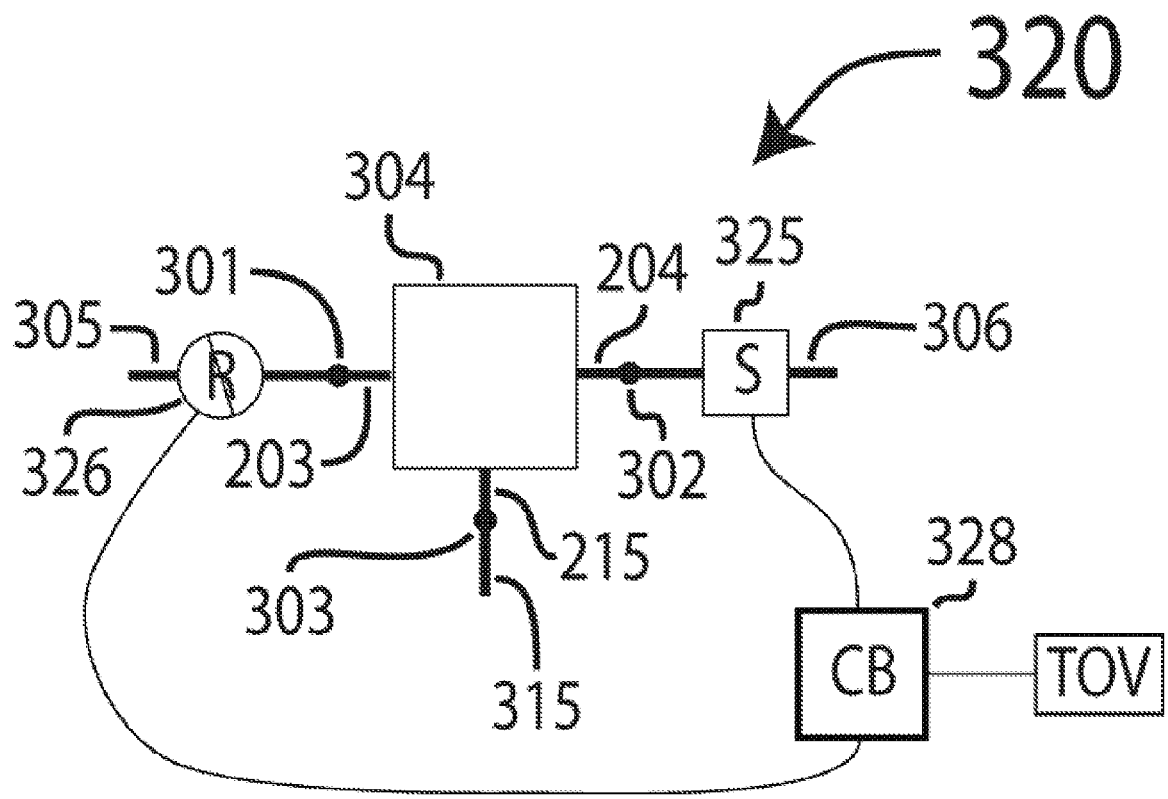
FIG. 11A-D shows a fluid reactor unit in different primary forms of a dynamically adjusting fluid reactor unit with (A) and (B) showing control of the primary fluid path for a three and a four-port device; (C) showing control of the secondary fluid path; and (D) showing control of both primary and secondary fluid paths.
Figure 11B:
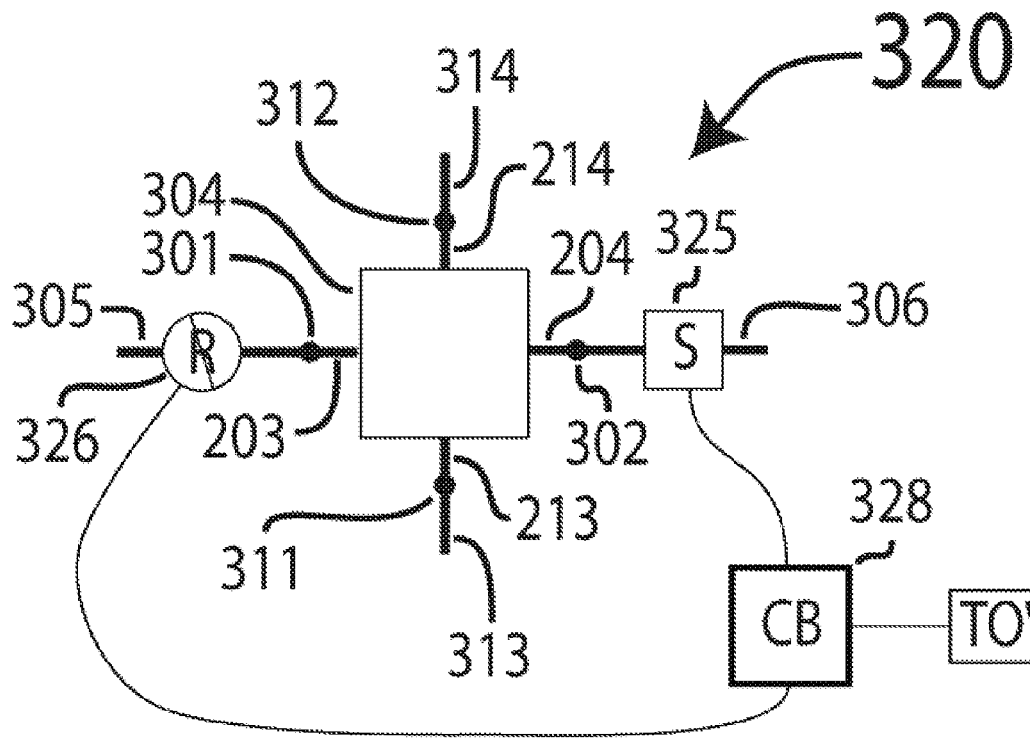
Figure 11C:
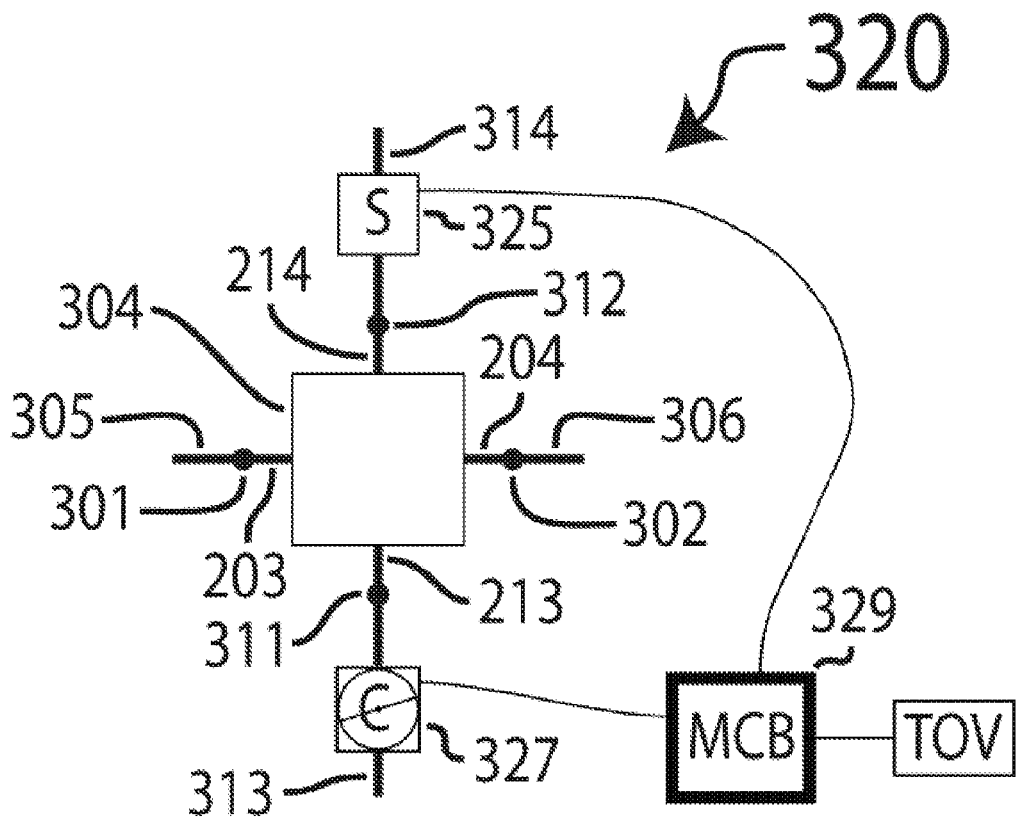

Illustrative, non-limiting embodiments of dynamically self-adjusting fluid reactor units 320 are schematically depicted in FIG. 11A to 11D. FIG. 11A shows an embodiment of a three-port device with a single control loop with a single regulator 326 connected in-line with the primary fluid input line 305 and a sensor 325 connected in-line to the primary fluid output line 306. Both the regulator 326 and the sensor 325 are connected to a control box 328 which receives an external target output value signal. The sensor 325 sends a signal to control box 328 regarding the measured parameters of the primary output fluid and then, if the signal does not match the target output value signal, control box 328 sends a signal to regulator 326 to adjust accordingly, thus forming a control loop. FIG. 11B depicts the same single control loop of FIG. 11A, but in a four-port device. FIG. 11C shows an embodiment of a double control loop with a controller 327 connected in-line with secondary fluid input line 313 and a sensor 325 connected in-line to the secondary fluid output line 314. Both the controller 327 and the sensor 325 are connected to a master control box 329, which receives an external target output value signal and, in connection with the input from the sensor 325, provides a target output value signal for the externally controllable controller 327, thus forming the first control loop. The controller 327 has its own built-in sensor (not shown in FIG. 11C) and together with the target output value signal it receives from the master control box 329 forms its own independent second control loop that is slaved to the first control loop.

Figure 11D:
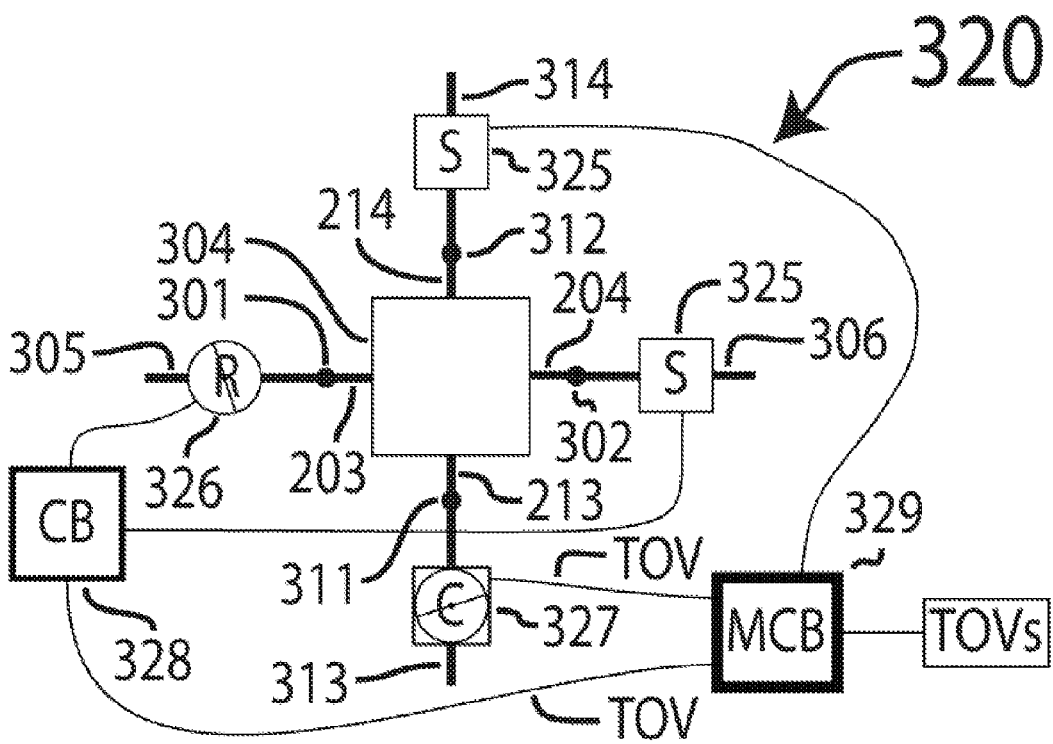

FIG. 11D depicts a control system having three control loops. Specifically, FIG. 11D shows (i) a first control loop including a regulator 326 connected in-line with primary fluid input line 305 that is controlled by a control box 328 that receives a present value output signal from a remote sensor 325 connected in-line with a primary fluid output line 306 and receives its target output value signal from a master control box 329; (ii) a controller 327 connected in-line with secondary fluid input line 313 that receive its target output value from a master control box 329 and that has a built-in sensor 325 (not shown in FIG. 11D), together forming a second control loop; and (iii) a third control loop made of a master control box 329 receiving one or more target output values and a present value output signal from a sensor 325 connected in-line with secondary fluid output line 314 and controlling the controller 327 and control box 328. It should be understood by those skilled in the art reading this disclosure that the control systems depicted in 11A-11D are not the only ways to build a viable control system for a dynamically self-adjusting fluid reactor unit 320 and that various components and configurations could be used in lieu of or in conjunction with those depicted here.

In some dynamically self-adjusting fluid reactor unit 320 embodiments, a control system is used to determine and adjust the temperature of the fluid reactor unit housing 304 or of at least one reactor core element 100 incorporated in the dynamically self-adjusting fluid reactor unit 320. In such embodiments, the temperature may be adjusted using, for example, a heat exchanger system, thermal contact with an external or internal heater, absorption of electromagnetic energy in a suitable spectral range, etc.

Fluid Reactor Unit Connection Pairs

Figure 12A:
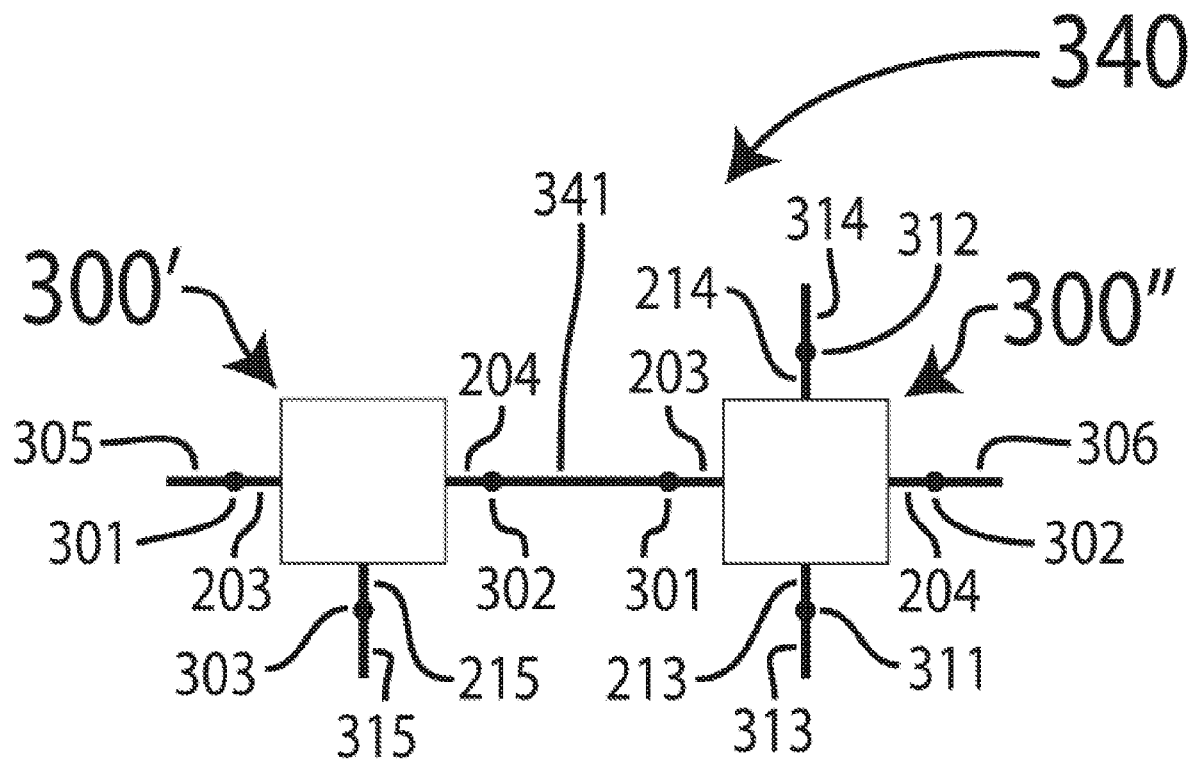
FIGS. 12A-12F shows various fluid reactor unit connection pairs with two single fluid reactor units having (A) a fluid reactor unit primary fluid output port connected in series with a fluid reactor unit primary fluid input port; (B) a fluid reactor unit secondary fluid output port connected in series to a secondary fluid input port; (C) parallel connected primary fluid input ports; (D) parallel connected primary fluid output ports; (E) parallel connected secondary fluid input ports; (F) parallel connected secondary fluid output ports.
Figure 12B:
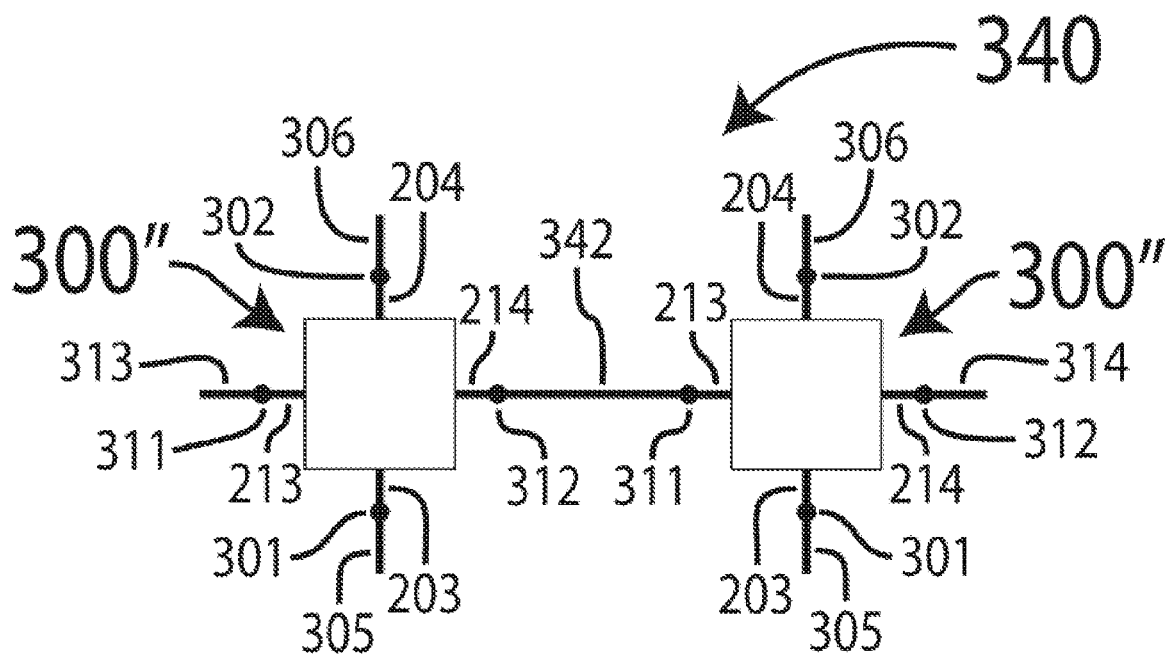
Figure 12C:
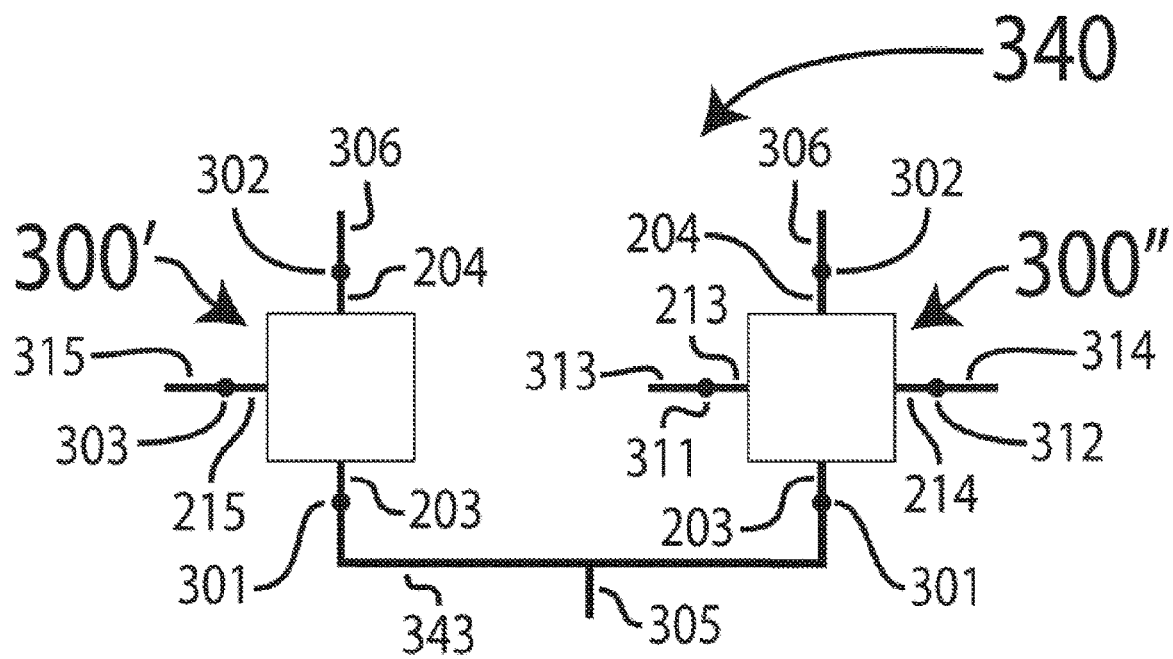
Figure 12D:
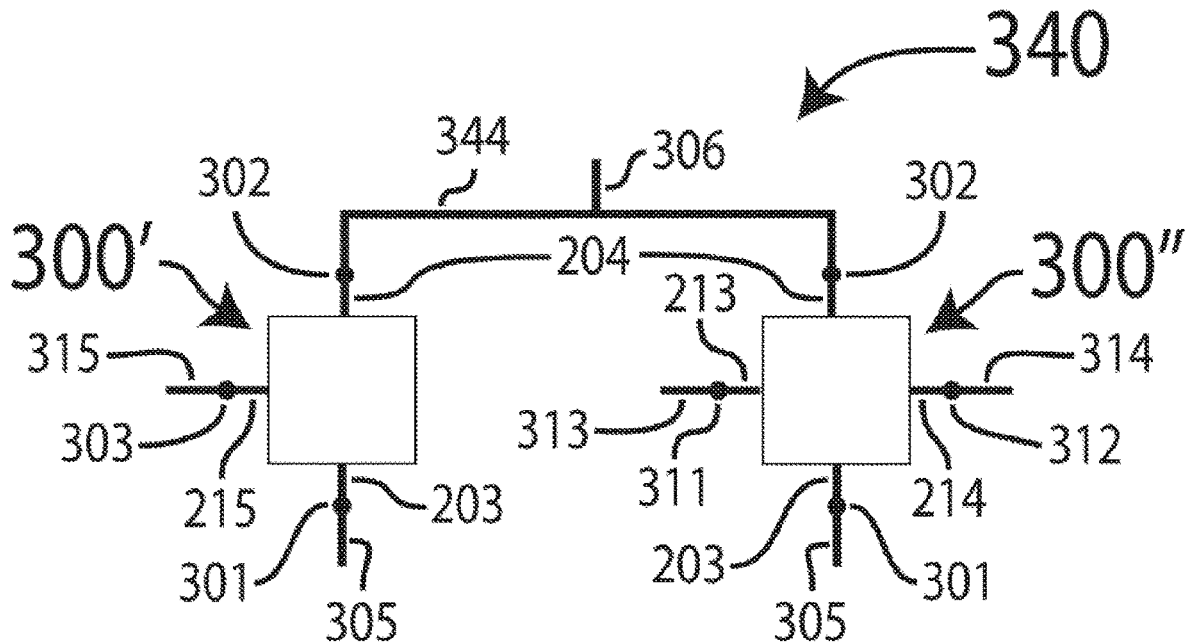
Figure 12E:
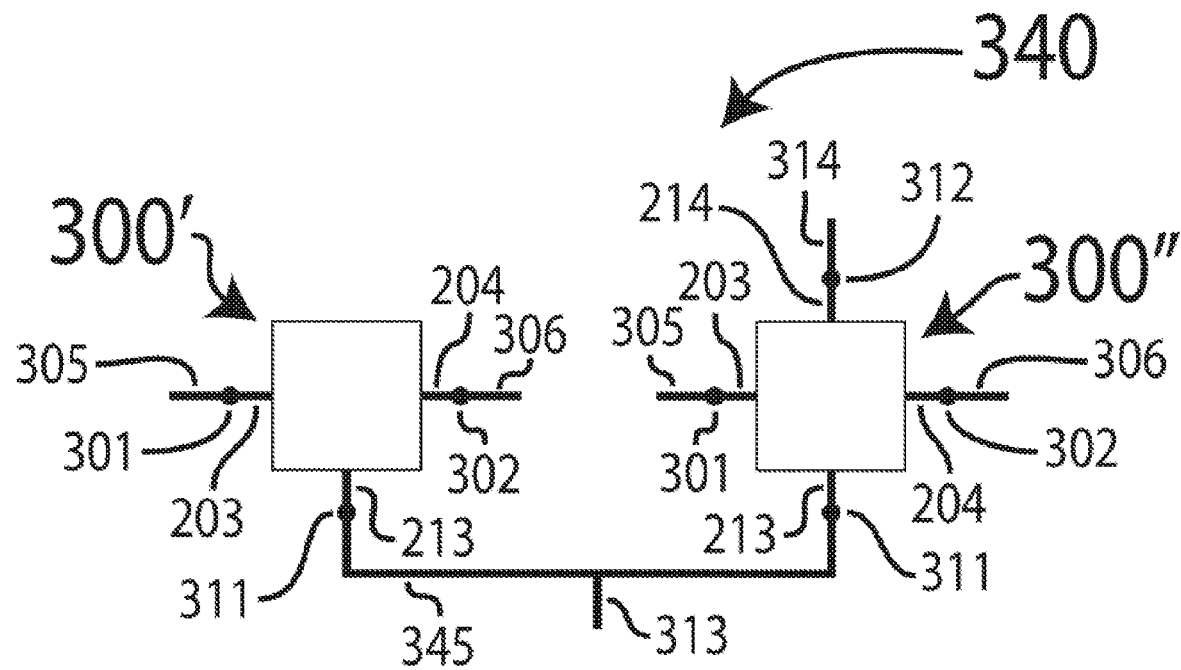
Figure 12F:
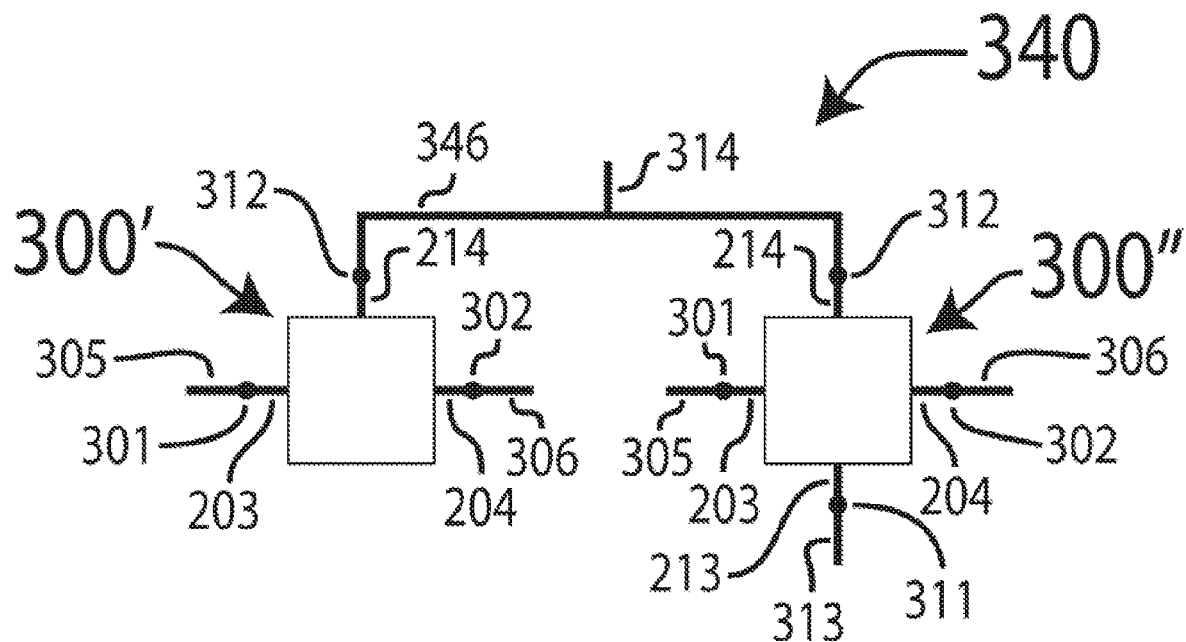

Additional fluid reactor embodiments of this disclosure are shown in FIG. 12A-12F in the form of fluid reactor unit connection pairs 340, i.e. a fluid reactor including two fluid reactor units 300, of which at least one can optionally also be dynamically self-adjusting fluid reactor unit 320, having, at a minimum, two ports (primary fluid input port 301, primary fluid output port 302, or secondary fluid port 303) of two fluid reactor units 300 connected. The fluid reactor unit connection pairs 340 can include three-port devices 300', four port devices 300", or a combination of the two. FIG. 12A depicts the case of fluid reactor unit connection pair 340 with an in-series primary fluid connection mode with primary fluid output port 302 of the first fluid reactor unit 300' connected through a sealed fluid line 341 to secondary input fluid port 301 of the second fluid reactor unit 300" included in the fluid reactor unit connection pair 340. FIG. 12B depicts the case of a fluid reactor unit connection pair 340 with an in-series secondary fluid connection mode with secondary fluid output port 312 of the first fluid reactor unit 300" connected through a sealed fluid line 342 to the secondary fluid input port 311 of the second fluid reactor unit 300" included in the fluid reactor unit connection pair 340. FIG. 12C shows a fluid reactor unit connection pair 340 with a primary input fluid-parallel connection mode with a sealed fluid line 343 connecting the primary fluid input ports 301 of two fluid reactor units 300' and 300". FIG. 12D shows a fluid reactor unit connection pair 340 with a primary output fluid-parallel connection mode with a sealed fluid line 344 connecting the primary fluid output ports 302 of two fluid reactor units 300' and 300". FIG. 12E shows a fluid reactor unit connection pair 340 with a secondary fluid-parallel connection mode with a sealed fluid line 345 connecting the secondary fluid input port 311 of two fluid reactor units 300' and 300". FIG. 12F shows a fluid reactor unit connection pair 340 with a secondary fluid-parallel connection mode with a sealed fluid line 346 connecting the secondary fluid output port 312 of two fluid reactor units 300' and 300".

Through the serial and/or parallel combination of these building blocks of fluid reactor units 300, dynamically self-adjusting fluid reactor units 320, and/or fluid reactor unit connection pairs 340, a wide variety of fluid reactors of this disclosure can be built; as such, the numerous available combinations of these building blocks are intended to be included herein. Such fluid reactors that incorporate multiple fluid reactor units 340, dynamically self-adjusting fluid reactor units 320, and/or fluid reactor unit connection pairs 340 can be used for the not intended to be limiting examples of: 1) increasing production capacity of a primary output fluid from a given primary input fluid together with one or two given secondary fluids; 2) creating a primary output fluid from multiple primary input fluids for a common secondary fluid or two secondary fluids; 3) using a single primary input fluid to create multiple primary output fluids utilizing different secondary fluids; 4) utilizing multiple primary input fluids and creating multiple primary output fluids simultaneously with/without utilizing more than one secondary fluid.

In embodiments, a fluid reactor including at least one dynamically self-adjusting fluid reactor unit 320 is used to dynamically adjust the output rate of at least one output fluid to a value close to that of a setpoint value demand signal obtained by a forecast (predetermined and non-sensor driven) output demand curve and thus can scale up or down the production of the output fluid on a predetermined demand expectation. In embodiments, a demand sensor embedded in a system needing/consuming/depending on an output fluid triggers the respected output demand change and/or adjusts the present value of such a sensor to an expected demand (target value) as signaled by such a demand sensor.

For example, in the not intended to be limiting case of a water desalination system incorporating a fluid reactor, where the primary input fluid is salt water, the secondary input fluid is dry air, and the secondary output fluid is moist air, such the demand signal may be a salinity sensor and/or an air humidity sensor. Alternatively, the forecasted output demand curve could adjust production rates of a given output fluid to an expected night, day, winter, and/or summer time demand.

For the case of a blood oxygenation system incorporating such a fluid reactor, the demand signal may be a blood oxygenation sensor connected to a biological entity (human, animal) on or near its skin or imbedded in its body or inserted in-line with or near a blood carrying vessel or delivery line that would provide a flow increase in case the blood oxygenation level drops below a given threshold (e.g., due to a higher activity state or a reduced concentration of red blood cells), or that would provide a scheduled flow change based on an anticipated demand (day/night time, for example), or a combination thereof. For example, a scheduled flow change is further corrected by the feedback from a body-worn oxygenation sensor that adjusts the oxygenation capacity of an extracorporeal or intracorporal artificial lung (a special fluid reactor embodiment) by changing the blood flow rate and/or its oxygen and/or air delivery rate to achieve a desired ≈95% oxygenation level. Alternatively, such a fluid reactor can be used as an auxiliary artificial lung that supplements a body organ (for example, lung and/or heart) whose output is changing either due to a disease, a recovery from a surgery, and/or an activity level change. Such a fluid reactor can also be used as an auxiliary aid in case the primary organ performance weakens over time or all of a sudden (backup artificial lung, backup artificial kidney, etc.).

In general, conventional membrane-dependent fluid processing applications can be also done with the various embodiments of fluid reactors discussed above which incorporate reactor core elements 100. In particular, fluid reactors optimized for a given application incorporating a hollow fiber membrane-based reactor core can be replaced with fluid reactors including fluid reactor units 300 (and/or dynamically self-adjusting fluid reactor units 320) of this disclosure incorporating at least one reactor core 200 including at least one reactor core element 100. Fluid reactors of the present disclosure can further incorporate all features and other special functional additions that benefit existing fluid reactor devices, as well as their obvious extensions and adaptations.

The flow rate $F_{SF}$ of a secondary fluid through the open-pore cellular network material of a reactor core element in up to three pathways for a 3-port or 4-port fluid reactor unit: (i) when a secondary input fluid is present, there is a flow $F_{SIF}$ from the secondary fluid external input surface to the fluid channel sidewalls; (ii) when a secondary output fluid is present, there is a flow $F_{SOF}$ to the secondary fluid external output surface from the fluid channel sidewalls; and (iii) when both a secondary input and output fluid are present there is also a flow $F_{SIOF}$ from the secondary fluid external input surface to the secondary fluid external output surface. All of these flows are inversely proportional to and dependent on the secondary fluid viscosity $\eta_{SF}$. Additionally, these flows are related to the (i) secondary input fluid flow resistance $R_{SIF}$ and permeability $K_{SIF}=1/R_{SIF}$; (ii) secondary output fluid flow resistance $R_{SOF}$ and permeability $K_{SOF}=1/R_{SOF}$; and (iii) secondary input fluid-secondary output fluid flow resistance $R_{SIOF}$ and permeability $K_{SIOF}=1/R_{SIOF}$, respectively, through the formulas $$F_{SIF} = \frac{\Delta P_{SIF}}{\eta_{SF} * R_{SIF}}, F_{SOF} = \frac{\Delta P_{SOF}}{\eta_{SF} * R_{SOF}}, \text{ and } F_{SIOF} = \frac{\Delta P_{SIOF}}{\eta_{SF} * R_{SIOF}} \quad (13)$$

with $\Delta P_{SIF}$, $\Delta P_{SOF}$ and $\Delta P_{SIOF}$ representing the average pressure drop between a respective secondary fluid ports and/or the fluid channel sidewalls of the reactor core element.

When a secondary input fluid is a gas with temperature $T_{SIF}$ flows through the open-pore cellular network material 150 from the secondary fluid external input surface to the secondary fluid external output surface of a reactor core element 100 located inside a 4-port fluid reactor unit 300 having a secondary fluid input port 311 and secondary fluid output port 312, the resulting pressure drop $\Delta P_{SIOF}$ causes a cooling of the secondary fluid gas flowing through it, i.e. the secondary output fluid gas temperature $T_{SOF}<T_{SIF}$. Flowing colder secondary input fluid gas through the body of the open-pore cellular network material 150 lowers the temperature $T_{OPCNM}$ of the body of the respective open-pore cellular network material 150, i.e. of its solid phase 152, through thermal transfer. The magnitude of the temperature drop $\Delta T_{OPCNM}$ depends, among other parameters, on the non-intended to be limiting group of: (i) the flow rate of the secondary input fluid; (ii) the thermal capacity of the secondary input fluid/secondary output fluid gas or gas mixture; (iii) the thermal conductivity of the open-pore cellular network material 150 and of all connections in thermal contact with the open-pore cellular network material 150; (iv) the thermal capacity of the fluid reactor unit housing 304 and of all its thermal connections to its reactor core elements 100; (v) the adiabatic volume expansion coefficient of the secondary input fluid while traveling through the porous open-pore cellular network material 150; (vi) the temperature, heat capacity, and flow rate of the primary fluid flowing through is respective fluid channels 104; (vii) the number and spatial distribution of the fluid channels 104 through the open-pore cellular network material 150; (viii) the amount of absorbed gas and/or released gas from the primary fluid inside the fluid channels 104; and (ix) the amount of fluid evaporated from the surface of the fluid column inside the fluid channels 104 and the heat capacity and vapor pressure of the fluid; (x) the porosity, tortuosity, and thermal conduction of the sidewall 125 neighborhood and/or of its membrane-like film covering the sidewalls 125; (xi) the amount of latent energy released by a gas component when changing from the gaseous to liquid phase; and (xii) the distance between the secondary fluid external input and output surface.

In short, while the relationship among all the above listed parameters is complex, and often best determined experimentally for a given fluid reactor unit 300 setup, it will be apparent to one skilled in the art reading this disclosure that the higher the flow rate of the secondary input fluid and the bigger the distance is between the secondary fluid external input and output surface of the respective reactor core elements 100, the colder the open-pore cellular network material 150 becomes and that there will be some time delay between starting a stable secondary input fluid flow and the $T_{OPCNM}$ reaching its stable minimum temperature.

If and when the temperature of the open-pore cellular network material 150 drops locally below the dew point of at least one gas component located inside its void space 151, then at least in this location its ligaments 153 and welds 154 start to get coated with a layer of liquid (condensed gas) thereby shrinking the available void space 151 for the gaseous remaining components. This in turn increases the flow resistance $R_{SIOF}$ for the secondary fluid transport through such at least partially "flooded" open-pore cellular network material 150.

In embodiments, the source of such a condensable component of the secondary output fluid can be the secondary input fluid itself (for example, if it is an at least partially humidified gas, e.g. $H_2O$ vapor containing gas, such as filtered room air).

In embodiments, a 4-port fluid reactor unit 300 or dynamically self-adjusting fluid reactor unit 320 at the operational temperature of its housing 304 $T_{FRUH}$ has at least one liquid primary input fluid and at least one gaseous secondary fluid. Each liquid primary input fluid has a temperature $T_{PIF}$ and each of its i-th vaporizable liquid components (LCs) has a vapor pressure $VP_i$. The liquid primary input fluid flows through fluid channels 104 of the respective reactor core elements 100 which are surrounded by porous sidewalls 125 which include "spot" welded ligaments 153 (see FIG. 6A) and/or are covered by a membrane-like film, as discussed above. In this embodiment, the sidewalls 125 have an asymmetric permeability ratio $aPR_{RCE}$ with a high permeability rate for gases and a low permeability rate for at least the liquid portion of the primary input fluid ("phobic" behavior) so that the liquid portion of the primary input fluid essentially gets mostly trapped inside the sidewalls 125. This means that right behind the depth $d_{PF}$, i.e. inside the open-pore cellular network material 150, the gas surrounding the fluid channels 104 is saturated with vapors of all available i-th liquid components, i.e. it has partial pressures $VP_i$, that are close to their dew points. If this layer of liquid gas vapors is removed at a high rate from this neighborhood, for example by flowing a sufficiently high flow rate of "dry" gas (where a "dry" gas is a gas or a gas mixture whose components all have a vapor pressure below their dew point values) through the open-pore cellular network material 150, more vapor quantities have to be evaporated from the surface of the liquid primary input fluid column inside the fluid channels 104 to replenish the lost gases so that a stable gas-liquid interface is maintained. The energy needed to gasify more liquid material, i.e. for this surface evaporation phenomenon to occur, comes from the liquid portion of the primary input fluid itself and through a heat exchange with its surrounding sidewalls 125. This results in the cooling of the liquid column inside the fluid channels 104 through evaporative heat losses. The amount of primary input fluid cooling, i.e. $\Delta T_{PIF}$, depends, among other parameters, on the latent energy of the evaporated liquid components, the heat capacity of the PIF, the thermal conductivity and thermal energy stored in the open-pore cellular network material 150, the ability of the open-pore cellular network material to compensate for the heat loss through heat exchange with the fluid reactor unit housing 304, and the flow rate of the secondary fluid.

The more the resulting local temperature $\Delta T_{OPCNM}$ of the open-pore cellular network material 150 drops, the more the ligament 153 surface area will get wet over time (i.e., coated with a liquid film) and the more the available void space 151 shrinks. In extreme cases, the void space 151 gets at least locally partially or fully filled with liquid material near the sidewalls 125. This results in an increase of the flow resistance $R_{SIOF}$ and, in particular, a dramatic increase of its secondary fluid flow resistance values $R_{SIF}$ and $R_{SOF}$.

The maximum diffusion limited primary output fluid and secondary output fluid productivity rates of a reactor core element 100 can only be practically achieved if, up to a primary fluid flow rate $F_{FCZ}^{max}$ as defined in equation (8), the quantity of secondary input fluid arriving and secondary output fluid leaving the sidewalls 125 is not a primary output fluid and/or secondary output fluid production quantity limiting factor. Increasing the flow rate of the secondary input fluid cools the open-pore cellular network material 150, which in turn limits the maximum practical delivery rate of secondary input fluid and secondary output fluid to/from the sidewalls 125 in a non-temperature-controlled reactor core element 100 and/or fluid reactor unit 300 or dynamically self-adjusting fluid reactor unit 320.

In embodiments, an open-pore cellular network material 150 is heated by external means (in either a dynamically adjusted manner with suitable control loops or a fixed static manner) sufficiently above the primary input fluid temperature $T_{PIF}$ such that, despite a given secondary fluid flow and/or liquid primary input fluid surface evaporation related open-pore cellular network material 150 temperature drop $\Delta T_{OPCNM}$, the solid phase 152 of the open-pore cellular network material 150 stays above the dew point of any condensable vapors inside the secondary fluid, i.e. $T_{OPCNM} > T_{PIF} + \Delta T_{OPCNM}$ throughout the open-pore cellular network material 150 with the optional exception of the immediate sidewall 125 neighborhood for all available secondary input fluid flow rates and sufficiently "dry" gaseous secondary input fluids. In embodiments, reactor core element 100 heating is done by irradiating the reactor core elements 100 with an electromagnetic energy that is well absorbed by the solid phase 152 of the open-pore cellular network material. In embodiments, electromagnetic energy used for heating respective reactor core elements 100 is transmitted through a relatively less absorbing fluid reactor unit housing 304, primary fluid connection manifolds, and/or connection lines. In embodiments, the gas temperature of the secondary input fluid is heated to a target output value that is appropriately set for the maximum design primary fluid flow rate or that is appropriately adjusted to the flow rate of a chosen primary input fluid liquid. In embodiments, a liquid primary input fluid is cooled prior to entering the fluid reactor unit secondary input fluid port 301 to (i) lower its surface evaporation rate, (ii) lower the dew point in the open-pore cellular network material 150, and/or (iii) allow a bigger temperature gap between the $T_{PIF}$ and $T_{SIF}$ for temperature sensitive liquid primary input fluids (for example a biological primary input fluid liquid like blood). Prior to entering the fluid reactor unit secondary input fluid port 301, the liquid primary fluid may be cooled sufficiently below the room temperature in which the fluid reactor unit 300 is used so that unheated, room temperature secondary input fluid gas can be used. In embodiments, the temperature of a liquid primary input fluid is decreased below either its source temperature or room temperature before entering the fluid reactor unit 300 and/or increased to an application specific temperature (for example, suitable for entering a human body) through a heat exchanger after leaving the fluid reactor unit 300. In embodiments, both the primary input fluid temperature is decreased from its source temperature and the gas temperature of the secondary input fluid is increased above a room temperature or above the cooled primary input fluid liquid temperature.

The maximum production performance achievable for a given reactor core element 100 for a given fluid reactor application is typically limited, among other parameters, by the minimum value of (i) the maximum primary fluid flow value $F_{FCZ}^{max}$, (ii) the maximum acceptable $\Delta P_{PF}$ for the primary input fluid and/or primary output fluid and for the open-pore cellular network material 150, (iii) the minimum acceptable fluid channel diameter $\phi_{FC}$ for a given primary input fluid and/or respective fluid reactor application, (iv) the maximum secondary input fluid and/or secondary output fluid flow rate, and (v) the maximum secondary fluid pressure drops $\Delta P_{SIOF}$, $\Delta P_{SIF}$, and $\Delta P_{SIOF}$.

EXAMPLES

Several application specific fluid reactor examples of this disclosure will now be discussed. These examples are not intended to limit the applications of fluid reactors of the current disclosure, but rather are intended to demonstrate some possible applications of the various above discussed embodiments.

Example 1: Filtration

Filtration devices are typically used to separate foreign or solid objects, also called particles hereafter, suspended in a fluid from the fluid. They fall in the categories of (i) microfiltration devices, typically used for clarification and/or sterile filtration; (ii) ultrafiltration devices, typically used for the separation of macro-molecular solutions; and (iii) nanofiltration devices, typically used for the separation of small organic compounds and selected salts from solutions.

Filtration, in the context of a fluid reaction, is a process for the separation of suspended objects (typically solids or non-dissolvable liquid components) from a fluid stream by the mechanical means of sieving. The fluid containing the objects is the primary input fluid and the suspended objects are at least one of the components of the primary input fluid. The resultant filtrate or permeate, also called secondary output fluid herein, flowing through the filter should ideally be devoid of suspended objects. The primary output fluid is a fluid similar to the primary input fluid, but with a higher concentration of the suspended objects. A fluid reactor filter unit of this disclosure has three ports and a dual or three-stage sieving filter solution. The entrance area of the respective fluid channels 104 acts as the largest and first stage particle sieve. The pores in any membrane or membrane-like primary fluid contact surface neighborhood, when available, act as the smallest and third stage particle sieve. The pores in the open-pore cellular network material 150 act as a second stage and medium size particle sieve and is, in general, the thickest part of all the different flow restriction sections that a secondary output fluid needs to travel to exit the secondary fluid external output surface of a reactor core element 100.

For example, N-type and/or S-type reactor core elements 100 having either a partially or fully non-sealed reactor core element sidewalls 129 can be used for such an application with non-E-type reactor core elements 100 having a higher secondary output fluid surface area and thus a lower secondary output fluid flow resistance. For a filter fluid reactor unit 300, the fluid flow through the open-pore cellular network material 150 is proportional to the applied pressure difference across all filter stages, i.e. between the primary input fluid port 301 and secondary fluid output port 312 of a filter fluid reactor unit 300. The rate of secondary output fluid flow is dictated by the resistance of the filter to the flow of fluid and resistance associated with the trapped particulates. The filter fluid reactor unit performance may be defined in terms of its resistance $R_{SP}$ or permeability $K_{SP}=1/R_{SP}$.

The creation of a filter fluid reactor unit 300 having a high permeability is aided by a typically highly asymmetric, nanometer-sized and uniform pore distribution, a large $V_s$ of the open-pore cellular network material 150 of the filter reactor core element 100, a relative thin thickness $d_{PF}<1$ µm of any available sidewall 125 membrane skin, and a narrow width for respective reactor core elements 100. A high pore density, e.g., $V_P \approx 80\text{-}95\%$, helps increase its permeability. If an N-type reactor core element 100 is not sufficiently "philic" for a given secondary output fluid in a filter application for a fluid reactor unit 300, then a PM-type reactor core element 100 with a more suitable "philic" solid phase 150 surface can further increase the permeability $K_{SP}$. The mechanical strength of such a reactor core element 100-filter depends primarily on the thickness of the ligaments 153 forming the respective open-pore cellular network material 150, the fracture strength of the welds 154 and the ligaments 153, and the average spacing of the welds 154.

The principle of the method of particle retention (i.e., fluid reaction in the context of this disclosure) is "sieving," although the separation is also influenced by the interaction of the solid phase 152 surface of the open-pore cellular network material 150 and the secondary output fluid. Due to the irregularity of the pores and the often-irregular shapes of the particles being filtered, there may not be a sharp cut-off size during filtration. For N-type reactor core elements 100, which typically have a more uniform pore size distribution through the open-pore cellular network material 150, some degree of in-depth separation occurs as particles move through the open-pore cellular network material 150 through a tortuous flow path. To counteract this effect, the primary fluid contact neighborhood area, in embodiments, has a narrower pore size distribution than the volume of the open-pore cellular network material 150 behind it. This results in entrapping particles almost exclusively at the primary fluid contact surface (also called herein membrane-skin) while still offering a lower hydrodynamic flow resistance behind it. This can be accomplished by using an M-type reactor core element having a thicker conformal coating 156 near the membrane skin area and/or a thin membrane film deposited over the sidewalls 125, i.e. the primary fluid contact surface neighborhood up to a depth $d_{PF}$, thus creating a sidewall 125 membrane skin.

In the filter fluid reactor 300 type of this disclosure, the buildup of a solid cake of retained particles on the fluid channels 104 sidewalls 125 may be reduced by using a cross flow mode (three-port device), i.e. allowing a permeating species (also called primary output fluid in this disclosure) with an increased suspended object concentration (compared to the incoming primary input fluid) to exit the fluid reactor unit 300. This results in a more consistent permeability value over time since the resulting cake thickness typically is finite (after an initial seasoning stage) and depends primarily on the fluid velocity inside the fluid channels 104, with higher flow velocities resulting in thinner cake film deposits.

For a given primary input fluid flow $F_{FCZ}$ into a fixed cross-sectional area $CA_{FCZ}$ of a fluid channel zone 103 of a simple reactor core element 100, equations (6) shows that the maximum fluid velocity $v_{FC}^{max}$ has a slight increase the smaller the fluid channel diameter $\phi_{FC}$ of the respective fluid channels 104 becomes. The surface area $SA_{FCZ}$ which is responsible for the third stage filtration step increases however, as equation (6) shows, approximately $\sim 1/\phi_{FC}$. The diffusion time for an average solid to reach the sidewall 125 from the fluid motion center line is $\sim (\phi_{FC})^2$, which makes the linearly increasing available surface area $SA_{FCZ}$ even more productive for smaller sized fluid channels 104. The productivity of the present filter fluid reactor unit 300 (which can also be used as a fluid concentration device) may be increased by increasing the extraction rate of the secondary output fluid and, at the same time, increasing the concentration of particulates in the primary output fluid, thereby requiring less filtration steps to achieve a targeted purity for the secondary output fluid and/or a targeted particle concentration increase for the primary output fluid.

The selection of an appropriate membrane-skin and flow resistance of the open-pore cellular network material 150 is a factor for filtration embodiments. Adsorption phenomena at the sidewall 125 can play an important role in fouling. For example, hydrophobic membrane-skins, for example PTFE based M-type reactor core elements (manufactured as discussed above), can have a greater tendency to foul, especially by proteins. Such absorption can be avoided with a proper surface coating of the membrane skin and/or open-pore cellular network material 150. Fouling can generally be reduced by using reactor core elements 100 with smaller sized fluid channels 104 since (i) reactor core elements 100 provide proportionally more filtration surface area and (ii) smaller size fluid channels 104 typically have increased flow velocities and fouling is flow velocity dependent.

In embodiments, flushing a fluid reactor unit 300 with a low surface energy liquid (for example alcohol) prior to a (high surface energy) water-based fluid filtration processing helps to get the air out of the void space 151 faster and therefore get a filtration operation started faster. In another filter fluid reactor embodiment, reactor core stacks 210 are used with a height H resulting in a $\Delta P_{FC} \approx \Delta P_{PS}$ for the chosen primary input fluid flow rate $F_{PRCS}$ related through equations (11), (9), (2), and (1). In embodiments, the compression strength of the solid phase open-pore cellular network material 150 of the reactor core element 100 of which the reactor core stack 210 includes is increased to a level where it is able to operate at a suitable pressure difference. In embodiments, since the concentration of extracted particles increases along the height of a reactor core stack 210, the design of at least one reactor core element 100 is varied along the height of the reactor cores 100 to accommodate the change in particle concentration, thus allowing a higher production rate for a given reactor core 200 volume.

In embodiments, the design of the reactor core element 100 is optimized in such a way that the practical maximum secondary fluid flow rate is not the highest performance limiting parameter for a filtering application of a specific secondary output fluid. In other embodiments, the filter fluid reactor unit 300 is vibrated, for example, with mechanical and/or ultrasound means to further minimize the fouling of the sidewalls 125. In embodiments, the secondary fluid travel distance between the secondary fluid external input surface and secondary fluid external output surface is smaller than the length of a reactor core element 100. In embodiments, the secondary fluid travel distance is ½ or ¼ of the length of a rectangular simple reactor core element 100.

Example 2: Degasification/Gasification of a Liquid

Degasification, in the context of fluid reaction embodiments, is a process for removing at least one dissolved gas component (secondary output fluid) from a liquid primary input fluid thereby producing a primary output fluid with a lower concentration of the gas. Gasification is the reverse process for dissolving at least one gas component (secondary input fluid) into a liquid (primary output fluid). The liquid of the primary input fluid is the at least one component of the primary input fluid for both cases.

Applications of a degassing fluid reactor unit 300 include the removal of dissolved gases from a liquid delivery system used in a CVD system for semiconductor or other processing operation, for example Ar or $N_2$ dissolved in trichlorosilane, silicon tetrachloride, titanium chloride, etc. Other fluid degassing applications include the removal of $O_2$ and/or $CO_2$ from a water or other aqueous solution to prevent the formation of rust or bacteria in water treatment systems; degassing of solvents to prevent reactions for air sensitive liquids or for when bubble formation at a liquid-gas interface becomes a problem (for example, a liquid flow controller); degasification of liquids which need to be frozen, thus preventing bubble formation in the solid state; and $CO_2$ removal from wine. Gasification of a liquid is a process that can be used, for example, to create new chemical components and/or chemical reactions in a given liquid, such as nanoparticles, nanowires, platelets, quantum dots, initiate polymerization, salt formation, pH change of a solution, changing the balance of a chemical reaction, creation of carbonated water, etc. Absorption of $O_2$ and/or removal of $CO_2$ and/or bubble removal from blood are falling under the category of gasification/degasification and will be discussed further in a separate fluid reactor application example below.

The solubility of gas in a liquid at low concentrations obeys Henry's law, i.e. the amount of a dissolved gas in a liquid is proportional to its partial pressure in the gas phase. As shown above with equation (7a), (5b) and (8), the critical diffusion time $t_c \sim \phi$, the active surface area $SA_{FCZ} \sim h/(\phi_{FC}*(1+g_{FC}/\phi_{FC})^2$, and the maximum flow rate which is still able to saturate a liquid with a gas for a given reactor core element 100 with height h is $F_{FCZ}^{max}(h=\sim h/(\phi_{FC}+g_{FC})^2$. Reactor core elements 100 with smaller fluid channels 104 have the potential to be more productive as long as the secondary fluid flow resistance through the open-pore cellular network material 150 is not the limiting factor of the production rate of the reactor core element 100. Therefore, placing the liquid/gas interface of a solution under a vacuum and/or a "dryer" atmosphere (i.e. an inert atmosphere with a lower partial pressure of the to be removed gas) makes the dissolved gas less solvable. Equivalently, by using a secondary input fluid containing a gas at a higher partial pressure and/or absolute pressure, the gas becomes more soluble in the primary input fluid.

Thus, to create the maximum degassing rate, the void space 151 of the open-pore cellular network material 150 should ideally be void of any partial pressure of the gas that should be removed. This can be accomplished by using a partial vacuum as the secondary output fluid or by using an inert gas as secondary input fluid and removing the inert secondary input fluid gas together with any degassed gas from the primary input fluid as secondary output fluid.

The gasification/degasification fluid reactors of this disclosure thereby utilize primarily the approximately linearly higher surface area of reactor core elements 100 and the quadratically faster critical diffusion time with the fluid channel diameter to build a higher performing fluid reactor unit 300 (as compared to hollow fiber membrane-based fluid reactors). In embodiments, the fluid reactor unit 300 has degassing properties and in other embodiments, it has gasification properties. In further embodiments, the fluid reactor unit 300 has both gasification and degasification properties for different gases.

The maximum secondary fluid flow rate is limited by, amongst other things, the vapor pressure of liquid components of the primary fluid and the evaporation energy needed to gasify the liquid component. Two high secondary fluid flow rates can therefore cause surface evaporative cooling of the liquid column inside the fluid channels 104. In particular, this is important for aqueous primary fluids given the very large surface area of these reactor core element 100 embodiments and the very high latent evaporation energy requirement, which can lead to ice formation inside an open-pore cellular network material 150 and/or flooding it with liquid (re-condensed evaporated primary fluid liquid components), for example due to dropping below its dew point.

To minimize condensation of vaporizable liquid components of the primary input fluid or secondary input fluid inside the open-pore cellular network material 150, various heating solutions can be used to keep the open-pore cellular network material 150 sufficiently warm to stay above the dew point for all gas phase components in the secondary fluid path.

In embodiments, the sidewall 125 is coated with a thin metal film, for example Pd, having a thickness of ≤1 µm that provides a solid gas diffusion barrier layer that preferentially diffuses one gas faster than the other, for example $H_2$ and the reactor core element 100 are heated inside a fluid reactor unit housing 304 to a sufficiently high temperature to achieve sufficient $H_2$ diffusion rate through the Pd-membrane film. Such heating can also be done with heating the fluid reactor unit housing 304 and thus indirectly heating the reactor core elements 100, which are sealed, for example, with high temperature bonding means to primary fluid manifolds and/or connection lines. In embodiments, M-type reactor core elements 100 (N-type with a Pb membrane film inside the fluid channel 104) inside a heated fluid reactor unit housing 304 are used as replacements for traditional high temperature Pd-based $H_2$ purifiers. Such purifier fluid reactor application embodiments may utilize reactor core elements 100 having fluid channels 104 with a fluid channel diameter down to the 5-10 µm level, thus resulting in higher fluid channel surface area, shorter critical diffusion times, and a thinner (than the state of the art for commercially available Pd based $H_2$ purifiers) Pd film membrane film supported by nano-porous sidewalls 125.

Example 3: Artificial Lung (Extra Corporeal Oxygenator)

A human adult body contains, on average, 5 L of blood. Blood performs a wide range of functions: (i) it supplies $O_2$ and nutrients to different tissues of body, (ii) it removes waste products like urea, lactic acid and $CO_2$, (iii) it provides immunity against foreign particles, (iv) it helps transport hormones, (v) it aids in blood clotting which is a natural repair mechanism of cells, (vi) it regulates and maintains normal temperature, (vii) it maintains pH balance inside the body; and (vii) the components of the blood help in homeostasis. Blood is primarily composed of plasma (55 vol %) and formed elements (45 vol %). Blood plasma includes 91% by weight of water, 7% of various plasma proteins, and 2% of other solutes including various waste products. The formed elements include mostly red blood cells, white blood cells, and platelets. The typical size of normal red blood cells is 6-8 µm, white blood cells is 12-17 µm, and platelets is 2-3 µm. The primary function of platelets is to stop bleeding by clumping and clotting blood vessel injuries.

An average healthy adult human lung has a capacity of ≈6 L, a surface area of 80-100 m², and processes about 5 L/min of venous blood at rest, i.e. it adds $O_2$ to and removes $CO_2$ from the blood. The average tidal volume (volume of air breathed in and out at rest) is about 500 ml at 12 breaths/min, resulting in a total air flow in/out of the lung of 6 L/min. However, during excessive and/or heavy exercise it can increase up to 5-6 times the normal amount. Under normal conditions for an adult human at rest, the hemoglobin in the blood leaving the lung is greater than 95% saturated and has an $O_2$ delivery rate of 950-1,150 ml/min to the body. At rest, the adult consumes 200-250 ml/min of $O_2$ and exhales about 240 ml/min of $CO_2$ and deoxygenated (venous) blood returns to the lung still roughly 75% (70-78%) saturated.

The heart typically has a systolic peak pressure of 120 mmHg at the left ventricle exit. Venous blood exits the heart at the right ventricle and enters the lung in pressure pulses varying between 25 mmHg and 8 mmHg and exits the lung at 10 mmHg to 5 mmHg, having on average a pressure drop of 10 mmHg across an average adult lung. Before the air reaches the alveolus of the lung it gets fully humidified at the vapor pressure of the body temperature. The alveolar partial pressure $P_AO_2$ of $O_2$ can be calculated from the formula $$P_AO_2 = FiO_2 * (P_{atm} - P_{H2O}) - \frac{P_aCO_2}{R} \qquad (14)$$

with $FiO_2$ representing the fraction of $O_2$ of the breathable gas (room air~0.21) inspired into the lungs, $P_{atm}$ is the pressure of inspired gas (760 mmHg at sea level), $P_{H2O}$ is the vapor pressure of $H_2O$ (47 mmHg at 37° C.), $P_aCO_2$ is the partial pressure of $CO_2$ (passed through the blood vessel wall into the alveolar sac and typically ≈40 mmHg), and R is the respiratory quotient (typically ~0.8). For normal breathing levels of air at 760 mmHg into adult human lungs, $P_AO_2$≈100 mmHg. For a human lung, the $O_2$ content $C_aO_2$ in the arterial blood vessels of the lung is related to the partial pressures of the gas inside the alveolus sac and can be derived from the formula $$C_aO_2 = C_a^{plasma}O_2 + C_a^{Hgb}O_2 = \qquad (15)$$
$$\left(\frac{0.003 \text{ mL}}{mmHg * dL} * P_aO_2\right) + \left(1.4 \frac{\text{mL } O_2}{\text{g Hgb}} * Hgb * S_aO_2\right)$$

with $C_a^{plasma}O_2$ representing the amount of $O_2$ dissolved in the blood plasma, with 0.003 mL/(dL*mmHg) being the Henry constant, and with $C_a^{Hgb}O_2$ representing the amount of $O_2$ bound to the available hemoglobin cells in the arterial blood. $P_aO_2$≈$P_AO_2$–10 mmHg represents the partial pressure in units of mmHg of $O_2$ inside an arterial lung vessel, Hgb represents the hemoglobin content in blood in units of g/dL (typically 14 g/dL for an adult human), and $S_aO_2$ represents the $O_2$ saturation level of hemoglobin. The partial $O_2$ pressure drop between the alveolus sac and the arterial vessel side is caused by a single cell thick membrane between them. For the typical values listed above, for an adult human lung at sea level $C_aO_2$≈20%=200 (sccm $O_2$)/(L of blood) with <2% of this $O_2$ being stored in the blood plasma and the rest being stored in the hemoglobin molecules inside the red blood cells of the blood. Each hemoglobin molecule can bind a maximum of four $O_2$ molecules and each g of it can hold 1.4 mL of $O_2$. The hemoglobin $O_2$ saturation level $S_aO_2$ dependence on $P_aO_2$ is sigmoid shaped and can be calculated from the formula at standard conditions of a blood temperature $T_{blood}=37°$ C. with a pH value $pH_{blood}=7.4$ $$S_aO_2 = \frac{1}{1+\frac{23,400}{150*P_aO_2 + P_aO_2^3}} \quad (16)$$

Commercially available artificial lungs like extra corporeal membrane oxygenators, (ECMOs) used during cardiopulmonary bypass (CPB) based on hollow fiber membrane technology, also called hollow fiber oxygenators (HFO) with in-line heat exchangers are often tested under ISO 7199: 15 L/m of water for heat exchanger, $FiO_2=100\%$, 7 L/m of bovine blood flow at 37° C. with hemoglobin concentration of Hbg=11.5 g/dL, and a venous blood oxygen saturation level $S_vO_2=64\%$. Under these test conditions, available hollow fiber oxygenators typically have (i) an $O_2$ transfer rate of 375-440 ml/min, (ii) a $CO_2$ transfer rate of 250-400 mm Hg, (iii) an $O_2$ efficiency of 118-235 ml O2/min/m², (iv) a membrane surface area of 1.5-3.7 m², (v) a priming volume of 180-560 ml, (vi) a blood pressure drop of $\Delta P_{PF}=90\text{-}300$ mmHg, (vii) an index of hemolysis of 500-29,000, and (viii) a heat exchange efficiency of 0.44-0.61.

In embodiments, reactor core elements 100 are used to build four-port blood oxygenators fluid reactor units 300 and/or dynamically self-adjusting fluid reactor units 320 for cardio-pulmonary bypass applications. In such an application, the primary input fluid is venous blood, i.e. blood with a lower $O_2$ saturation level $S_aO_2$ (typically <80%) and the primary output fluid is arterial blood, i.e. blood with having a high $O_2$ saturation level $S_aO_2$ (typically >90%). Where the embodiment is a dynamically self-adjusting fluid reactor unit 320, it may include, on the primary fluid input and/or output side of the device, at least one regulator 326 or controller 327 in the form of a heat exchanger and/or a blood pump (for example, a peristaltic pump) having a controllable output rate, pressure and/or blood temperature. Additionally, a dynamically self-adjusting fluid reactor unit 320 may include at least one incorporated or remote sensor 325 for measuring and transmitting at least one parameter to an externally controllable controller 327, control box 328 and/or master control box 329. The at least one parameter, when measured, is selected from the non-intending to be limited group of (i) flow rate, (ii) pressure, (iii) $O_2$ concentration or $O_2$ saturation level, (iv) $CO_2$ concentration, (v) hemoglobin concentration, (vi) heparin or other anticoagulant concentration, or (vii) other species or drugs concentration.

In embodiments, the reactor core elements 100 are an E-type, S-type and M-type and optionally also PM-type, where any M-type and PM-type reactor core elements 100 are hydrophobic in order to help contain the blood, in particular the plasma portion of the blood, inside sidewalls 125 of the fluid channels 104 of the reactor core element. In embodiments, the reactor cores 200 are made from simple reactor core elements 100 having a rectangular cuboid shape. In other embodiments, the respective reactor cores 200 are made with complex reactor core elements 100 having at least one secondary fluid channel 132 and/or alignment channel 119. In embodiments, any sealing on secondary fluid surfaces for the S-type reactor core elements 100 is done in step 186 or 190 with a carbon infiltration step in such a manner that all the outside surfaces of the reactor core element 100 are sealed against blood plasma leakage while at least the sidewalls 125 are still porous through most of their extruded lengths. In embodiments, such S-type reactor core elements 100 have the longer sides of such rectangular-shaped simple reactor core elements 100 unsealed in a process step 190, for example through a vibratory polishing step as discussed above, thus forming E-type rectangular reactor core elements 100 having a slit-like secondary fluid external input surface and secondary fluid external output surface. In other embodiments, the narrow sidewalls 129 of the reactor core elements 100 are sealed with a sealant or plastic molding during their incorporation into reactor core subcomponents 250, for example comprised of a parallel arrangement of single reactor core elements 100. In other embodiments, available sidewalls 127 get at least partially unsealed after such a prior sealing step.

In embodiments, the M-type and optional PM-type reactor core elements 100 have a PTFE coating at least over the depth $d_{PF}$ of the sidewalls 125. In embodiments, the final and most outer surface layer of the sidewalls 125 is an antithrombotic coating. In embodiments, such an antithrombotic coating is only completed after the fluid reactor unit housing 304 has been sealed up and is accomplished by flowing at least one fluid temporarily through the fluid reactor unit secondary input fluid port 301, removing the fluid, and drying the remaining surface coating layer, thus surface treating all the paths the primary fluid is taking, i.e. all surfaces to which blood is exposed while inside a fluid reactor.

At least two of the components of the primary input fluid that are subject to the asymmetric permeability of the sidewalls 125 are the blood plasma and the red blood cells. In embodiments, substantially only $O_2$, $CO_2$, and $H_2O$ vapors can easily cross the effective membrane barrier film and/or membrane-like sidewall 125 neighborhood.

The secondary input fluid (sometimes referred to by those skilled in the art as a sweep gas) is a breathable and optionally heated gas or gas mixture having a temperature TSIF and is selected from at least one element of the non-intended to be limiting group of filtered room air, human breathable gas, gas with $FiO2 \geq 0.21$, gas with $FiO2 \approx 100\%$, TSIF>TPIF, humidified gas mixture with PH2O<vapor pressure of H2O at TPIF, and gas with $PCO2 \approx 0$ mmHg or with PCO2>0 mmHg. In embodiments, the sweep gas contains at least 20% oxygen and less than 10% carbon dioxide. The primary output fluid has a reduced O2 concentration, an increased concentration of CO2 over the primary input fluid, and optionally a lower or higher temperature, but is otherwise substantially similar to the primary input fluid that enters the open-pore cellular network material 150 of the reactor core elements 100 through the secondary fluid external input surface.

In embodiments, the condensable vapor content of the breathable secondary input fluid gas and its temperature $T_{SIF}$ and/or the primary input fluid temperature $T_{PIF}$ of the venous blood is controlled in such a manner that the $T_{SIF}$ is sufficiently higher than $T_{PIF}$ so that the resulting local open-pore cellular network material 150 temperature $T_{OPCNM} \geq 0.5°$ C.+$T_{PIF}$ to keep the gaseous atmosphere everywhere inside the open-pore cellular network material 150 above the dew points of all the vaporizable liquid components of the primary input fluid and/or all condensable gas components of the secondary input fluid. In embodiments, a dynamically self-adjusting fluid reactor unit 320 is used with one or more control loop systems and at least one sensor 325 to regulate at least one of the temperatures of the primary input fluid, secondary input fluid, and/or primary output fluid temperature, and/or control the fluid flow for the primary and/or secondary input fluid where the control loops receive at least a present value feedback signal for the total primary input fluid input flow rate and/or $T_{PIF}$ temperature sensor. In embodiments, the at least one control loop reacts to the present value of a $S_aO_2$ and/or $CO_2$-blood concentration level sensor 325 of the primary input fluid (venous blood) or primary output fluid (arterial blood) and/or a forecasted time dependent demand table, manual entered demands signal, remote communicated demand signal and/or a combination thereof.

In embodiments, the $P_{H2O}$ of the secondary input fluid is lower, or at least not higher than, the $H_2O$ vapor pressure relative to temperature $T_{PIF}=T_{blood}$ of the primary input fluid (venous blood). Such a partial humidification of the secondary input fluid together with its secondary input fluid gas-heated open-pore cellular network material 150 assist in minimizing the formation of condensed water inside the void space 151 and, at the same time, minimizing the surface evaporation of $H_2O$ from the plasma inside the fluid channels 104, thus minimizing any performance over time due to an increase in the secondary input fluid flow resistance $R_{PS}$ resulting from a partially to a fully flooded void space 151.

In embodiments, a fluid reactor unit 300 or dynamically self-adjusting fluid reactor unit 320 is used for cardiopulmonary bypass and/or an extra corporeal membrane oxygenator application for providing cardiac and respiratory support to humans (and/or animals) whose heart and lungs are unable to provide an adequate amount of gas exchange or perfusion to sustain life. For example, in the short term, such fluid reactors can be used during a surgical operation; in longer terms, such fluid reactors can be used until a heart and/or lung organ has recovered its normal functionality or has been replaced with a transplanted organ or equivalent performing system. The priming volume of such a fluid reactor unit 300 embodiment is the volume of all fluid channels 104 inside a respective reactor core 200 and the volume of all respective primary fluid connection lines and/or manifolds.

In embodiments, the fluid reactor unit 300 is designed in such a manner that it is compatible with an existing extracorporeal membrane oxygenation control system, e.g., a fluid reactor unit 300 embodiment can be a drop-in replacement for a traditionally used hollow fiber oxygenator unit that typically is connected in-line at least with a heat exchanger and a blood pump, as is known to those skilled in the arts. Embodiments of reactor core elements 100, for example the ST1-ST4 or ST51-ST54 shown in FIG. 5 and described further in TABLES 1 and 2, have fluid channels 104 with fluid channel diameter in the 20-47 µm range, i.e. in the range that is usable for blood flow since (i) the human blood viscosity is basically near its minimum in this range and (ii) hollow fiber oxygenators typically have an arterial blood filter in the range of 20-45 µm either built-in or connected in-line to its output. The fluid channels 104 of the reactor core elements 100 thus provide an automatic built-in arterial blood filter functions, i.e. blood sieving function, based on the size of the chosen fluid channel diameters that help to reduce gaseous micro-emboli counts and volume and blood clots.

The typical adult patient population requiring an oxygenator typically needs an oxygenator with max blood flow capacity that is related to the patient's body weight: 50% have <80 kg body weight and need a 5 L/min oxygenator; 40% have a body weight between 80-100 kg and need a maximum 6 L/min oxygenator; and 10% have a body weight>100 kg and need an up to 8 L/min oxygenator. In embodiments, a fluid reactor unit 300 used as a blood oxygenator has a maximum rated blood flow capacity $F_{FRU}^{max}$ in the range of 0.5-2.5 L/min (typically used for pediatric application), 2.5-5 L/min (young or small adults) or 2.5-6 L/min (optimized adults), or 5-8 L/min (full adults). In embodiments, the reactor core is either (i) a single reactor core element, (ii) a parallel arrangement of reactor core elements (e.g., one version of a parallel reactor core stack), (iii) a parallel arrangement of groups of parallel arranged reactor core elements, or (iv) a parallel arrangement of reactor core stacks (e.g., one version of a parallel reactor core stack). In embodiments, the reactor core sub-components of a fluid reactor unit have a maximum primary input fluid pressure drop $\Delta P_{PF}$ of (i) ≈10 mmHg (to match an adult human lung), (ii) <140 mmHg (to match the typical maximum systolic blood pressure of a heart of an adult human at rest), or (iii) $\Delta P_{PF}$<300 mmHg (to match the maximum pressure drop output of typically commercially available hollow fiber oxygenators). Equations (5a), (9), (10), (11), and (12) describe the relationship between the pressure drop $\Delta P_{PF}$ and blood flow rate $F_{FCZ}$ for a given type of reactor core element, reactor core stack, or parallel reactor core stack. As discussed above, a human lung operates on a pressure drop of 10 mmHg, but a hollow fiber oxygenator operates traditionally in the range of 90-250 mmHg, i.e. close to the systolic pressure of the heart of 120 mmHg.

The diffusion constant of $O_2$ at 37° C. into plasma $D_{O2}^{plasma}$=2.18E-5 cm²/s and for blood at a hematocrit $H_t$=43% level (volume percentage of red blood cells blood) is $D_{O2}^{blood}$=1.62E-5 cm²/s. The dynamic viscosity of blood depends on fluid channel diameter, hematocrit $H_t$, and blood temperature $T_{blood}$. For normal conditions ($H_t$≈45%, $T_{blood}$=37° C.), $\eta_{blood}$≈0.0028 Pa*s. Due to the Fåhraeus-Lindqvist effect, viscosity of human blood is smaller for flow channel diameters<300 µm and reaches its minimum at $\phi_{FC}$≈8 µm for gas flow channels in in-vitro experiments. Part of this flow channel diameter dependent dynamic viscosity effect is related to the Fåhraeus effect which results from human blood cells preferentially traveling in a faster moving, more central flow velocity stream, i.e. preferentially staying away from the wall of a fluid channel where primarily only plasma is flowing, thus leading to a diameter dependent blood viscosity decrease portion minima at 10-15 µm. Ignoring these potential additional flow capacity improvements arising from a lower dynamic viscosity of blood when small diameter fluid channels 104 are used as shown in TABLES 1 and 2, i.e. using a high viscosity value for the venous blood, i.e. $\eta_{PF}=\eta_{blood}$≈0.0028 Pa*s, the maximum potential blood flow rate, i.e. primary input fluid flow rate $F_{FCZmax}$, and associated pressure drop $\Delta P_{PFmax}$ of the reactor core element 100 can be calculated with the aid of equations (8) and (8a). For example, for ST1 and ST51 type reactor core elements having a height h=2 mm and a fluid channel diameter $\phi_{FC}$=46.5 µm, $F_{FCZ}^{max}$=1.41 L/min for ST1 elements and $F_{FCZ}^{max}$=1.76 L/min ST51 elements and $\Delta P_{PF}^{max}$=95 mmHg for both. For ST2 and ST52 type reactor core elements having a height h=2 mm and a fluid channel diameter $\phi_{FC}$=36.5 µm, $F_{FCZ}^{max}$=1.96 L/min for ST2 elements and $F_{FCZ}^{max}$=2.46 L/min for ST52 elements and $\Delta P_{PF}^{max}$=252 mmHg for both. Clearly for the ST1 or ST51 type samples, the value of $\Delta P_{PF}^{max}$ is below the typical systolic peak blood pressure of 120 mmHg, while for the ST2 and ST52 type samples, $\Delta P_{PFmax}$ exceeds the typical systolic peak blood pressure by a factor of two, but is still within the range of commercially available extra corporeal membrane oxygenators.

The above-listed maximum flow rate capacity of a reactor core element 100 depends upon the secondary input fluid arriving at a sufficient rate to the sidewalls 125 and the secondary output fluid is leaving them at a sufficient rate such that the oxygenation and depletion of $CO_2$ (fluid reaction capacity) is not limited by the transport through the open-pore cellular network material 150. Therefore, in embodiments, where the secondary input fluid and secondary output flow rate is the primary capacity limiting factor, the actual maximum fluid reaction capacity of a respective reactor core element 100 will be $<F_{FCZ}^{max}$ and the pressure drop will be $<\Delta P_{PF}^{max}$.

In embodiments, under the above listed standard test conditions (i.e. retrofittable to current available heart-lung control systems incorporating hollow fiber membrane based ECMOs), type ST1 or ST51, reactor core elements 100 have a maximum usable blood flow capacity of ≈80 ml/min or ≈100 ml/min and a pressure drop of $\Delta P_{PF}$≈6.5 mmHg. In embodiments, eight simple reactor core elements are connected in a parallel fashion to form a parallel reactor core stack 230. Eight of these parallel reactor core stacks 230 are then connected in parallel with each other to form a reactor core 200 with an ≈5.1 L/m or ≈6.4 L/m maximum blood flow capacity and an approximate pressure drop $\Delta P_{PF}$≈6.5 mmHg across each respective reactor core element 100 (neglecting pressure drop across delivery lines and respective primary fluid manifolds), with respective elements 100 having a type 105-*t*, 105-*s* or 105-*c* sealing zone.

In other embodiments, four simple reactor core elements are connected in series to form a reactor core stack 210 thus providing an estimated maximum blood flow capacity of 320 ml/min with top and bottoms located sealing zones 105-*t* (and optionally a 105-*s* or 105-*c* sealing zone for the last element 100) and a total pressure drop of $\Delta P_{PF}$≈104 mmHg inside the fluid channels 104, without sufficient increased plasma leakage to choke the secondary output fluid delivery/removal rate. Otherwise, the stacking of four reactor core elements 100 will have a lower maximum blood flow rate limit and more reactor core stacks 210 will need to be connected in parallel to achieve a target maximum blood flow capacity rate. Connecting sixteen such reactor core stacks 210 in parallel to each other with a maximum blood flow capacity of ≈320 ml/min to form a reactor core 200 can result in an estimated maximum blood flow rate of ≈5.1 L/min.

The volume and surface area of all the fluid channels 104 of sixty four reactor core elements 100 of ST1 type may be 19 ml and 1.7 m² and for ST51-Type may be 24 ml and 2.1 m², i.e. the active surface area is similar to a typical hollow fiber oxygenators with 5-6 L/m capacity, but the priming volume, depending on the design of the primary fluid connection manifold, can be smaller than that of currently available hollow fiber oxygenators. While both embodiments potentially achieve the same maximum blood flow rate for the same number of the same reactor core elements 100, the latter design may be designed to have a smaller total primary fluid connection manifold volume, and therefore can have an even smaller priming volume; the former has a lower pressure drop and as a result also a lower plasma leakage rate into the surrounding open-pore cellular network material 150 and, therefore, ultimately has a higher maximum flow rate under standard test conditions and potentially has a lower rate of gaseous micro-emboli count and volume. The former embodiment also has lower pressure drop, thereby enabling the utilization of reactor core elements 100 with even smaller fluid channel diameters, thereby possible further reducing the gaseous micro-emboli count and. or volume.

Since the blood flow path through reactor core elements 100 incorporated into such fluid reactor unit oxygenators is basically straight, ultra-short (as short as approximately 2 mm long when no reactor core stacks 210 are used to build reactor cores 200), and subject to the Fåhraeus effect, there is much less red blood cell and platelets interaction with the "membrane surface," i.e. sidewalls 125, compared to when blood travels a tortuous path through hollow fibers devices. Therefore, oxygenator embodiments (with an appropriate antithrombotic coating) may have a reduced normalized index of hemolysis, i.e. less red and white blood cell damage and/or less platelet loss. This can help to minimize the trauma to the blood during an oxygenation phase, which may reduce post-surgical health complications.

Similarly, other types of simple reactor core elements 100, as listed for example in TABLE 1 or TABLE 2, can be used to make a parallel arrangement of reactor core sub-components 250 with the reactor core sub-components 250 being parallel reactor core stacks 230 and the parallel reactor core stacks being made of single simple reactor core elements 100. The pressure drop will increase with diminishing fluid channel diameters, but reactor core elements 100 can be selected to still have a pressure drop $\Delta P_{PF}$<120-140 mmHg or <250 mmHg if other benefits can still be derived, for example, less gaseous micro-emboli counts and/or volume, less hemolysis, less platelets loss, less red or white blood cell loss, and/or less coating of the sidewall 125 with blood proteins or other components.

In other embodiments, a dynamically self-adjusting fluid reactor unit 320 is used in combination with a one-time use fluid reactor unit 300 for blood oxygenation in a veno-arterial extra corporeal membrane oxygenator, veno-venous extra corporeal membrane oxygenator, or other extra corporeal membrane oxygenator mode. In embodiments, a minimal temperature difference between the secondary input fluid and the primary input fluid is achieved by heating the reactor core elements 100 to reduce condensation of vapor components of the secondary input fluid and/or secondary output fluid inside the open-pore cellular network material 150. In embodiments, the blood temperature of the blood collected from a vein is lowered before entering the fluid reactor unit and then is heated up to the targeted temperature before entering the body again through an artery or vein. In other embodiments, the breathable gas is heated, or both processes are done together by a suitable control algorithm and with suitable target output value input modes. In another mode, a suitable control system optimized all the process parameters in such a manner that, for a given primary output fluid demand, the least amount of gaseous micro-emboli counts and volume and/or hemolysis, and/or other parameters are optimized such that post-operative complications are reduced. In such embodiments, the parallel arrangement of parallel reactor core stacks 230 (where the parallel reactor core stacks 230 include single simple or complex reactor core elements) provides the design flexibility since such reactor cores 200 can be configured to operate at low pressure drops $\Delta P_{PF}$ for any primary input fluid flow rate. While such a dynamically self-adjusting fluid reactor unit 320 system is possibly more expensive than currently utilized systems for hollow fiber oxygenators, these embodiments potentially use a lower cost disposable fluid reactor unit (because potentially less reactor core elements 100 are needed) and/or allow a lower post-surgical complication rate. Additionally, the control loop parameter settings of the dynamically self-adjusting fluid reactor unit 320 system may optionally be tailored (customized) to a given patient, for example based on body weight and various health factors.

Other non-limiting, illustrative configurations for artificial lung devices into which the presently described core elements may be substituted are disclosed in U.S. Pat. Nos. 4,657,743; 5,192,320; 6,495,101; U.S. Published Patent Application No. 2018/0036468; U.S. Published Patent Application Nos. 2018/0036459 and 2018/0036468; and U.S. Pat. No. 8,685,319.

Based on the above teachings, those skilled in the art can optimize the design and manufacturing for other applications of fluid reactor unit 300 and/or dynamically self-adjusting fluid reactor unit 320 embodiments, and obvious extensions to such other applications are thereby intended to be included in this disclosure.

What is claimed is:

1. A reactor core element for fluid treatment comprising:
a free standing, substrate-free structure defining
  an input surface;
  an output surface;
  first and second sidewalls connecting the input and output surfaces; and
  a plurality of fluid channels extending from the input surface to the output surface,
wherein the free standing, substrate-free structure includes: carbon nanotubes mechanically interlinked by spot welds provided by a coating, and a void phase configured to permit fluid flow through the free-standing, substrate-free structure in a tortuous path from the first sidewall to the second sidewall; and a hydrophobic material deposited on at least a portion thereof to render the at least a portion superhydrophobic.

2. The reactor core element of claim 1 wherein the coating is a conformal CVD coating.

3. The reactor core element of claim 2 wherein the conformal CVD coating is carbon-based.

4. The reactor core element of claim 1 wherein each fluid channel of the plurality of fluid channels includes a permeable sidewall covered with a membrane film.

5. A reactor core subcomponent comprising a first reactor core element in accordance with claim 1 connected in parallel or serially with a second reactor core element.

6. A reactor core subcomponent comprising a first reactor core element connected in parallel or serially with a second reactor core element, wherein the first and second reactor core elements are both reactor core elements in accordance with claim 1.

7. A reactor core comprising:
a reactor core input surface and a reactor core output surface; and
at least one reactor core subcomponent including at least one reactor core element in accordance with claim 1.

8. A fluid reactor comprising a housing and a reactor core in accordance with claim 7.

9. The fluid reactor of claim 8 wherein the housing includes a primary fluid input port, a primary fluid output port, and at least one secondary fluid port.

10. The fluid reactor of claim 8 further comprising a sensor, a regulator, and a controller configured to communicate with the sensor and the regulator to minimize any difference between a present value of a parameter measured by the sensor and a target value for the parameter.

11. A method of compositionally transforming a primary fluid comprising:
passing the primary fluid through a plurality of fluid channels extending from an input surface to an output surface of a free standing, substrate-free reactor core element; and
passing at least one secondary fluid through a void phase of the reactor core element in tortuous path, the void phase between first and second sidewalls defined by the free standing, substrate-free reactor core element and formed by ligaments mechanically interlinked by spot welds provided by a coating,
whereby the primary fluid is compositionally changing while passing through the plurality of fluid channels.

12. The method of claim 11 wherein passing the primary fluid through the plurality of fluid channels comprises passing the primary fluid through at least one fluid channel having a sidewall configured to keep at least one component of the primary input fluid inside the fluid channel.

13. The method of claim 12 wherein the sidewall of the at least one fluid channel is further configured to permit passage of the secondary fluid therethrough.

14. The method of claim 13 wherein the sidewall of the at least one fluid channel is configured to permit passage of the at least one component of the primary input fluid at a rate less than the rate at which the secondary fluid passes therethrough.

* * * * *